(12) United States Patent
Hermiston et al.

(10) Patent No.: US 7,829,329 B2
(45) Date of Patent: Nov. 9, 2010

(54) ADENOVIRAL VECTORS FOR TREATING DISEASE

(75) Inventors: Terry Hermiston, Corte Madera, CA (US); Lynda K. Hawkins, Germantown, MD (US); Leisa Johnson, Richmond, CA (US)

(73) Assignee: Onyx Pharmaceuticals, Inc., Emeryville, CA (US)

( * ) Notice: Subject to any disclaimer, the term of this patent is extended or adjusted under 35 U.S.C. 154(b) by 119 days.

(21) Appl. No.: 10/306,275

(22) Filed: Nov. 27, 2002

(65) Prior Publication Data

US 2004/0101512 A1 May 27, 2004

Related U.S. Application Data

(63) Continuation-in-part of application No. 09/347,604, filed on Jul. 2, 1999, now abandoned, which is a continuation-in-part of application No. 09/290,732, filed on Apr. 13, 1999, now abandoned.

(60) Provisional application No. 60/083,033, filed on Apr. 24, 1998, provisional application No. 60/117,103, filed on Jan. 25, 1999.

(51) Int. Cl.
*C12N 15/00* (2006.01)
*C12N 7/00* (2006.01)
*A01N 43/04* (2006.01)

(52) U.S. Cl. ............... 435/320.1; 435/235.1; 514/44 R

(58) Field of Classification Search ............ 435/320.1, 435/235.1; 514/44
See application file for complete search history.

(56) References Cited

U.S. PATENT DOCUMENTS 6,100,086 A * 8/2000 Kaplan et al. ............ 435/320.1

OTHER PUBLICATIONS

Bett et al. PNAS 91:8802-8806, 1994.*
Virology Jan. 15, 1985;140(1):28-43; "DNA sequence of the early E3 transcription unit of adenovirus 5," Cladaras C, Wold WS.
Mol Ther. Apr. 2003;7(4):435-7, "A multitasking oncolytic adenovirus vector," Toth K, Doronin K, Tollefson AE, Wold WS.
J Virol. Oct. 1992;66(10):5914-23, "Map of cis-acting sequences that determine alternative pre-mRNA processing in the E3 complex transcription unit of adenovirus," Brady HA, Scaria A, Wold WS.
Virology. Dec. 1994;205(2):406-16, "Fine-mapping of sequences that suppress splicing in the E3 complex transcription unit of adenovirus," Scaria A, Wold WS.

* cited by examiner

*Primary Examiner*—Fereydoun G Sajjadi
(74) *Attorney, Agent, or Firm*—Gary R. Fabian; Gregory J. Giotta

(57) ABSTRACT

Adenoviral vectors, including mutant adenoviruses, that have restriction sites in the E3 region, that facilitate its partial or total deletion, or select genes contained therein, and optionally compositions and methods for substituting heterologous gene(s) in the partially or totally deleted E3 region(s), which heterologous gene(s) being operably linked to endogenous adenoviral transcriptional control sequences will exhibit an expression pattern, both in terms of timing and degree of expression, similar to the endogenous adenoviral gene(s) that it replaces, and further optionally including mutations in other parts of the adenoviral genome, including certain E1B or E1A regions, and that have applications for diagnosing or treating disease, preferably disease involving unwanted cell growth, including cancer.

8 Claims, 42 Drawing Sheets

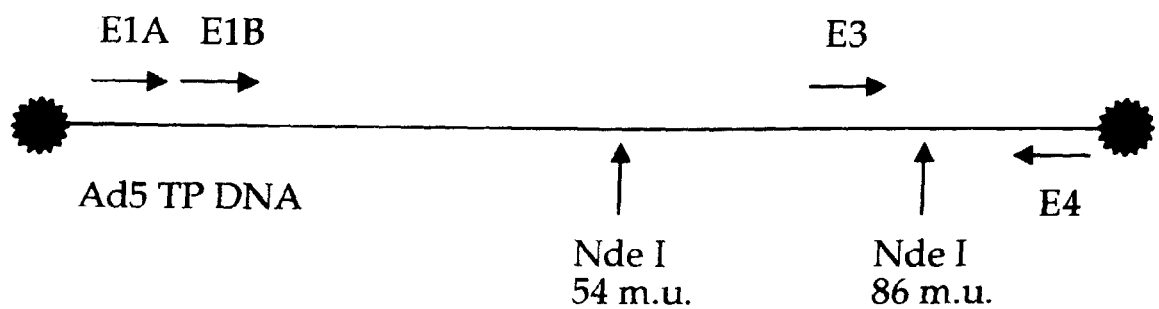
Ad5 TP DNA  Nde I 54 m.u.  Nde I 86 m.u.  E4
Cut with NdeI
Ligate
Transfect A549 cells
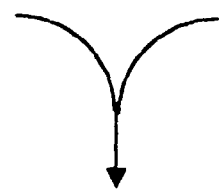
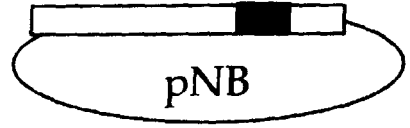  pNB
Isolate plaques and screen for recombinant virus
FIGURE 2

CD Assay
0.6 µg protein/rxn

M  Ad  4  8  12  24  36  48  60  72  84  96  120  +

301
← U
← C

302

303

304

FIGURE 12 mTNF secreted into the culture medium by ONYX 320-infected cells

(In a one hour window)

17 kD →

4  8  12  24  36  48  60  72  84  96  120  144 ← hr. postinfection

*Method*: Medium changed one hour before indicated time. Aliquot removed after one hour for analysis.

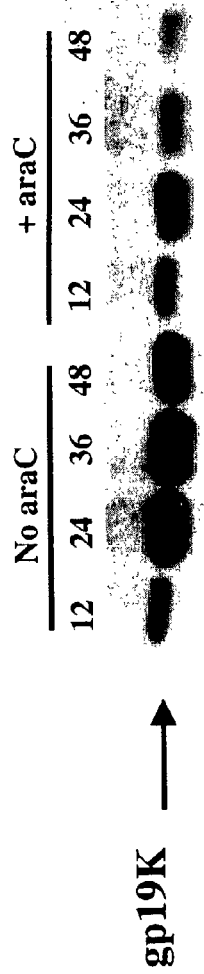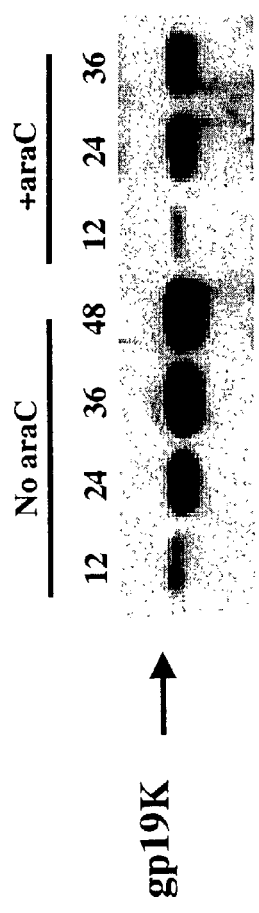
FIGURE 27

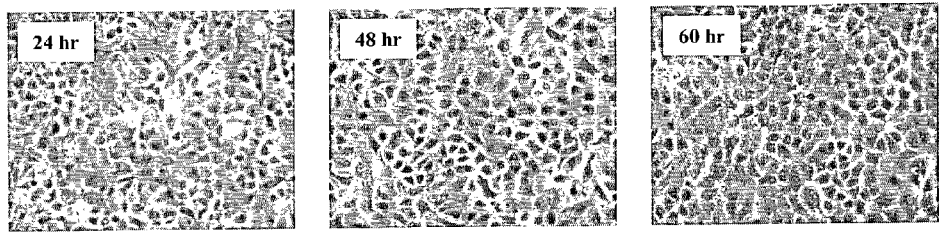
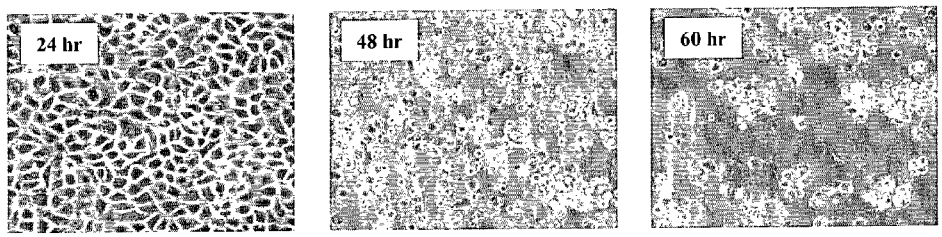
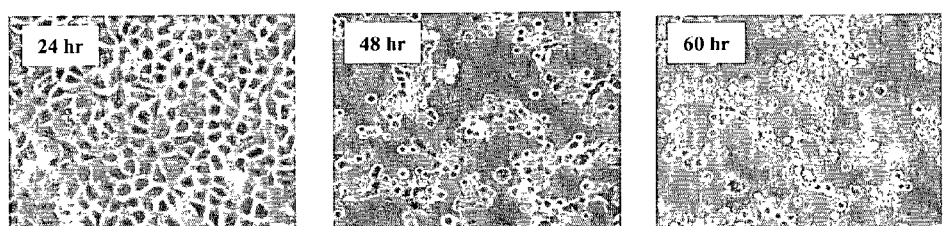
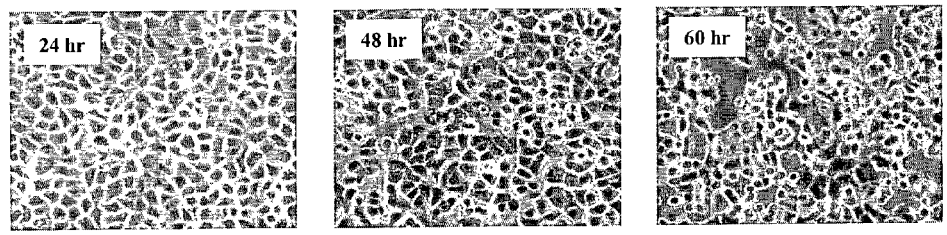
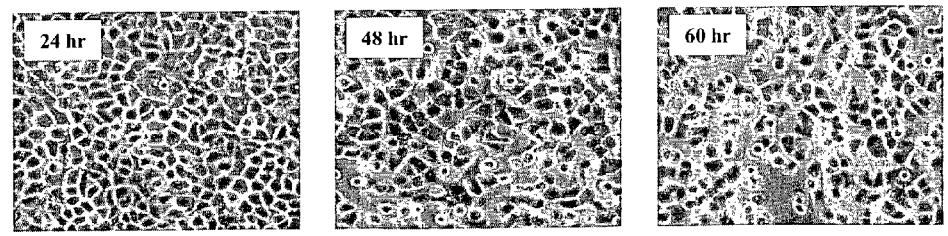
FIGURE 41

ADENOVIRAL VECTORS FOR TREATING DISEASE

This application is a continuation-in-part of U.S. patent application Ser. No. 09/374,604 filed Jul. 2, 1999 now abandoned, which is a continuation-in part of U.S. patent application Ser. No. 09/290,732, filed Apr. 13, 1999, now abandoned, which in turn claims priority from U.S. Provisional Application No. 60/083,033, filed Apr. 24, 1998 and U.S. Provisional Application No. 60/117,103 filed Jan. 25, 1999.

FIELD OF THE INVENTION

The invention described herein relates generally to the field of gene therapy, and more specifically to adenoviral vectors that have prophylactic or therapeutic applications.

BACKGROUND OF THE INVENTION

Adenovirus is a vector of choice for performing gene therapy. See, Jolly, D., Cancer Gene Therapy, vol. 1, no. 1, 1994: pp51-64. The well-characterized molecular genetics of adenovirus render it an advantageous vector in this regard. Adenoviruses are nonenveloped icosohedral double-stranded DNA viruses with a linear genome of approximately 36 kilobase pairs. Each end of the viral genome has a short sequence known as the inverted terminal repeat (or ITR), which is required for viral replication. Portions of the viral genome can be readily substituted with DNA of foreign origin, and furthermore, recombinant adenoviruses are structurally stable.

The adenovirus replication cycle has two phases: and early phase, during which 4 transcription units E1, E2, E3, and E4 are expressed, and a late phase which occurs after the onset of viral DNA synthesis when late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth.

To date most adenoviral vectors are based on viruses mutated in E1, E3 or a site upstream of E4 which provide for sites for the insertion of foreign DNA. The majority of vectors are based on adenovirus mutants which lack the E1 region of the genome. By deleting this region, the virus is rendered replication incompetent while simultaneously allowing for the insertion of foreign genes.

There are numerous reports on the use of adenovirus for gene therapy. For example, Smith, et al., Nature Genetics, Vol. 5, pgs. 397-402 (1993) discloses the administration to mice of an adenoviral vector including a human Factor IX gene. Such administration resulted in efficient liver transduction and plasma levels of human Factor IX that would be therapeutic for hemophilia B patients. Human Factor IX levels, however, slowly declined to baseline by nine weeks after injection, and were not re-established by a second vector injection. Smith, et al., also found that neutralizing antibodies to adenovirus block successful repeat administration of the adenovirus.

Kozarsky, et al., J. Biol. Chem., Vol. 269, No. 18, pgs. 13695-13702 (May 6, 1994) discloses the infusion of an adenoviral vector including DNA encoding the LDL receptor to rabbits. Stable expression of the LDL receptor gene was found in the rabbits for 7 to 10 days, and diminished to undetectable levels within 3 weeks. The development of neutralizing antibodies to the adenovirus resulted in a second dose being completely ineffective.

Kass-Eisler, et al., Gene Therapy, Vol. 1, pgs. 395-402 (1994) suggest that a T-cell response contributes to, but is not solely responsible for, the limited duration of expression in adults from adenovirus vectors. The authors further show that cyclosporin A is not effective in blocking the humoral response to the vector.

Fang, et al., J. Cell. Biochem., Supplement 21A, C6-109, pg 363 (1995) disclose the attempted re-injection of an adenovirus vector in dogs that were treated with cyclosporin A, an immunosuppressive agent. Such attempted re-injection was unsuccessful.

Yang, et al., Proc. Nat. Acad. Sci., Vol. 91, pgs. 4407-4411 (May 1994) describe recombinant adenoviruses in which the E1a and E1b regions have been deleted. Such viruses also include a heterologous gene. When these adenoviruses are administered to an animal host, cells harboring the recombinant viral genome express the heterologous gene as desired; however, low level expression of viral genes also occurs.

As exemplified above, adenoviruses can be efficient in gene transfer into cells in vivo, and thus may be employed as delivery vehicles for introducing desired genes into eukaryotic cells. There are, however, several limitations to adenovirus gene transfer which are due in part to host responses directed at either the adenovirus vector particle, breakdown products of the vector particle, or the transduced cells. These host responses include non-specific responses and specific immune responses. The non-specific responses include inflammatory and non-inflammatory changes. An example of the latter is a change in host cell gene expression. Specific immune responses include various cellular responses and humoral antibody responses. Cellular responses include those mediated by T-helper lymphocytes, T-suppressor lymphocytes, cytotoxic T lymphocytes (CTL), and natural killer cells.

Despite the high efficiency of adenovirus vector mediated gene transfer, the transient nature of adenovirus vector mediated gene transfer has suggested that repeat administrations of adenovirus vectors may be necessary. Recent studies in cotton rats, however, have demonstrated that host immune responses directed towards adenoviral vectors correlate with decreased efficiency of gene transfer and expression after repeated administration. Yei et al., Gene Therapy, 1: 192-200 (1994). The E3 region encodes several immunoregulatory proteins, which are not required for viral replication: gp19K, 10.4K, 14.5K and 14.7, and one protein, 11.6K, that is required for lysis of infected cells, and release of infectious progeny. Additionally, the E3 region also contains open reading frames for two proteins, 12.5k and 6.7k, whose functions have yet to be identified.

While the E3 region is not essential for viral replication, it does play a key role in modulating the host immune or inflammatory responses to the virus. For instance, in the case of the immune response it is known that gp19K binds to MHC class 1 molecules in the endoplasmic reticulum, thus inhibiting its glycoslation and transport to the surface of the virally infected cells. Consequently, the infected cells are not recognized as foreign by cytotoxic lymphocytes. See, Burgert, B., et al., Proc. Natl. Acad. Sci USA 1987; vol. 8: 1356-60.

Because of the many functions of the E3 region, it would be desirable to have an adenoviral vector for gene therapy applications that would permit one to delete particular regions of E3, and substitute foreign DNA, depending on the intended application of the vector. For example, there are described deletions in the E3 region that result in the removal of 1.88 kb between the XbaI sites. See, Berkner, K. and Sharp, P., (1983) Nucleic Acids Res. Vol. 11, pages 6003-6020, and Haj-Ahmad, Y. and Graham, F. (1986) J. Virol. Vol. 57, pages 267-

274. Further, there is described compositions and methods for constructing adenovirus having insertions or deletions in both the E1 and E3 regions. See also, Ginsberg, H. S. et al., Proc. Natl. Acad. Sci. USA 1989, vol. 86, pp. 3823-7.

Thus, while these vectors have mutations in the E3 region, or large parts of the region deleted, to date there does not exist a vector that allows one to remove select parts of the E3 region and substitute foreign DNA, such that the expression of the substituted foreign, or heterologous DNA, retains the expression profile of the gene(s) deleted.

SUMMARY OF THE INVENTION

A first object of the invention is to describe methods and compositions for treating or preventing cancer wherein said methods and compositions involve administering to a patient in need of treatment a recombinant adenoviral vector which vector has the properties of infecting and replicating in the cancer, and, optionally expressing at least one heterologous gene for treating the cancer, which heterologous gene is expressed preferrably during the replication, or late, phase of said viral vector and the expression is regulated by endogenous adenoviral transcriptional regulatory sequences.

A second object of the invention is to describe recombinant adenoviral vectors that have restriction sites in the E3 region that facilitate partial or total deletion of this region, or select genes contained therein, and optionally substitute two heterologous genes, which genes exhibit an expression pattern, both in terms of timing and degree of expression, substantially similar to the endogenous adenoviral genes that they replace as a consequence of retaining the endogenous adenoviral transcriptional regulatory sequences.

A third object of the invention is to describe recombinant adenoviral vectors that have restriction sites in the early region genes of the E3 region that encode the 6.7K and gp19K proteins which facilitate the removal of such genes while retaining the endogenous adenoviral transcriptional regulatory sequences.

A fourth object of the invention is to describe recombinant adenoviral vectors that have restriction sites in the E3 region that encode the 10.4K, 11.6K, 14.5K, and 14.7K proteins which facilitate the removal of genes that encode such proteins while retaining the endogenous adenoviral transcriptional regulatory sequences.

A fifth object of the invention is to describe recombinant adenoviral vectors that have restriction sites in the E3b region that facilitate partial or total deletion of this region, or select genes contained therein, and compositions and methods for substituting foreign, or heterologous, DNA therein, and which vectors retain the endogenous adenoviral transcriptional regulatory sequences.

A sixth object of the invention is to describe methods for making recombinant adenoviral vectors that have restriction sites in the E3 region that facilitate partial or total deletion of the E3 region, or select gene(s) contained therein, and which vectors retain the endogenous adenoviral transcriptional regulatory sequences.

A seventh object of the invention is to describe host cells containing recombinant adenoviral vectors that have a partial or total deletion of the E3 region, or select gene(s) contained therein, and which vectors retain the endogenous adenoviral transcriptional regulatory sequences.

An eighth object of the invention is a description of recombinant adenoviral vectors that have restriction sites in the E3b region that facilitate partial or total deletion of the E3b region, or select gene(s) contained therein, and which vectors retain the endogenous adenoviral transcriptional regulatory sequences that are operably linked to a heterologous gene to express the heterologous gene as a late adenoviral gene.

A nineth object of the invention is a description of recombinant adenoviral vectors that have restriction sites in the E3 region that facilitate partial or total deletion of the E3 region, or select genes contained therein, while maintaining the endogenous adenoviral transcriptional regulatory sequences including virions; E3SV, E3SV+V, E3SV+B, and E3SV+V+B.

A tenth object of the invention is a description of recombinant adenoviral vectors that have restriction sites in the E3 region that facilitate partial or total deletion of the E3 region wherein such vectors also have mutations elsewhere in the adenoviral genome, preferably in the E1A, E1B, and/or E4 regions.

An eleventh object of the invention is a description of methods and compositions for diagnosing or treating disease, preferably diseases involving unwanted cell growth, including neoplasia, using recombinant adenoviral vectors that have restriction sites in the E3 region that facilitate partial or total deletion of the E3 region, or select genes contained therein, wherein the adenoviral vectors have substituted in the E3 region genes that encode medically beneficial proteins. Preferred substituted genes include heterologous genes including negative selection genes, preferably cytosine deaminase, and thymidine kinase.

These and other objects of the present invention will become apparent to one of ordinary skill in the art upon reading the description of the various aspects of the invention in the following specification. The foregoing and other aspects of the present invention are explained in greater detail in the drawings, detailed description, and examples set forth below.

BRIEF DESCRIPTION OF THE DRAWINGS

FIG. 2 shows the production of recombinant virus using pNB and Ad5 TP-DNA (m. u. stands for map units).

FIG. 12 shows a CD assay on cell lysates prepared from cells infected with viruses Onyx 301, Onyx 302, Onyx 303, Onyx 304, and Onyx 305 at different times post infection using 0.6 ug protein/reaction.

FIG. 27 shows Western blots of the E3 protein gp19K from cells infected with either Ad5 or Onyx 320 and incubated in the presence or absence of araC.

Figure 37:
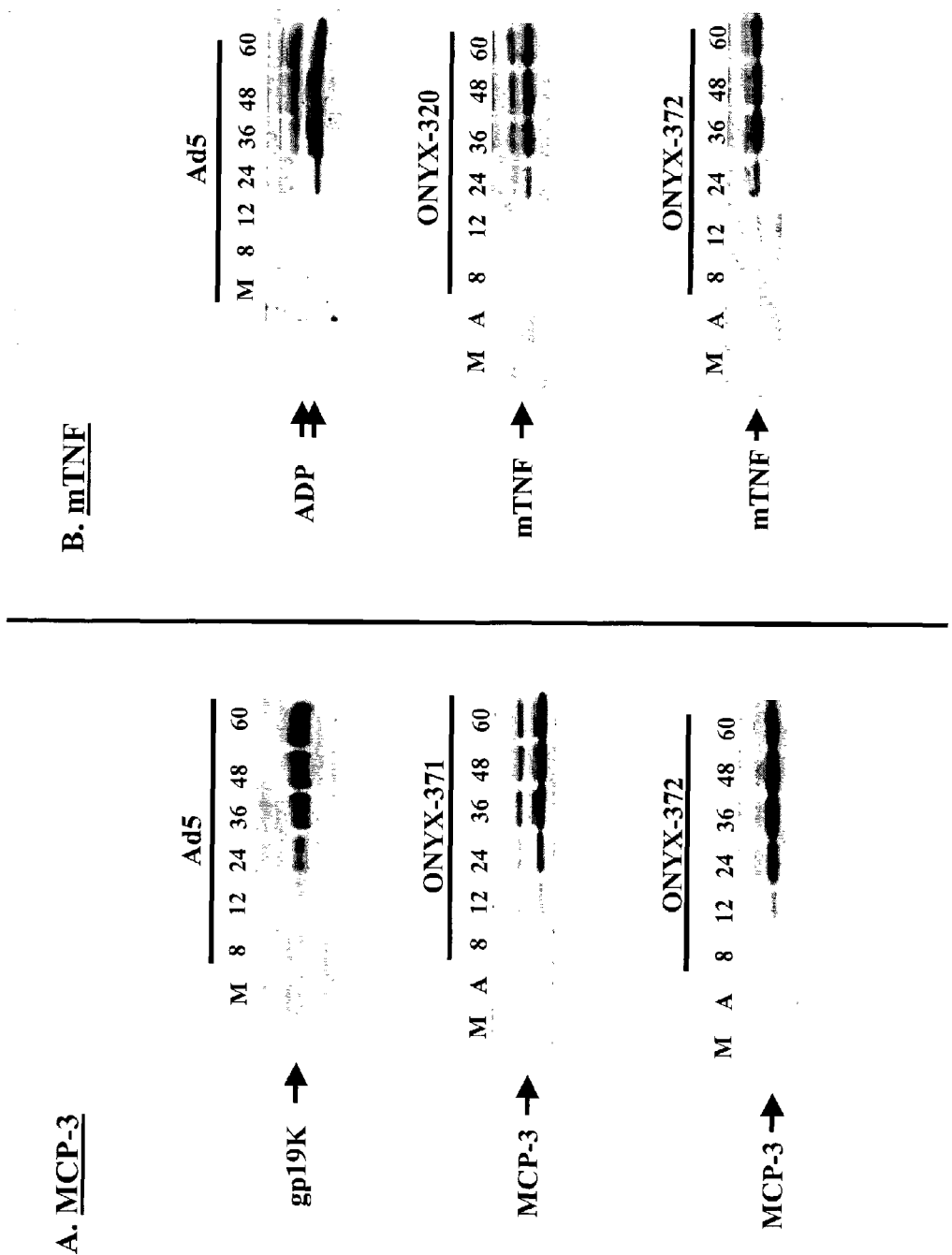

FIG. 37 shows heterologous gene protein expression. Western blot analysis was performed on protein extracts from Ad5-infected cells, and from conditioned cell culture medium from ONYX-371, -320, -and -372-infected cells. The numbers above each blot indicate the time post infection. The "M" and "A" indicate mock-infected and Ad5-infected cells, respectively, harvested at 24 hours post infection. For analysis of MCP-3 (panel A) and mTNF (panel B), expression represents the protein secreted into the medium 1 hour prior to the time point indicated. Panel A shows endogenous gp19K protein expression for Ad5 or heterologous gene (MCP-3) protein expression for 371 and 372. Panel B shows endogenous ADP expression for Ad5 and mTNF expression for 320 and 372.

Figure 38:
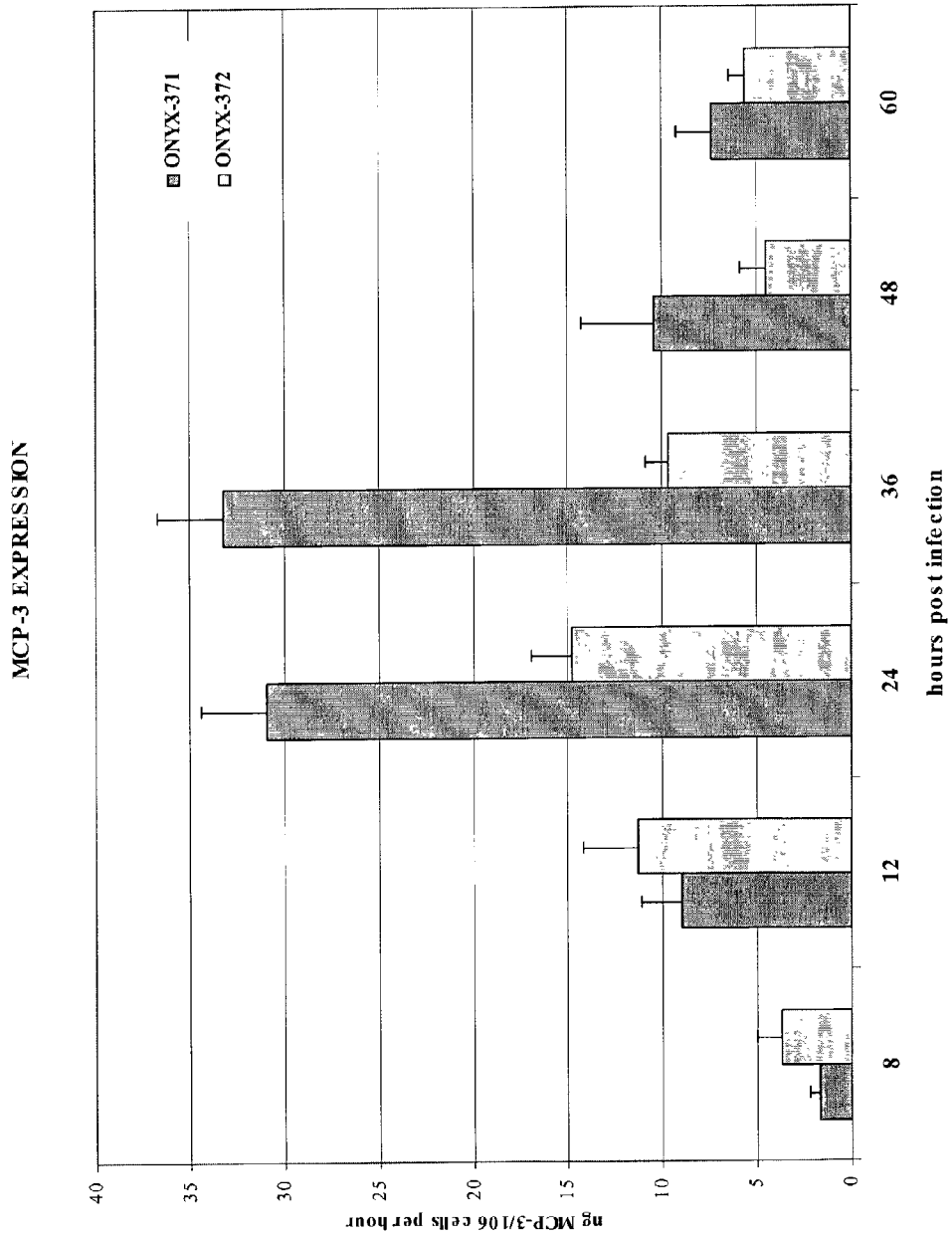

FIG. 38 shows quantitation of MCP-3. An ELISA was done to quantitate the amount of the heterologous gene MCP-3 secreted into the culture medium during a one-hour time period over the course of the infection. Values are expressed as ng of MCP-3 synthesized per million cells per hour. This experiment was done in replicates of 4 and the standard deviation is shown by error bars. The numbers on the x-axis represent the time post infection that the samples were collected.

Figure 39:
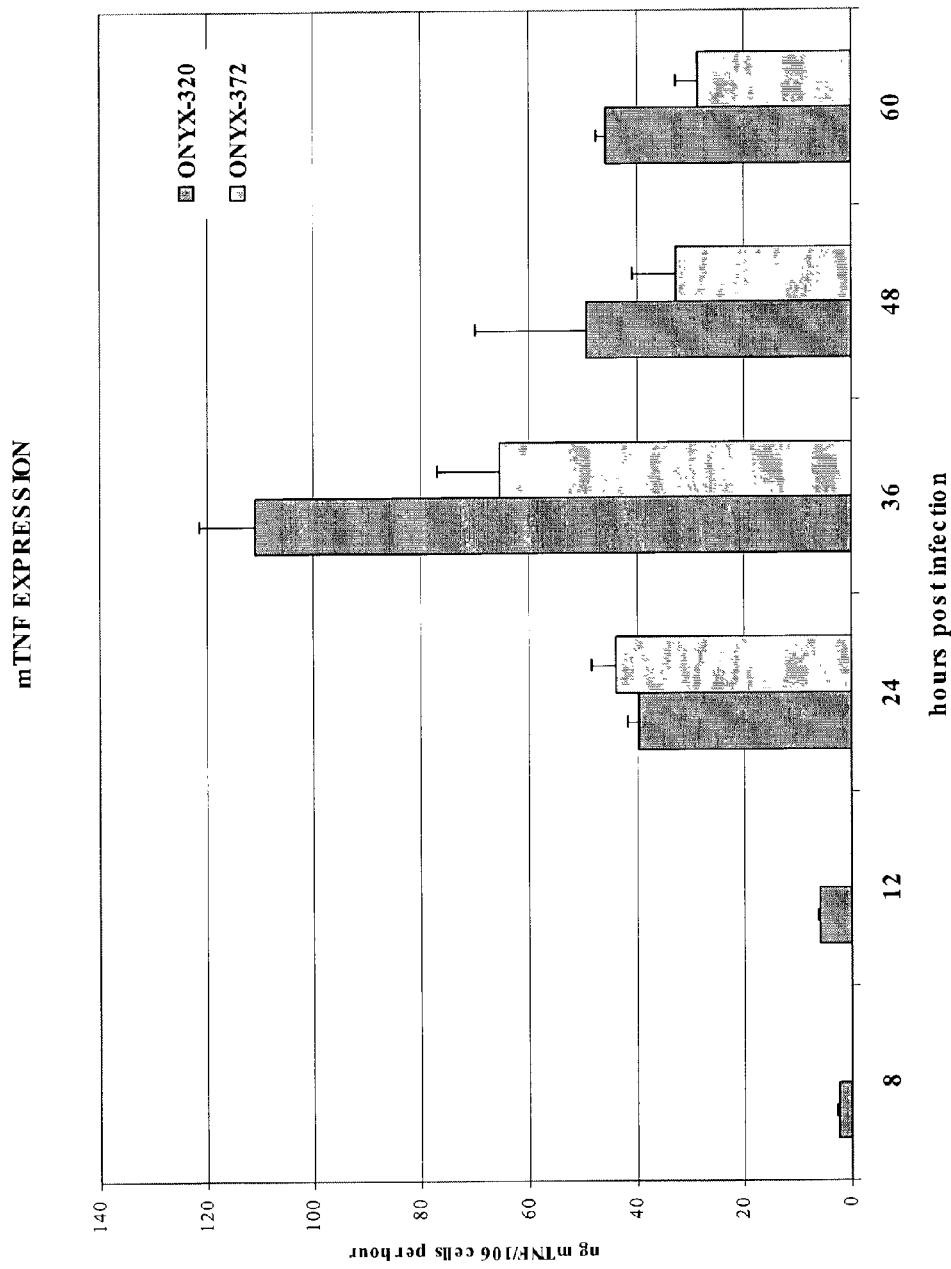

FIG. 39 shows qunatitation of mTNF. An ELISA was done to quantitate the amount of the heterologous gene mTNF secreted into the culture medium during a one-hour time period over the course of the infection. Values are expressed as ng of mTNF synthesized per million cells per hour. This experiment was done in replicates of 4, and the standard deviation is shown by error bars. The numbers on the x-axis represent the time post infection that the samples were collected.

Figure 1:
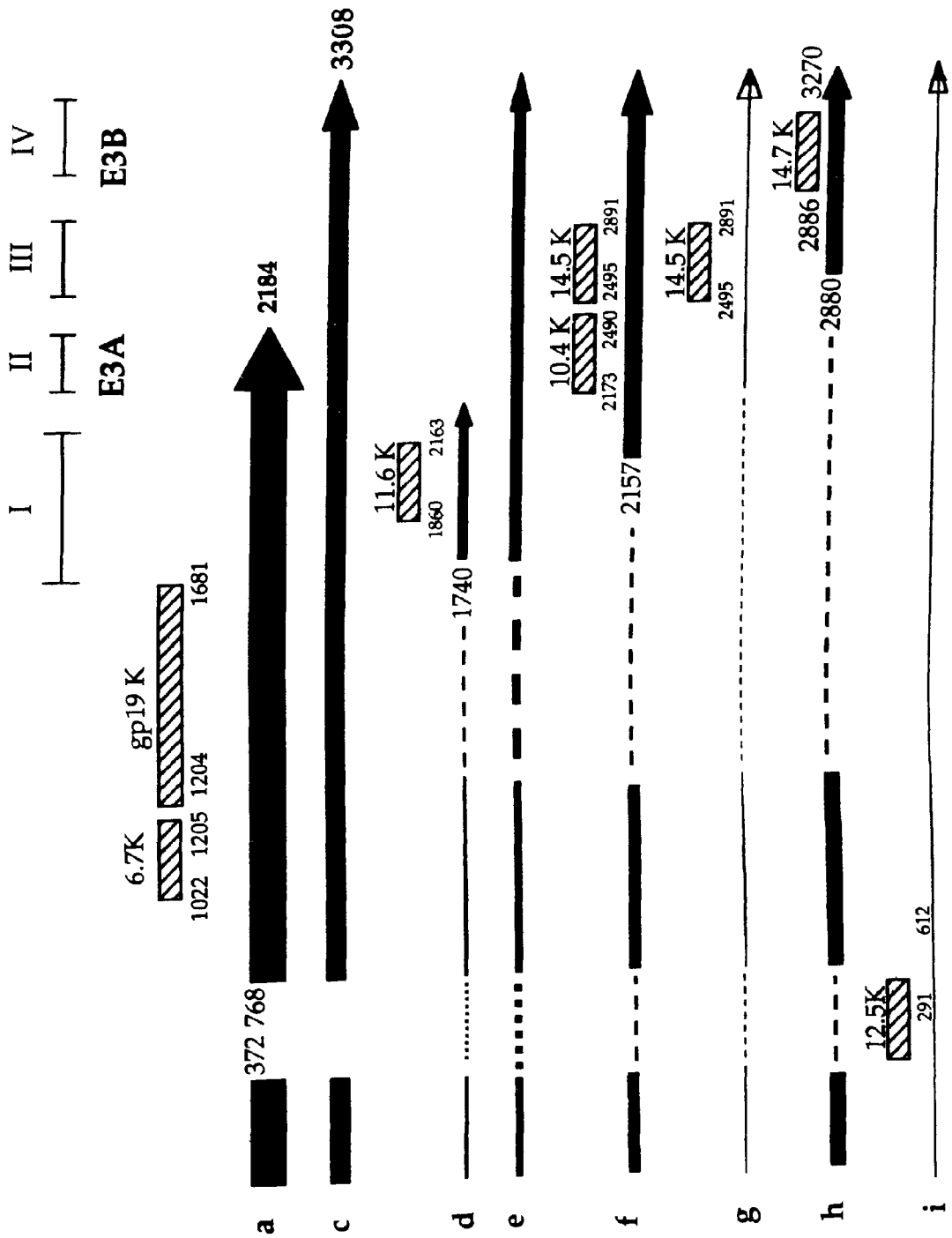
FIG. 1 shows a map of the E3 region transcriptional unit of adenovirus type 5. The split arrows (a, c, d, e, f, g, h and i) indicate the spliced structures of the mRNAs (open rectangles or solid lines represent Exons; dashed lines, Introns); the thickness of the arrow indicates the relative abundance. The shaded bars above the arrows indicate the E3 proteins, which are named on the basis of their molecular masses.
Figure 3:
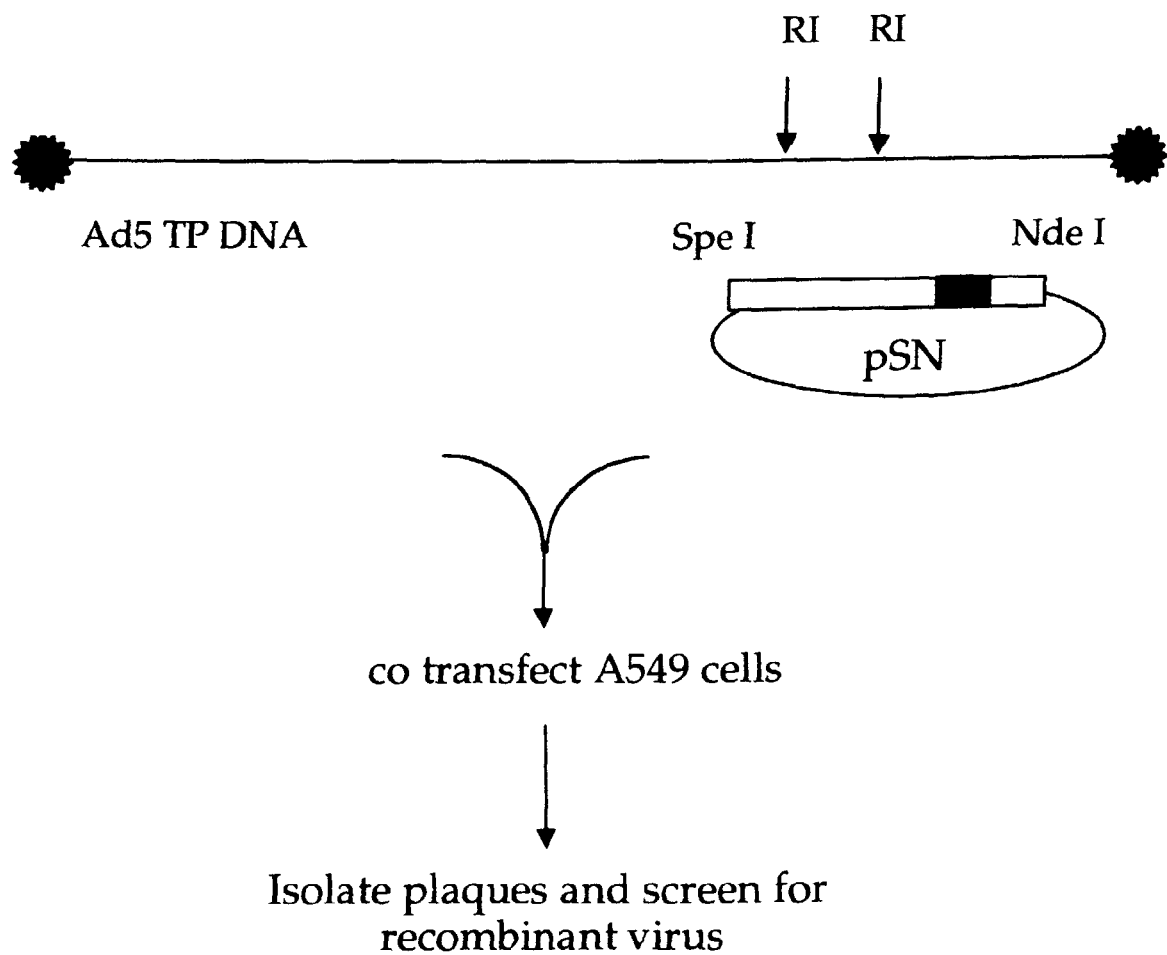
FIG. 3 shows the production of recombinant virus using pSN with the desired mutation and Ad5 TP-DNA. The same strategy can also be used for the pG-based plasmids containing mutations.
Figure 4:
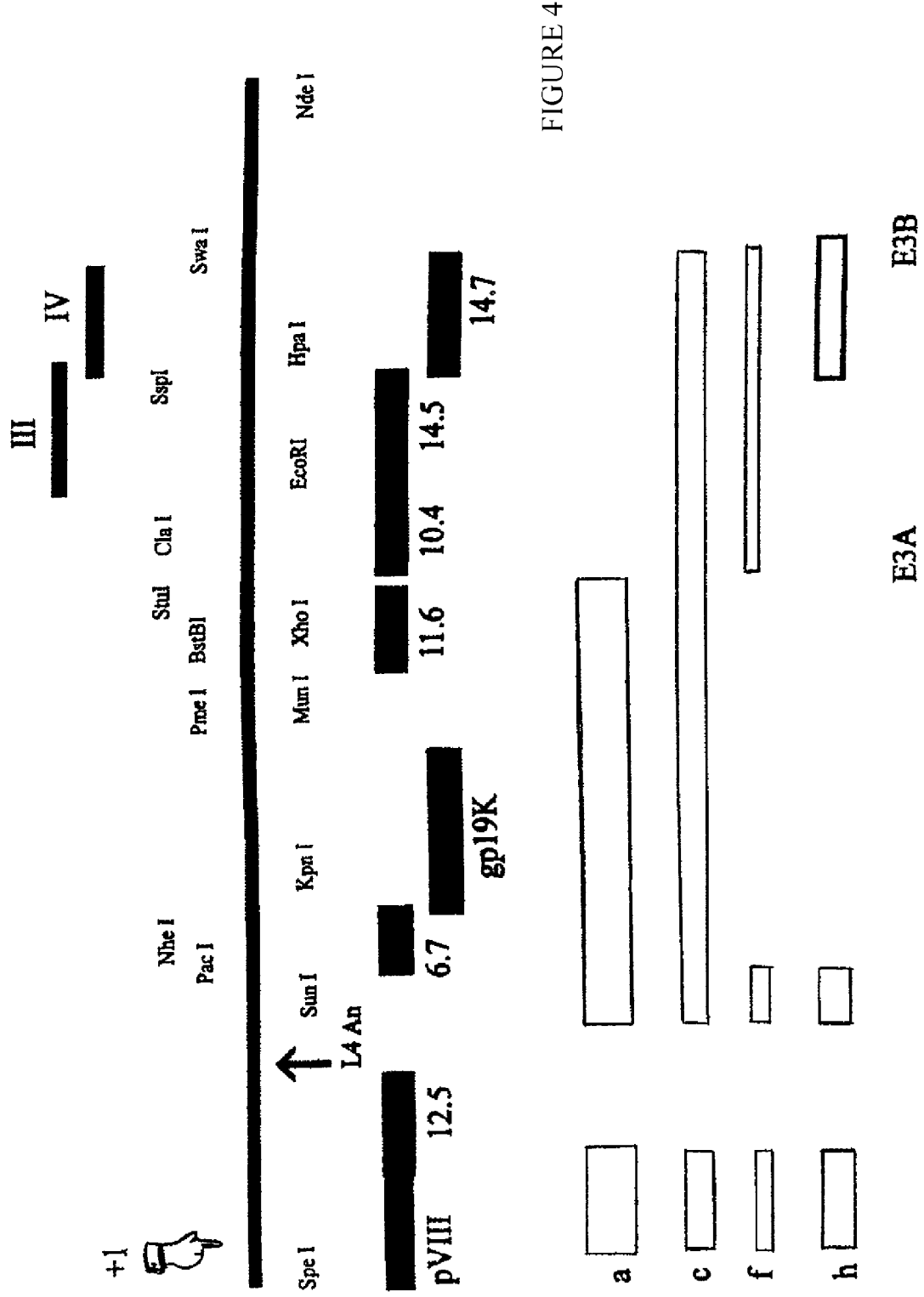
FIG. 4 shows the restriction map of the E3 region of the adenovirus E3SV. The open rectangles (a, c, f, and h) represent mRNAs (see FIG. 1).
Figure 5:
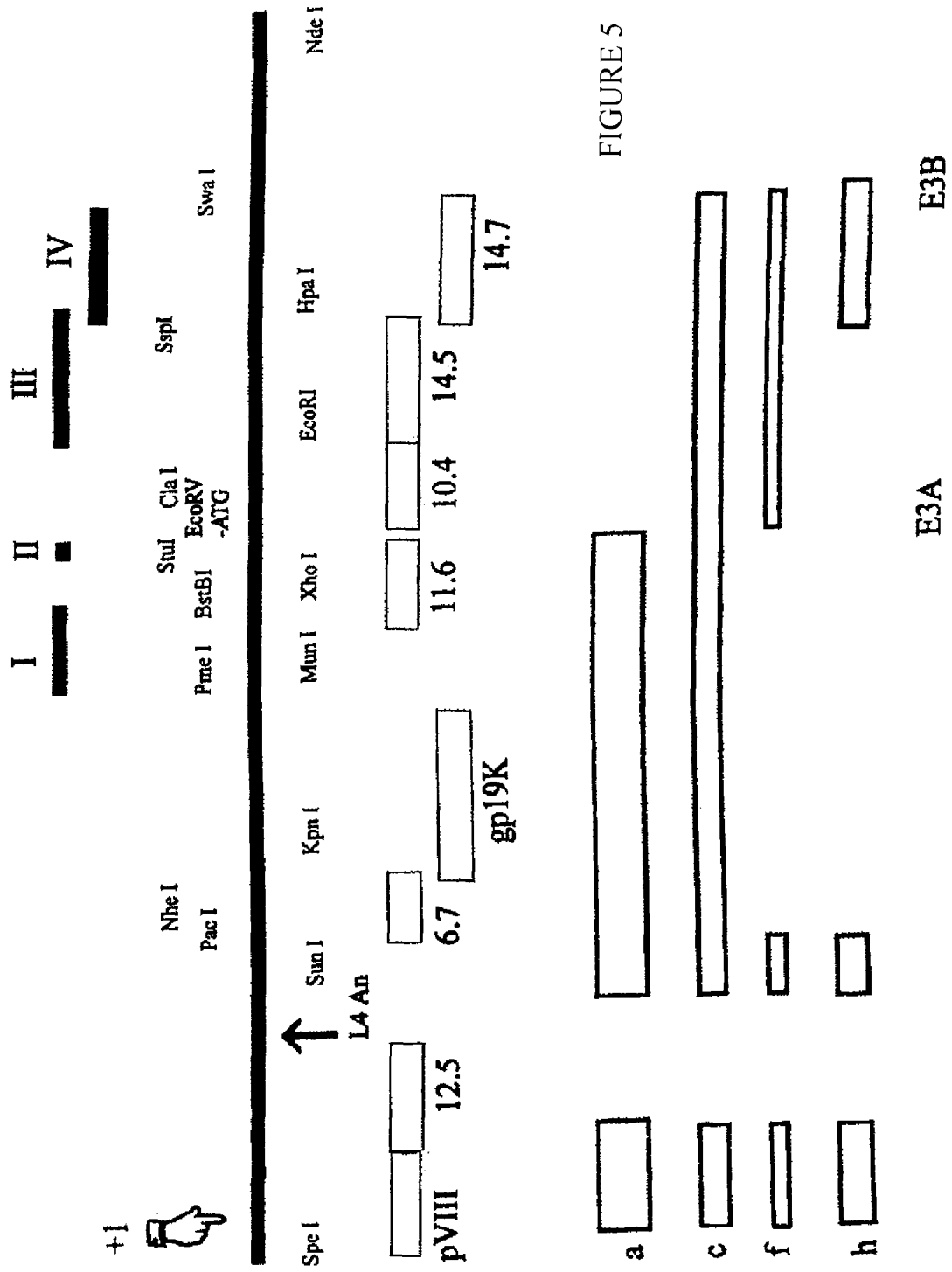
FIG. 5 shows the restriction map of the E3 region of the adenovirus E3SV+V. The open rectangles (a, c, f, and h) represent mRNAs(see FIG. 1).
Figure 6:
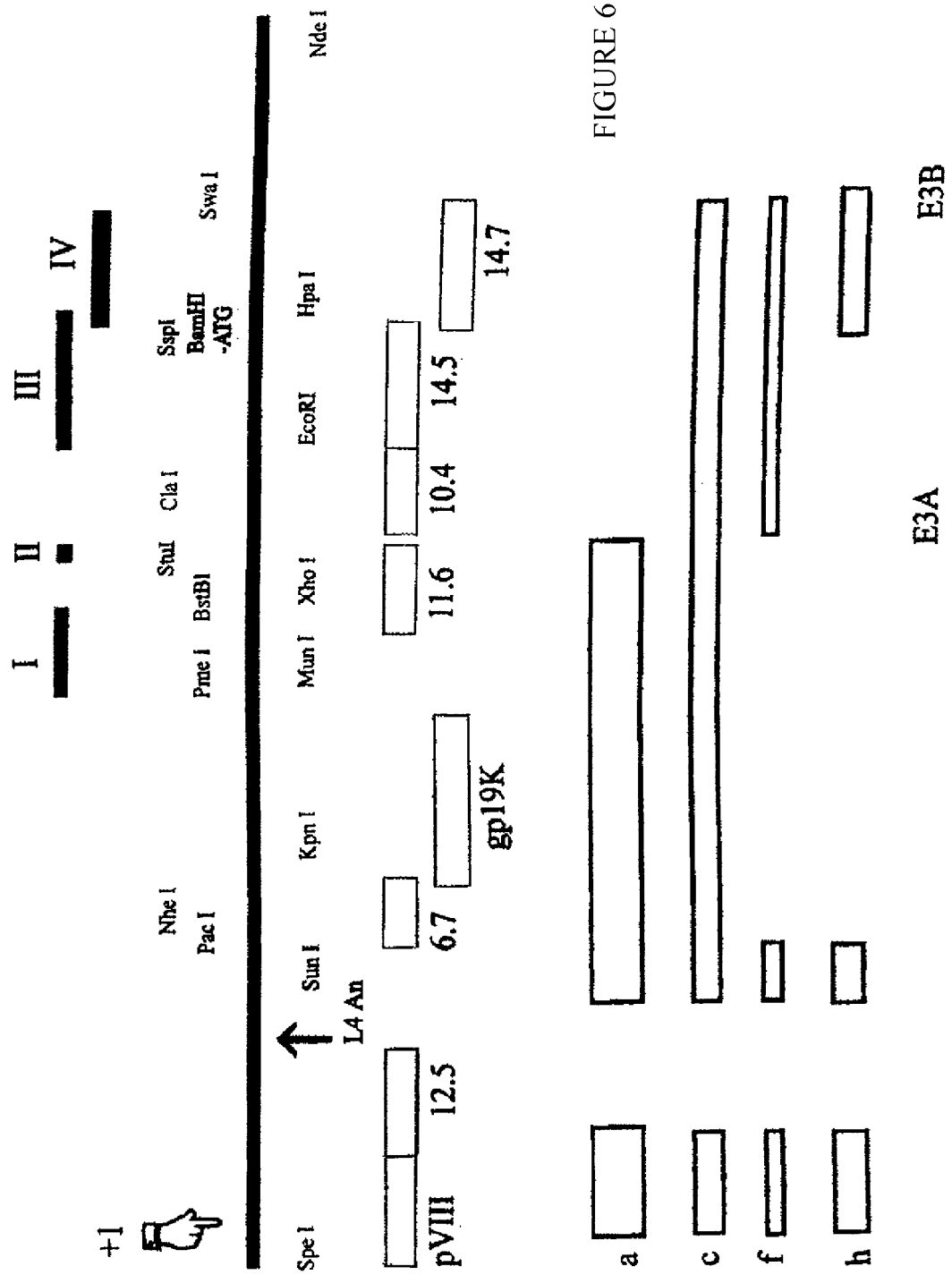
FIG. 6 shows the restriction map of the E3 region of the adenovirus E3SV+B. The open rectangles (a, c, f, and h) represent mRNAs(see FIG. 1).
Figure 40:
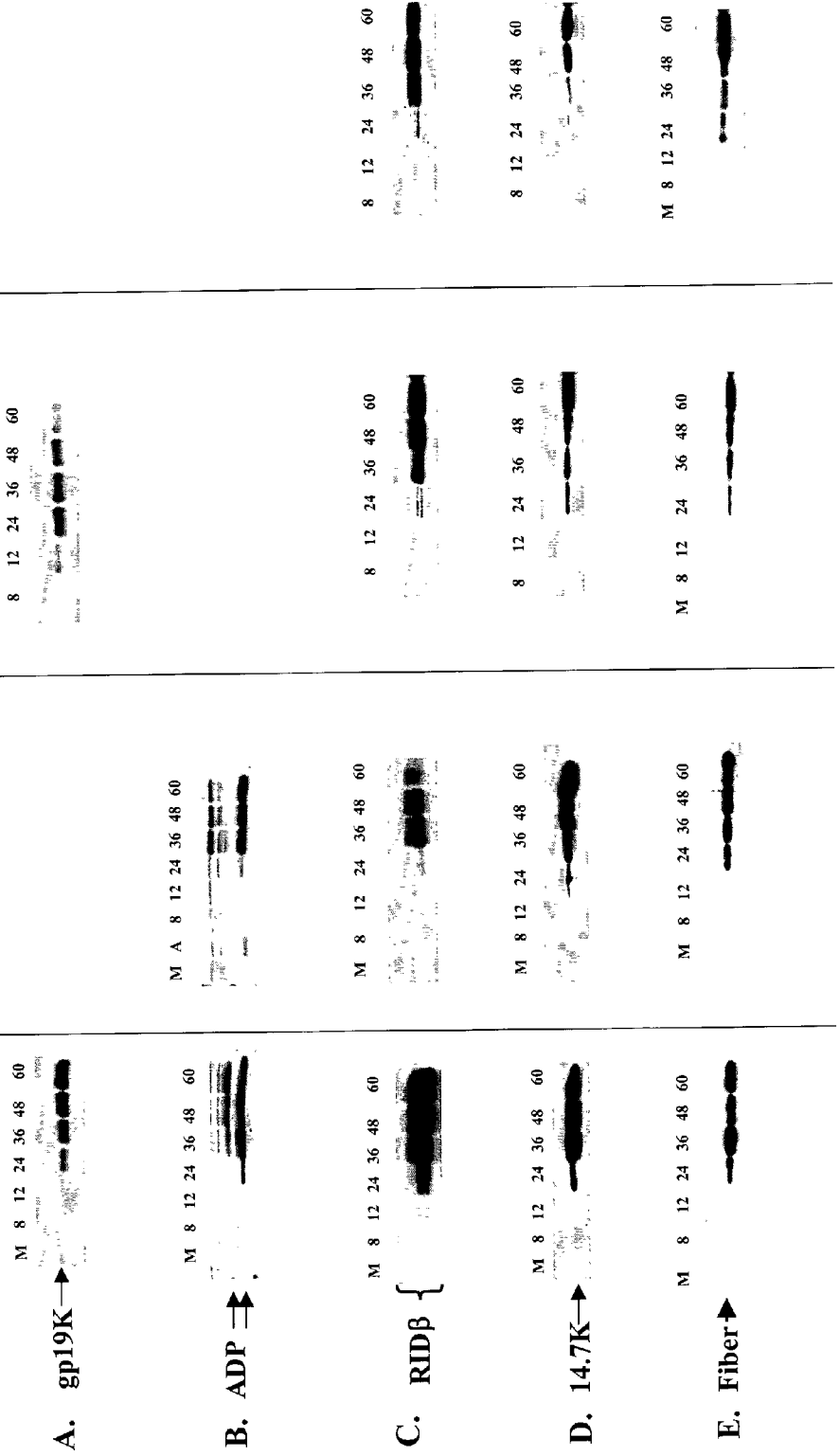

FIG. 40 shows Western blot analysis of Ad5 E3 endogenous proteins. Western blot analysis was performed on protein extracts from Ad5, ONYX-371, -320, -and -372-infected cells. Analysis in this figure is for the remaining endogenous E3 proteins (see FIG. 1 for map) that are produced. The numbers above each blot indicate the time post infection. The "M" and "A" indicate mock-infected and Ad5-infected cells, respectively, were harvested at 24 hours post infection. The fiber protein is synthesized from the downstream L5 region and is shown to indicate effects of heterologous gene insertion in the region immediately downstream of the E3 region.

FIG. 41 shows a time course of A549 infected cells at 10 pfu/cell with the indicated virus. Photographs were taken at 24, 48, and 60 hours post infection.

Figure 42:
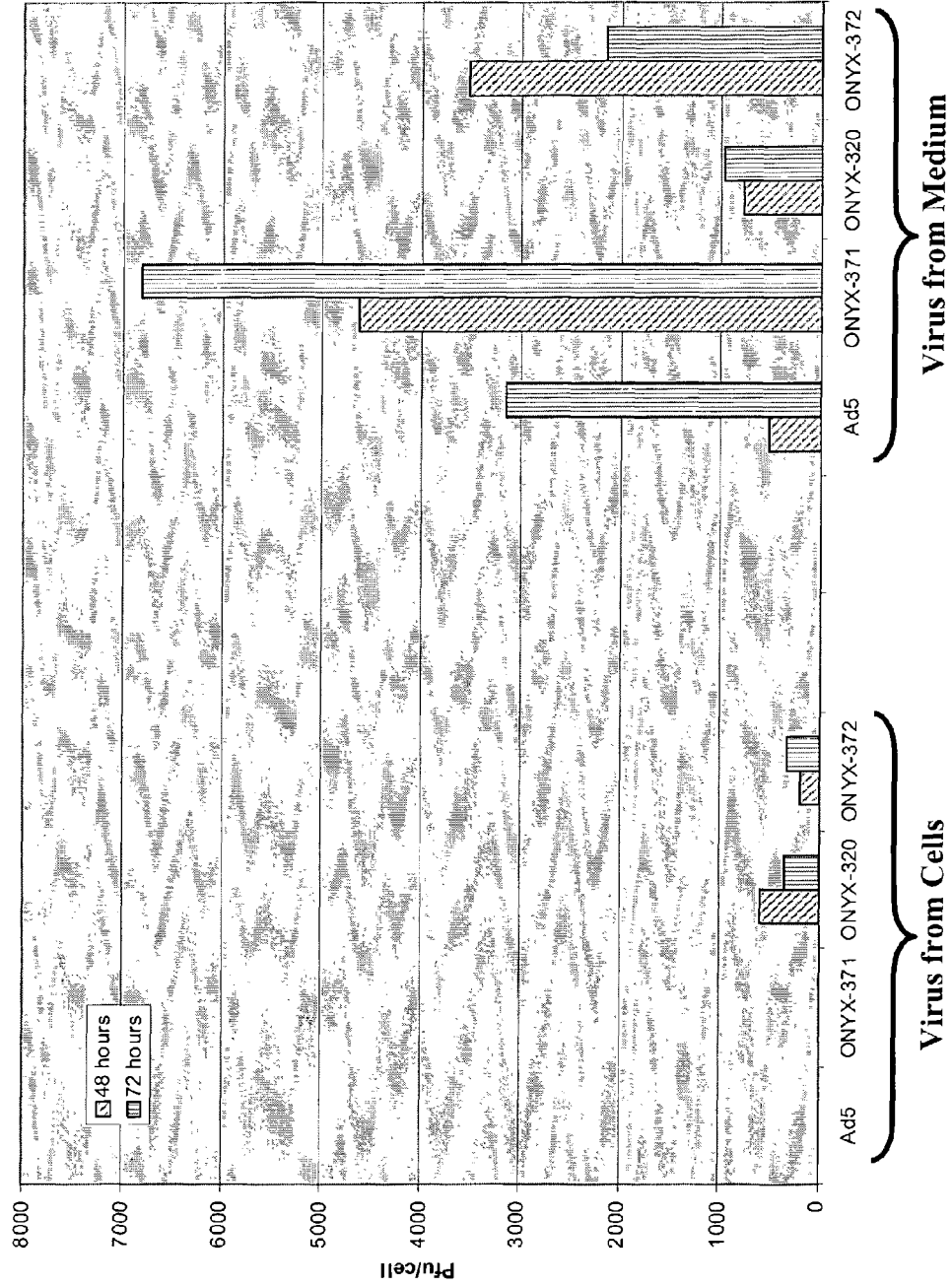

FIG. 42 shows a viral burst assay of A549 cells that were infected with the indicated viruses. At 48 or 72 hours post infection, the cells and the culture supernatent were harvested separately and titered as described below.

DETAILED DESCRIPTION OF THE INVENTION

All publications, including patents and patent applications, mentioned in this specification are herein incorporated by reference to the same extent as if each individual publication was specifically and individually indicated to be incorporated by reference in its entirety.

Definitions

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual, 2nd. edition* (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

Those skilled in the art will also recognize publications that facilitate genetic engineering of the invention adenovirus to produce mutants in the E3 region. Such would include McGrory, W. J. et al., (1988) Virology, vol. 177, pp. 437-444 who describe insertion of DNA into the E1 region; Hanke, T., et al. (1990) Virology, vol. 177, pp. 437-444 and Bett, A. J. et al. (1993) J. Virol. vol. 67, pp. 5911-5921 who describe insertion of foreign DNA into the E3 region; and Bett, A. J. et al. (1994) Proc. Natl. Acad. Sci. vol. 91, pages 8802-8806, who describe insertion of DNA into the E1 and E3 regions. See also, Hermiston, T. et al., Methods in Molecular Medicine: Adenovirus Methods and Protocols, W. S. M. Wold, ed, Humana Press, 1999.

In the formulae representing selected specific embodiments of the present invention, the amino- and carboxy-terminal groups, although often not specifically shown, will be understood to be in the form they would assume at physiological pH values, unless otherwise specified. Thus, the N-terminal $H_2^+$ and C-terminal-$O^-$ at physiological pH are understood to be present though not necessarily specified and shown, either in specific examples or in generic formulas. In the polypeptide notation used herein, the left hand end of the molecule is the amino terminal end and the right hand end is the carboxy-terminal end, in accordance with standard usage and convention. Of course, the basic and acid addition salts including those which are formed at non-physiological ph values are also included in the compounds of the invention. The amino acid residues described herein are preferably in the "L" isomeric form. Stereoisomers (e.g., D-amino acids) of the twenty conventional amino acids, unnatural amino acids such as a,a-distributed amino acids, N-alkyl amino acids, lactic acid, and other unconventional amino acids may also be suitable components for polypeptides of the present invention, as long as the desired functional property is retained by the polypeptide. For the peptides shown, each encoded residue where appropriate is represented by a three letter designation, corresponding to the trivial name of the conventional amino acid, in keeping with standard polypeptide nomenclature (described in *J. Biol. Chem.* 243:3552-59

(1969) and adopted at 37 CFR §1.822(b)(2)). Free functional groups, including those at the carboxy- or amino-terminus, referred to as noninterfering substituents, can also be modified by amidation, acylation or other substitution, which can, for example, change the solubility of the compounds without affecting their activity.

As employed throughout the disclosure, the following terms, unless otherwise indicated, shall be understood to have the following meanings:

The term "isolated protein" referred to herein means a protein of CDNA, recombinant RNA, or synthetic origin or some combination thereof, which by virtue of its origin the "isolated protein" (1) is not associated with proteins found in nature, (2) is free of other proteins from the same source, e.g. free of human proteins, (3) is expressed by a cell from a different species, or (4) does not occur in nature.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "adenovirus" as referred to herein indicates over 40 adenoviral subtypes isolated from humans, and as many from other mammals and birds. See, Strauss, "Adenovirus infections in humans," in *The Adenoviruses*, Ginsberg, ed., Plenum Press, New York, N.Y., pp. 451-596 (1984). The term preferably applies to two human serotypes, Ad2 and Ad5.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like known in the art.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, b-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence that is compared to some other sequence. Gaps (in either of the two sequences) are permitted to maximize matching; gap lengths of 15 bases or less are usually used, 6 bases or less are preferred with 2 bases or less more preferred.

The term "selectively hybridize" referred to herein means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as may be used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

The term "polypeptide fragment" or "peptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically 8-10 amino acids long, preferably at least 10-20 amino acids long, and even more preferably 20-70 amino acids long.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference.

The production of proteins from cloned genes by genetic engineering is well known. See, e.g. U.S. Pat. No. 4,761,371 to Bell et al. at column 6, line 3 to column 9, line 65. The discussion which follows is accordingly intended as an overview of this field, and is not intended to reflect the full state of the art.

DNA which encodes proteins that may be inserted into the adenoviral constructs of the instant invention in the E3 region can be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from known gene sequence information. Probes may be labeled with a detectable group such as a fluorescent group, a radioactive atom or a chemiluminescent group in accordance with known procedures and used in conventional hybridization assays, as described in greater detail in the Examples below.

In the alternative, a gene sequence may be recovered by use of the polymerase chain reaction (PCR) procedure. See U.S. Pat. No. 4,683,195 to Mullis et al. and U.S. Pat. No. 4,683,202 to Mullis.

A vector is a replicable DNA construct. Preferred embodiment vectors described herein to realize the adenovirus E3 vectors, including viruses, are based on the pGEM vector series of Promega Corporation. Vectors may be used either to amplify DNA encoding a desired protein and/or to express DNA which encodes the protein.

An expression vector is a replicable DNA construct in which a DNA sequence encoding a protein of interest is operably linked to suitable control sequences capable of affecting the expression of the protein in a suitable host. The need for such control sequences will vary depending upon the host selected and the transformation method chosen. Generally, control sequences include a transcriptional promoter, an enhancer, an optional operator sequence to control transcription, a sequence encoding suitable mRNA ribosomal binding sites, alternative splicing sites, translational sequences, and sequences which control the termination of transcription and translation. The phrase "endogenous adenoviral transcriptional regulatory sequences," is meant herein to refer to at least one of these control sequences for expressing heterologous genes in the invention adenoviral vectors.

Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the vectors constructed using recombinant DNA techniques.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame. A preferred embodiment promoter of the instant invention in those instances where certain E3 region DNA is deleted, preferably the E3b region, and heterologous DNA substituted therein, is an adenoviral endogenous promoter which is operably linked to a negative selection gene.

Suitable host cells include prokaryotes, yeast cells, or higher eukaryotic cells. Prokaryotes include gram negative or gram positive organisms, for example *Escherichia coli* (*E. coli*) or *Bacilli*. Higher eukaryotic cells include established cell lines of mammalian origin as described below. Exemplary host cells are DH5a, *E. coli* W3110 (ATCC 27,325), *E coli* B, *E. coli* X1776 (ATCC 31,537) and *E. coli* 294 (ATCC 31,446).

A broad variety of suitable microbial vectors are available, and may have applications in constructing the instant adenoviral vectors. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., Gene 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., Nature 275, 615 (1978); and Goeddel et al., Nucleic Acids Res. 8, 4057 (1980) and EPO Application Publication Number 36,776) and the tac promoter (H. De Boer et al., Proc. Natl. Acad. Sci. USA 80, 21 (1983)). While these are commonly used, other microbial promoters are suitable. Details concerning nucleotide sequences of many promoters have been published, enabling a skilled worker to operably ligate them to DNA in plasmid or viral vectors (Siebenlist et al., Cell 20, 269, 1980)).

Cultures of cells derived from multicellular organisms are a desirable host for recombinant protein synthesis. In principal, any higher eukaryotic cell culture is workable, whether from vertebrate or invertebrate culture. However, mammalian cells are preferred. Propagation of such cells in cell culture has become a routine procedure. See Tissue Culture, Academic Press, Kruse and Paterson, editors (1973). Examples of useful host cell lines are VERO and HeLa cells, Chinese hamster ovary (CHO) cell lines, and FL5.12, WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

The transcriptional and translational control sequences in expression vectors used to produce the invention adenoviral vectors, and that are used in transforming vertebrate cells are often provided by viral sources, including adenovirus. A variety of viral and mammalian constitutive promoter elements can be used. See, Mittal et al., (1993) Virus Research, vol. 28, pp. 67-90. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., Nature 273, 113 (1978).

With respect to the expression of a heterologous gene(s) from adenoviral vectors, a preferred embodiment of transcriptional control sequences is an endogenous adenoviral polynucleotide sequence which increases transcription of an operably-linked heterologous gene. Such would include at least an operably portion of an adenoviral promoter and/or a enhancer.

Construction of Adenovirus E3 Mutants

Methods for the construction of adenoviral mutants are generally known in the art. See, Mittal, S. K., Virus Res.,1993, vol: 28, pages 67-90; and Hermiston, T. et al., Methods in Molecular Medicine: Adenovirus Methods and Protocols, W. S. M. Wold, ed, Humana Press, 1999. Further, the adenovirus 5 genome is registered as Genbank accession #M73260, and the virus is available from the American Type Culture Collection, Rockville, Md., U.S.A., under accession number VR-5.

Generally, adenovirus vector construction involves an initial deletion or modification of a desired region of the adenoviral genome, preferably the Ad5 genome, in a plasmid cassette using standard techniques.

The adenoviral DNA, or a fragment thereof, present in pNB and which corresponds to the E3 region of the virus is subsequently cloned into another plasmid which may also be pGEM5zf+. For example, the Spe1-Nde1 fragment, corresponding to bases 27082-31089, of the Ad5 genome can be excised from pNB and cloned into the Spe1 and Nde1 sites in the multiple cloning site (MCS) of pGEM5zf+. This vector is termed pSN, and the adeno DNA present therein, bases 27082-31089, may be used to engineer the desired restriction sites into the E3 region to yield the appropriate E3 vectors, plasmids and viruses, discussed more below.

Certain of the materials and methods used to construct adenovirus mutants are described by Hanke, T., et. al. (1990) Virology, vol. 177, pages 437-444, and Bett, A. J., et. al., (993) J. Virol. vol. 67, pages 5911-5921, and in PCT/CA96/00375. Microbix Biosystems, Inc., located at 341 Bering Avenue, Toronto, Ontario Canada, sells many of the materials used to construct adenovirus mutants, and provides Product Information Sheets on how to make them. See also, Hermiston, T. et al., Methods in Molecular Medicine: Adenovirus Methods and Protocols, W. S. Wold, ed, Humana Press, 1999.

It is noteworthy that while the instant invention is described in terms of adenovirus type 5, it may be practiced with other similar adenovirus serotypes. The general organization of the adenoviral genome is conserved among serotypes, and specific functions are similarly situated.

The mutations in the E3 region described herein may be incorporated into adenoviral mutants that have mutations outside the E3 region. Preferably such mutations would be in the EB and/or E1A and/or the E4 or f6 regions of the adenoviral genome. In the case of E1B mutations, the preferred mutations confer on adenovirus the ability to preferentially replicate in neoplastic cells compared to normal cells, wherein the neoplastic cells are functionally defective in the tumor suppressor, p53. Such mutations typically occur in the E1B region that encodes the 55 kD protein. Defective p53 can arise in numerous ways, including a defect in those proteins that interact with p53; that is, a defect in the p53 pathway that renders p53 functionally inactive. See, U.S. Pat. No. 5,677,178. Thus, the E3 mutations described herein could be combined with the E1B deletion in the adenovirus dl1520. This virus is described by Barker and Berk (1987) *Virology* 156: 107.

In the case of E1A mutations, the preferred mutations confer on adenovirus the ability to preferentially replicate in neoplastic cells compared to normal cells, wherein the neoplastic cells are functionally defective in the retinoblastoma tumor suppressor gene product, or p105 Rb. Such inactivating mutations in Ad5, typically occur in amino acids 30-85 in the E1A CR1 domain, or nucleotide positions 697-790, and/or the CR2 domain, amino acids 120-139, nucleotide positions 920-967, which are involved in binding the p105 Rb protein. Preferably, the CR3 domain of the adenoviral genome (spanning amino acids 150-188) remains and is expressed as a truncated p289R polypeptide and is functional in transactivation of adenoviral early genes. Defective pRb can arise in numerous ways, including a defect in those proteins that interact with pRb; that is, a defect in the pRb pathway that renders pRb functionally inactive. See, U.S. Pat. No. 5,677,178. Thus, the E3 mutations described herein could be combined with the E1A deletion in the adenovirus Ad5 NT dl1010.

Another aspect of the instant invention is the incorporation of foreign, or heterologous, genes into the E1B, E1A, or E4 or f6 regions of an E3 mutant virus described herein. Thus, such viruses would contain heterologous genes in the E3 region, and optionally in E1B, E1A or E4 or f6.

Examples of heterologous genes, or fragments thereof that encode biologically active peptides, include those that encode immunomodulatory proteins, and prodrug activators (i.e. cytosine deaminase, thymidine kinase, U.S. Pat. Nos. 5,358,866, and 5,677,178). Examples of the former would include interleukin 2, U.S. Pat. Nos. 4,738,927 or 5,641,665; interleukin 7, U.S. Pat. Nos. 4,965,195 or 5,328,988; and interleukin 12, U.S. Pat. No. 5,457,038; tumor necrosis factor alpha, U.S. Pat. Nos. 4,677,063 or 5,773,582; interferon gamma, U.S. Pat. Nos. 4,727,138 or 4,762,791; or GM-CSF, U.S. Pat. Nos. 5,393,870 or 5,391,485. Additional immunomodulatory proteins further include macrophage inflammatory proteins, including MIP-3, (See, Well, T. N. and Peitsch, M C. J. Leukoc. Biol vol 61 (5): pages 545-50, 1997), and cell suicide, or apoptosis inducing proteins, including BAD and BAX. See, Yang, E., et al. Cell, vol 80, pages 285-291 (1995); and Sandeep, R., etal Cell, vol. 91, pages 231-241 (1997). Monocyte chemotatic protein (MCP-3 alpha) may also be used. A preferred embodiment of a heterologous gene is a chimeric gene consisting of a gene that encodes a protein that traverses cell membranes, for example, VP22 or TAT, fused to a gene that encodes a protein that is preferably toxic to cancer but not normal cells.

As mentioned above, the initial step in the construction of recombinant adenoviral vectors having novel restriction sites in the E3 region that facilitate partial or total deletion of the E3 region genes, or select genes contained therein, is to make mutations in the adenoviral genome in a plasmid cassette using well established techniques of molecular biology, or modifications these techniques, referred to herein. The following restrictions sites were engineered into the E3 region of adenovirus 5: PacI, ClaI, PmeI, SwaI, BamHI, BstBI, SspI, NheI, and StuI and EcoRV. Their relative positions in the E3 region are shown in FIGS. 4-7. The restriction sites were positioned so as not to knowingly disrupt critical splicing and polyadenylation signals. Another consideration was the coding sequence of proteins in the E3 region; in most cases, the mutations that were made to add the novel restriction sites did not result in a change in the coding sequence; however, when amino acid changes were made, they were conservative in nature.

Thus, it is important to point out a key advantage of such adenoviruses that have inserted in the E3 region a heterologous gene or genes, which is that such gene(s) will preferably exhibit an expression pattern, both in terms of timing and degree of expression, similar to the endogenous adenoviral gene(s) that it replaces which results from such heterologous gene(s) being operably linked to endogenous adenoviral transcriptional control sequences.

An embodiment of the invention is adenoviral vectors that have two heterologous genes substituted for E3 genes, which E3 genes are normally expressed early and late, thus imparting this expression pattern to the two heterologous genes. It is important to point out that more than two heterologous genes could be used. Since the expression of E3 region genes vary throughout the course of the infection in a replicating virus [Wold, W. S., A. E. Tollefson, and T. W. Hermiston. Curr Top Microbiol Immunol, 1995. 199((Pt 1)): p. 237-74] this creates an opportunity for therapeutic gene(s) to be engineered to specific levels or times in the viral life cycle to maximize their therapeutic benefit.

Examples of heterologous genes include prostate specific antigen promoter, (PCT/US95/14461), and negative selection genes including cytosine deaminase, and thymidine kinase. Regarding cytosine deaminase, see, U.S. Pat. Nos. 5,358,866, and 5,677,178.

Expression cassettes may also be used to produce the invention adenoviral vectors. For example, an HSV tk gene cassette may be operably linked downstream of an endogenous E3 promoter. Frequently, it may be desirable to delete a nonessential portion of the E3 region (i.e., for viral replication and packaging) of the adenoviral genome to accommodate the negative selection cassette; thus a substantial portion of the E3 gene region may be deleted and replaced with a negative selection cassette such as an HSV tk gene operably linked to either an E3 promoter, or suitable promoter/enhancer. Alternatively, a negative selection gene may be operably linked to an adenovirus late region promoter to afford efficient expression of the negative selection gene product in cells expressing a replication phenotype characterized by transcription from late gene promoters.

Expression of the HSV tk gene in a cell is not directly toxic to the cell unless the cell is exposed to a negative selection agent such as gancyclovir or FIAU. Infected cells expressing a replication phenotype wherein a negative selection gene is substantially expressed may produce essentially no additional cytotoxicity until the negative selection agent (e.g., gancyclovir) is administered in an effective selective dosage, at which time the infected cells expressing the tk gene will be selectively ablated; thus negative selection can be used for enhanced cytopathic killing and/or to damp out further viral replication by killing cells exhibiting a replicative phenotype.

A preferred embodiment is an HSV tk gene cassette (Zjilstra et al. (1989) *Nature* 342: 435; Mansour et al. (1988) *Nature* 336: 348; Johnson et al. (1989) *Science* 245: 1234: Adair et al. (1989) *Proc. Natl. Acad. Sci (U.S.A.)* 86: 4574; Capecchi, M. (1989) *Science* 244:1288, incorporated herein by reference) operably linked to an appropriate endogenous adenoviral promoter and/or enhancer with a polyadenylation site to form a tk expression cassette. The tk expression cassette (or other negative selection expression cassette) is inserted into the adenoviral genome, for example, as a replacement for a substantial deletion of the E3 region.

The adenoviral vectors of the instant invention that encode a desired protein can be used for transformation of a suitable mammalian host cell. Transformation can be by any known method for introducing polynucleotides into a host cell, including, for example packaging the polynucleotide in a virus and transducing a host cell with the virus or by transfection procedures known in the art, as exemplified by U.S. Pat. Nos. 4,399,216, 4,912,040, 4,740,461, and 4,959,455. The transformation procedure used depends upon the host to be transformed. Methods for introduction of heterologous polynucleotides into mammalian cells are known in the art and include dextran-mediated transfection, calcium phosphate precipitation, polybrene mediated transfection, electroporation, encapsulation of the polynucleotide(s) in liposomes, and direct microinjection of the DNA into nuclei.

Therapeutic Methods

Therapy of disease, preferably neoplastic disease, may be afforded by administering to a patient a composition comprising adenoviruses of the invention, and further comprising a negative selection gene. Examples of the latter would include cytosine deaminase and thymidine kinase.

Various human neoplasms may be treated with the invention adenoviral constructs, particularly in those instances where the E3 region of the virus encodes a protein useful for gene therapy of disease. An example would be a cytokine, preferably an interleukin. For example, but not by way of limitation, a human patient or nonhuman mammal having a bronchogenic carcinoma, nasopharyngeal carcinoma, laryngeal carcinoma, small cell and non-small cell lung carcinoma, lung adenocarcinoma, hepatocarcinoma, pancreatic carcinoma, bladder carcinoma, colon carcinoma, breast carcinoma, cervical carcinoma, ovarian carcinoma, or lymphocytic leukemias may be treated by administering an effective antineoplastic dosage of an appropriate adenovirus. Suspensions of infectious adenovirus particles may be applied to neoplastic tissue by various routes, including intravenous, intraperitoneal, intramuscular, subdermal, and topical. An adenovirus suspension containing about $10^3$ to $10^{12}$ or more virion particles per ml may be inhaled as a mist (e.g., for pulmonary delivery to treat bronchogenic carcinoma, small-cell lung carcinoma, non-small cell lung carcinoma, lung adenocarcinoma, or laryngeal cancer) or swabbed directly on a tumor site for treating a tumor (e.g., bronchogenic carcinoma, nasopharyngeal carcinoma, laryngeal carcinoma, cervical carcinoma) or may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g., a breast tumor), enema (e.g., colon cancer), or catheter (e.g., bladder cancer).

The invention adenovirus mutants may be further evaluated by their capacity to reduce tumorigenesis or neoplastic cell burden in nu/nu mice harboring a transplant of neoplastic cells, as compared to untreated mice harboring an equivalent transplant of the neoplastic cells.

Adenoviral therapy using the instant invention E3 viruses may be combined with other antineoplastic protocols, such as conventional chemotherapy. Also, in the event that the instant E3 adenoviral vectors, or viruses elicit an immune response that dampens their effect in a host animal, they can be administered with an appropriate immunosuppressive drug.

Propagation of Mutant Adenovirus

Adenoviral mutants of the invention typically are propagated as viral stocks in a cell line (e.g., the 293 cell line ATCC # CRL 1573, American Type Culture Collection, Rockville, Md.; Graham et al. (1977) *J. Gen. Virol.* 36: 59, or A549 cells) that can provide certain desired viral functions, if needed, in trans to support replication and formation of infectious mutant virions.

Formulations

Adenovirus E3 mutants may be formulated for therapeutic and diagnostic administration to a patient. For therapeutic or prophylactic uses, a sterile composition containing a pharmacologically effective dosage of one or more species of adenovirus mutant is administered to a human patient or veterinary non-human patient for treatment, for example, of a neoplastic condition. Generally, the composition will comprise about $10^3$ to $10^{15}$ or more adenovirus particles in an aqueous suspension. A pharmaceutically acceptable carrier or excipient is often employed in such sterile compositions. A variety of aqueous solutions can be used, e.g., water, buffered water, 0.4% saline, 0.3% glycine and the like. These solutions are sterile and generally free of particulate matter other than the desired adenoviral virions. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. Excipients which enhance infection of cells by adenovirus may be included.

Adenoviruses of the invention, or the DNA contained therein, may be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang (1985) *J. Cell Biol.* 101: 582; Lasic DD (1992) *Nature* 355: 279; *Novel Drug Delivery* (eds. Prescott L F and Nimmo W S: Wiley, New York, 1989); Reddy et al. (1992) *J. Immunol.* 148: page 1585). Immunoliposomes comprising an antibody that binds specifically to a cancer cell antigen (e.g., CALLA, CEA) present on the cancer cells of the individual may be used to target virions, or virion DNA to those cells.

The compositions containing the present adenoviruses or cocktails thereof can be administered for prophylactic and/or therapeutic treatments of neoplastic disease. In therapeutic application, compositions are administered to a patient already affected by the particular neoplastic disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

In prophylactic applications, compositions containing the invention adenoviruses, or cocktails thereof, are administered to a patient not presently in a neoplastic disease state to enhance the patient's resistance to recurrence of a neoplasm or to prolong remission time. Such an amount is defined to be a "prophylactically effective dose." In this use, the precise amounts again depend upon the patient's state of health and general level of immunity.

Single or multiple administrations of the compositions can be carried out with dose levels and pattern being selected by the treating physician. In any event, the pharmaceutical formulations should provide a quantity of the antineoplastic adenoviruses of this invention sufficient to effectively treat the patient.

Antineoplastic adenoviral therapy of the present invention may be combined with other antineoplastic protocols, such as conventional chemotherapy.

Uses of the Invention

It will be apparent, based on the discussion above, that the adenoviral vectors/viruses described herein have multiple uses including applications in gene therapy. For example, in one embodiment of the invention, a gene that encodes a medically useful protein may be cloned into the E3 region of the instant invention virions, and the virions used directly in gene therapy protocols to treat disease. In another embodiment of the invention, discussed above, such E3 mutant virions may also have deletions/mutations in other regions of the adenoviral genome, including in the E1B region and have substituted therefore a gene with desirable properties. In either the E3 or E1B or other regions, such genes might encode cytokines, including the interleukins, cell cycle regulatory proteins, including p16, ras, or proteins that induce cellular suicide or apoptosis, prodrug activators, including cytosine deaminase or thymidine kinase. Further, tumor necrosis factor alpha, interferon gamma, and mip-3 may be utilized. Additionally, genes that encode anti-angiogenic factors could be used.

The instant adenoviral vectors may also be used to express proteins that are useful immunogens, or as a vaccine, and to transform cells which do not ordinarily express a particular protein to thereafter express this protein. Cells expressing these molecules are useful as intermediates for making cell membrane preparations useful for binding assays, which are in turn useful for drug screening.

The Examples which follow are illustrative of specific embodiments of the invention, and various uses thereof. They are set forth for explanatory purposes only, and are not to be taken as limiting the invention.

EXAMPLES

Example 1

General Methods and Working Vectors

Methods for the construction and propagation of human adenovirus vectors are known in the art and will be understood to be applied in the Example presented below by the skilled practitioner of the art. Such would include the work of Hitt, M., et al Construction and propagation of human adenovirus vectors. In: Cell Biology: a Laboratory Handbook; J. Celis (Ed), Academic Press, N.Y. (1996); Graham, F. L. and Prevec, L. Adenovirus based expression vectors and recombinant vaccines. In: Vaccines: New Approaches to Immunological Problems. R. W. Ellis (ed) Butterworth. Pp. 363-390; and Graham, F. L. and Prevec, L. Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109-128, 1991. The materials and methods described in these articles were used below. See also, Hermiston, T. et al., Methods in Molecular Medicine: Adenovirus Methods and Protocols, W. S. M Wold, ed, Humana Press, 1999.

Adenoviral Vectors:

Vectors based on pGEM (Promega Corp.) were modified and used to clone, subclone, and mutagenize the appropriate E3 region of Ad5. This took advantage of the Ad5 existing restriction sites in and outside the E3 region, and these are shown in Table 1.

TABLE 1

| Restriction sites present in Ad5 | |
| --- | --- |
| NdeI | 19549 and 31089 |
| SpeI | 27082 |
| EcoRI | 27295 and 30049 |
| SunI | 28390 |
| EcoRV | 27295 |
| KpnI | 28787 |
| MunI | 29355 |
| NotI | 29510 |
| XhoI | 29791 |
| HpaI | 30569 |

The vector designated pSN was subcloned by inserting the fragment from Ad5 SpeI (27082) to NdeI (31089) into the SpeI and NdeI sites in the multiple cloning site (MCS) in pGEM5Zf.

The vector pGEM5 was further modified because it possesses 3 SspI sites (2199, 2384, 2408); SspI is one of the engineered sites in the E3 shuttle vector. By deleting the SspI sites in the vector, inserting genes into the E3 SspI site would be facilitated since it would not involve partial restriction digests. To delete the vector sites, the plasmid pGEM5 was cut with SspI and EcoRV (present in the MCS at base 51) and religated. Unfortunately, the SspI site at 2199 was not deleted and found in the resultant altered vectors. So the vector contains the deletion from SspI at 2384 to EcoRV at 51. The presence of this extra SspI site still requires partial restriction digestion when utilizing SspI in the E3 region, although the isolation of the correct fragment is simplified by the deletion of two of those sites. Note also that there is an SspI site in the E3 region at 30172; this resides in the same region that would be excised when the engineered SspI site is to be used. Thus, it is of no consequence. This altered pGEM vector was used as the vector to insert the SpeI to NdeI region of Ad5, and for subsequent manipulations in the E3 regions and is indicated by pG.

Example 2

Construction of E3 Shuttle Vectors

Figure 7:
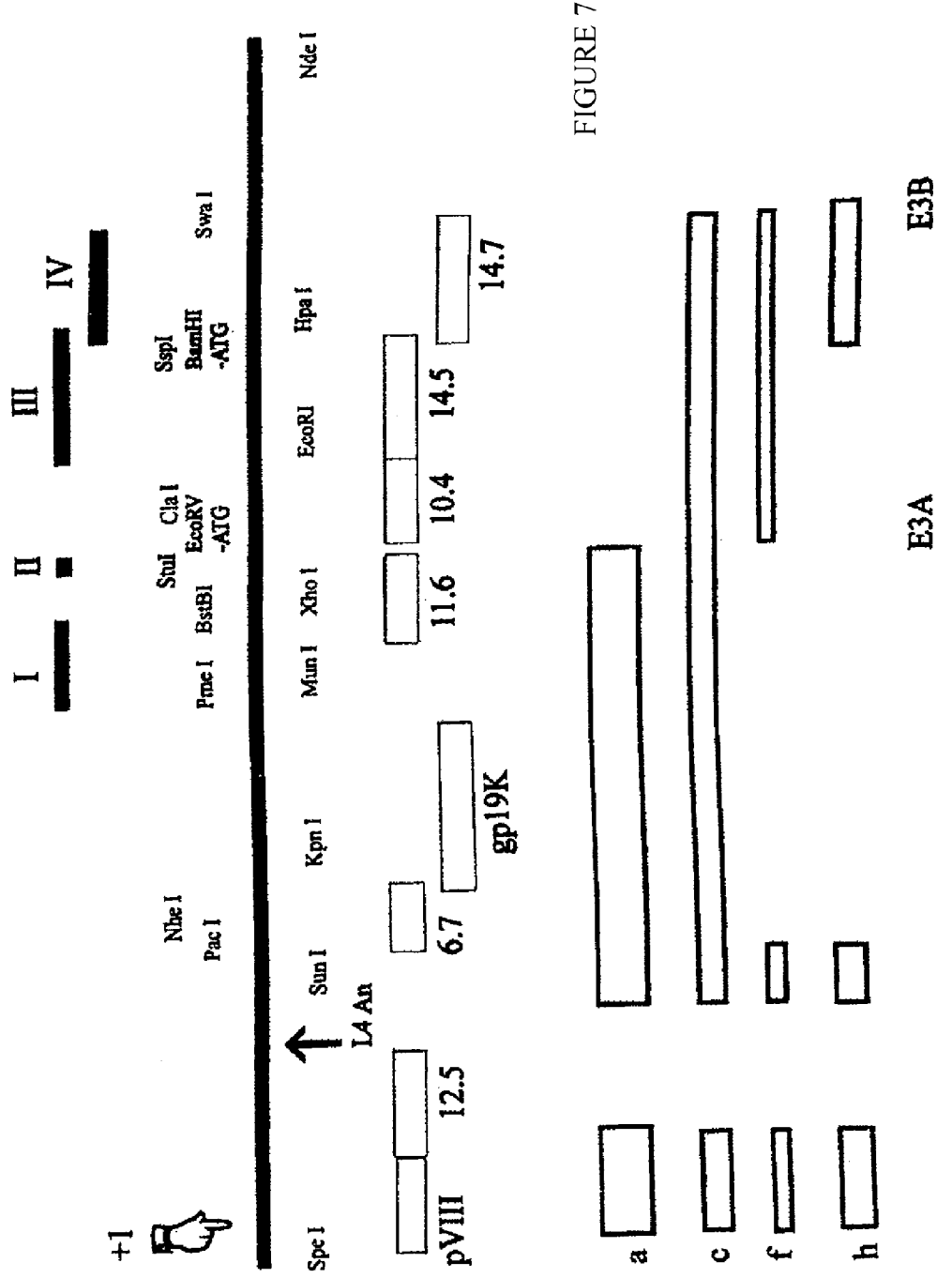
FIG. 7 shows the restriction map of the E3 region of the adenovirus E3SV+V+B. The open rectangles (a, c, f, and h) represent mRNAs (see FIG. 1).

Using the above vectors, the following restrictions sites were engineered into the E3 region of adenovirus 5: PacI, ClaI, PmeI, SwaI, BamHI, BstBI, SspI, NheI, and StuI and EcoRV. Their relative positions in the E3 region are shown in FIG. 7. The restriction sites were carefully positioned so as to not knowingly disrupt, or minimally disrupt, critical splicing and polyadenylation signals (see, FIG. 1). Also considered was the coding sequence of proteins; in most cases, the coded amino acid was not changed, and when changes had to be made, they were conservative.

Because of the position of the engineered sites, some mutations had to be performed sequentially. All of the oligonucleotide sequences used for mutagenesis and the exact location (position number in Ad5) are listed in the tables. All mutations were confirmed by restriction digests and all constructs were sequenced. Table 2 summarizes the restriction sites that were added to the E3 region of adenovirus 5.

TABLE 2

Restriction sites added to Ad5 E3 region.
Numbers refer to the Ad5 genome.

| | |
|---|---|
| PacI | 28497 |
| NheI | 28532 |
| PmeI | 29310 |
| BstBI | 29484 |
| StuI | 29718 |
| EcoRV* | 29781 |
| ClaI | 29862 |
| SspI | 30377 |
| BamHI** | 30467 |
| SwaI | 30830 |

*The start codon for 10.4 K was altered with this mutation
**The start codon for 14.7 K was altered with this mutation The sites PacI and ClaI were generated simultaneously by using mutant oligonucleotide PacC plus PacNC and ClaC plus ClaNC, respectively, using the Transformer Site-Directed Mutagenesis kit (Clontech #K1600-1) as directed by the manufacturer. The sites PmeI and SwaI were constructed separately using PmeC plus PmeNC and SwaC plus SwaNC, respectively, using the QuickChange Site-Directed Mutagenesis kit (Stratagene #200518) exactly as described by the manufacturer. The PmeI site was cloned into the PacI/ClaI-containing plasmid by inserting the PmeI-containing KpnI-XhoI (natural Ad5 sites) fragment into this plasmid. To this construct, the SwaI site was inserted using the HpaI to NdeI fragment. This resulting construct was called pG-PPCS and used for the next round of mutagenesis.

BamHI

All of the following mutations were created by PCR-based mutagenesis (See, Nucleic Acids Research 17: 5404; 1989, and U.S. Pat. No. 4,683,195 to Mullis et al. and U.S. Pat. No. 4,683,202 to Mullis) using Pfu polymerase, a high fidelity enzyme (Stratagene). All fragments generated by PCR were subsequently sequenced and determined to be error-free. This procedure employs two sequential PCR reactions and cutting the final product for insertion into a desired plasmid. Briefly; the technique employs two PCRs and three primers, one containing the mutation of interest. In the first reaction, the template and the two primers are used with one of the primers having the desired mutation. In the second reaction, the amplified product from the first reaction is used as a primer along with a third primer. The final product is digested and purified for insertion into a desired plasmid using standard techniques.

The BamHI site was generated with the oligonucleotides BamC and SwaNC in the first PCR and this product with PmeC in the second PCR, using the above-described plasmid pG-PPCS as the template. This fragment (the product of the second PCR) was digested with PmeI and SwaI to insert into pG-PPCS and this was termed pG-PPCS+B. It should be noted that this mutation also changes the 14.7K start codon to prevent premature initiation for any inserted gene at this site and that only two of the final four versions of the E3 shuttle vectors have the BamHI site. Vectors with this BamHI site are used when expression of 14.7K is not desired, or when 14.7 is replaced with a foreign gene.

BstBI, NheI, and StuI

The BstBI site was created using BstBC and SwaNC in the first PCR and PmeC plus the first product in the second PCR. The template used was pG-PPCS. The second PCR product was digested with MunI and SwaI and inserted into pG-PPCS, resulting in pG-PPBCS. To make a version of this vector that contained the BamHI site, the fragment from ClaI to HpaI with this site was inserted to make pG-PPBCS+B.

The NheI site was made with NheC and PmeNC in the first PCR and SunC and the first product in the second PCR, using pG-PPBCS+/−B as the templates in separate reactions. This fragment was digested with PacI and PmeI and inserted into the two versions of the above described constructs, pG-PP-BCS+/−B. This construct was called pG-PNPBCS+/−B. The StuI site was added by using StuC and SwaNC in the first reaction and PmeC and the first product in the second reaction, with pG-PPBCS+/−B as templates. The fragment was digested with MunI and SwaI and inserted into the two versions on the plasmid described in the previous paragraph (− or +BamHI) and these were called pG-PPBSCS or pG-PPB-SCS+B, respectively. The new StuI and NheI sites were added together by digesting the two plasmids with PacI and PmeI, and inserting the fragment which contained the NheI site (from pG-PNPBCS) into the StuI-containing plasmid (pG-PPBSCS). This was done in plasmids which did or did not have the BamHI site and the resulting plasmids were called pG-PNPBSCS+B and pG-PNPBSCS, respectively.

SspI and EcoRV

The last two mutations were made using both the above-described plasmids as templates, pG-PNPBSCS and pG-PNPBSCS+B. The SspI site was created with SspC and HpaNC primers in the first PCR and NheC and the product of the first PCR in the second PCR. This fragment was digested with XhoI and HpaI to insert into the parental plasmid, with or without the BamHI site. The EcoRV site was made using the EcoRVC and HpaNC primers in the first PCR and NheC and the first product in the second PCR. This fragment was cut with XhoI and HpaI to insert into the plasmids described in the above paragraph. The SspI and EcoRV sites were added together by cutting both BamHI-containing or BamHI-absent plasmids with PmeI and ClaI and inserting the EcoRV-containing fragment into the parental plasmids. Note the EcoRV site also changes the start codon for 10.4K to prevent premature initiation of genes inserted into the ClaI site at their 5' end. The ClaI site will be used, instead of the EcoRV site, for insertion of genes since the region with the EcoRV site is also involved in splicing. Deletion of this region might disrupt this event.

These final versions of the E3 shuttle vectors are depicted in FIGS. 4 through 7. These are called pGE3SV, pGE3SV+V, pGE3SV+B, and pGE3SV+V+B, the differences being the presence or absence of the EcoRV and BamHI sites. These shuttle vectors are used for construction of all subsequent plasmids, be they insertion of foreign genes or deletion of the Ad5 E3 genes. The oligonucleotides that were used to mutagenize the desired E3 region are shown in Table 3.

TABLE 3

Sequence of oligonucleotides used to mutagenize the E3 region of Adenovirus 5:

| Name | Sequence |
|---|---|
| SunC | CCTCTCCGAGCTCAGCTACTCCATCAG |
| PacC | GGAGGTGAGCTTAATTAACCCTTAGGG |
| PacNC | CCCTAAGGGTTAATTAAGCTCACCTCC |
| EcoRVC | GATTAAATGAGATATCATTCCTCGAG |
| HpaNC | GGCGGTGTCCGGTGGTATTACTGTCG |
| NheC | GGGTATTAGGCCAAAGGCGCAGCTAGCGTGGGG |
| StuC | CCAAACAATGAAGGCCTCCATAGATTGG |
| SspC | CAGCTACTTTAATATTACAGGAGGAG |
| BstBC | GCGACCCACCCTTTCGAACAGAGATGACCAAC |
| BamC | GGAGACGACTGACACCCTGGATCCAGAAATGG |
| ClaC | CACATCGATGTAGACTGC |
| ClaNC | GCAGTCTACATCGATGTG |
| PmeC | TAGAATAGGGTTTAAACCCCCCGG |
| PmeNC | CCGGGGGGTTTAACCCTATTCTA |
| SwaC | CTCAAAGATCTTATTCCATTTAAATAATAAA |
| SwaNC | TTTATTATTTAAATGGAATAAGATCTTTGAG |
| CD-PacC | GTGAGCTTAATTAAGGCTAGCAATGTCGAATAACGC |
| CD-SwaNC | GTGAGCATTTAAATCAGTCGTTCAACGTTTGTAATC |

All sequences are written 5' to 3'.
All changed bases are underlined.
Inserted bases are in bold.

Example 3

Construction of Virus Controls and Optional Plasmids for Virus Production

For controls, each of the E3 genes was deleted using the engineered sites. To do this, the shuttle plasmids were cut with the following pairs of enzymes, filled in using T4 DNA polymerase, and religated: PacI and PmeI, SunI and MunI, NheI and PmeI, BstBI and StuI (all in pG-E3SV), ClaI and SwaI (in pG-E3SV+V), ClaI and SspI (in pG-E3SV+V), and BamHI and SwaI (in pG-E3SV+B).

In addition to the pG plasmids referred to above that were used to generate the invention viruses, FIG. 2 shows another plasmid that could also be used, termed pNB. The pNB has two SpeI sites: one in the Ad5 insert and one in the pGEM5 MCS. The fragment from pNB which contained a portion of the MCS and NdeI 19549 to SpeI 27082 was inserted into the SpeI-cut pG-PPCS plasmid. The orientation was confirmed to be correct, and the resulting plasmid termed pNB-PPCS. All of the final versions of the E3 shuttle vectors were cloned into this plasmid by inserting the PacI to SwaI region of the pG plasmids into the larger pNB-PPCS. The resulting plasmids were designated pNB-E3SV, pNB-E3SV+V, pNB-E3SV+B, and pNB-E3SV+V+B, and could be used to produce viruses similar to those produced using the pG family.

Example 4

Construction of CD Plasmids

To test the shuttle vector system for its therapeutic use, the E. coli gene cytosine deaminase (CD) was used because of its prodrug capabilities. CD was obtained from ATCC (#40999, plasmid pCD2) and the CD gene was amplified from this plasmid as follows. It should also be noted that the CD gene contains an NdeI restriction site; because we intended to use this particular enzyme to cut NdeI sites in the shuttle vectors, it was necessary to remove the NdeI site in the CD gene by PCR mutagenesis. This technique is the same one that was used to engineer in the new restriction sites into the E3 region, using the high-fidelity Pfu polymerase. Table 4 shows the oligonucleotides used to amplify the CD gene.

Briefly, a conservative mutation was made in the NdeI site, changing the base T to a C. The primers for the first PCR reaction were CD-NdeC and SwaCDNC. The plasmid pCD2 was used as a template. This product, along with the same template and primer CD-PacC, were used for the second PCR reaction. This accomplished two goals: it altered the NdeI site and added restriction sites PacI and SwaI to the 5' and 3' ends, respectively. This final PCR product was cut with PacI and SwaI; the shuttle vector, pGE3SV was also digested with PacI and SwaI. The fragments were gel purified using the Qiagen gel extraction kit and then ligated together using NEB T4 DNA Ligase. The E. coli strain XL-1 was transformed with the ligation mix, plated on ampicillin-containing plates for selection, and colonies were picked and cultured. The DNA was isolated and then screened by restriction digest to check for correct insertion and deletion. The clones which appeared correct were then sequenced throughout the entire CD gene and surrounding vector to verify that no unwanted mutations had taken place. This correct and verified clone was called pG-CDPacSwa and used in subsequent PCR amplifications where the CD gene was amplified for insertion into other regions. It should be noted that the CD gene contains a bacterial start codon, GTG. In all 5' primers, the start codon was included and changed to the eukaryotic codon, ATG.

The other CD-containing vectors were created by designing the appropriate primers which possess the desired restriction site at the 5' or 3' end of the gene; the 5' primer always containing the ATG start codon. The CD gene was inserted into E3 regions using the following restrictions sites: BstBI to StuI, NheI to MunI, NheI to PmeI, PacI to PmeI, SunI to MunI, ClaI to SwaI, and BamHI to SwaI. The plasmids were named: pG-CDBstStu, pG-CDNheMun, pG-CDNhePme, pG-CDPacPme, pG-CDSunMun, pG-CDClaSwa, pG-CD-BamSwa, respectively. All primers used are listed in Table 3 and the template was always the confirmed plasmid pG-CDPacSwa. The CD gene in the ClaI to SwaI region was inserted into the pGE3SV+V plasmid; the CD gene in the BamHI to SwaI region was inserted in the E3SV+B plasmid. All insertions were sequenced completely to ensure that no unwanted mutations had taken place and that the CD gene was inserted correctly.

It should be noted that there are three choices for 5' insertion site and 2 choices for 3' site that can be used for inserting genes into the 6.7-gp19K region. These are SunI, PacI, and NbeI for the 5' end, and PmeI and MunI for the 3'end. The PacI and SunI sites overlap the y-leader, an important sequence for translation of late gene products. Disruption of this sequence may abrogate its effect for certain applications. Therefore, another site, NheI was inserted which does not overlap the y-leader. If no adverse affect is seen, then the SunI to MunI sites, naturally present in Ad5, may be useful since it allows for a greater cloning capacity.

Several points are predicted from the viruses that result from the above E3 insertions. First, the construct that remove portions of the y-leader, as in pG-CDSunMun, may cause an adverse effect on the course of the infection, as discussed above. This may also be true of genes inserted into the PacI site, although less of the y-leader is deleted. Another prediction is that inserts into the 11.6K region, as in pG-CDBstStu, may result in a greatly attenuated infection. As has been published, deletion of the 11.6K protein (ADP, or Adenovirus Death Protein) does not allow the infected cells to lyse at the proper time, compared to wild type infection. In this case the cell continues to metabolize, the virus production per cell is higher, and the cell basically becomes a factory for producing the foreign gene. Also, since ADP is synthesized in large quantities using the major late promoter during the late phase of infection, a foreign gene inserted into this region would be expected to have the same expression characteristics. The results obtained with these viruses will be discussed below.

Example 5

Construction of TNF Plasmids

The plasmid containing the murine tumor necrosis factor (mTNF) gene was obtained from ATCC (#63169). This sequence contains the entire mTNF gene including the coding region for the prosequence. The mTNF gene was amplified from this plasmid by PCR (Table 4) and gel purified. The vector pGE3SV was cut with BstBI and StuI and gel-purified. At the same time, another vector, pG-E3SV+V was cut with ClaI and SwaI and gel purified. The purified PCR product was readily inserted into each of these vectors due to compatible ends. These constructs were called pG-mTNFBstStu and pG-mTNFClaSwa, respectively.

Using the ATCC plasmid as a template once again, mTNF gene was amplified by PCR. The plasmid pG-E3SV+B and the PCR product were cut with BamHI and SwaI, gel purified, and ligated together. This construct was called pG-mTNF-BamSwa. All constructs were sequenced extensively to check for unwanted mutations.

Example 6

Construction of CD and TNF Viruses

To build the above described CD constructs into the Ad5 genome, Ad5 TP-DNA was used. For the mTNF containing viruses, BstLink TP-DNA was used since it offers certain advantages. The plasmid construction for this BstLink is described in Example 11. Note that all transfections were performed on 6 cm dishes and in duplicate; the quantities described here are per each 6 cm dish.

Methods: the viruses E3-CD-PacPme (Onyx 301), E3-CD-NhePme (Onyx 302), E3-CD-SunMun (Onyx 303), E3-CD-NheMun (Onyx 304), E3-CD-BstStu (Onyx 305), and E3-mTNF-BstStu (Onyx 320) were made as follows: first, 0.5 micrograms of TP-DNA (Ad5 for CD viruses and BstLink for mTNF viruses) and ten micrograms of plasmid were cut with EcoRI (20 units) at 37 degrees for 5 hours. (An overabundance of plasmid DNA was used to allow approximately five micrograms of the actual insert DNA per transfection) At this point, the TP-DNA was left to digest at room temperature overnight while the cut plasmids were run on a 1% agarose gel overnight. The inserts were gel-purified using the Qiagen gel extraction kit. Ligation reactions consisted of the cut TP-DNA and the purified fragments with 10 units of high concentration T4 DNA Ligase (Boehringer Mannheim) overnight at 16 degrees. This reaction mixture was used directly for transfection.

Homologous recombination was used to generate the viruses: CDPacSwa, mTNFClaSwa, CDBamSwa, mTNF-BamSwa, because these mutations in the E3 region lie outside of the EcoRI restrictions sites. The quantities of DNA and TP-DNA are the same as above. The TP-DNA BstLink was cut with BstBI for the transfection. The CD-containing plasmids were cut with SpeI and NdeI and the mTNF-containing plasmids were cut with PacI and NdeI. The fragments were gel-purified and eluted in water. For transfections, the cut TP-DNA and the isolated fragments were mixed together and used without any further manipulations.

Transfection Procedures: For transfections, A549 cells were plated onto 6 cm dishes the preceding day so that they would be approximately 70 to 80% confluent the day of the transfection. To transfect these cells, 2 solutions were made and subsequently mixed. Solution A contained the ligation mixture and 300 ul of OptiMEM (Life Technologies) per 6 cm dish. Solution B contained 300 ul of OptiMEM and 13 microliters of Lipofectamine (Life Technologies). These two solutions were added together, mixed gently, and allowed to incubate at room temperature for 30 to 45 minutes.

Near the end of this incubation time, the cells were washed with warm OptiMEM and 2.4 ml of OptiMEM was added to each of the mixtures. This final 3 ml mix was then added directly to the washed cell monolayer and incubated at 37 degrees for 5 hours. Then 3 ml of DME containing 20% FBS was added to each dish without removing the transfection mix, bringing the final serum concentration to 10%. This was allowed to incubate at 37° C. overnight. The cells were overlaid with 8 ml of DME/2% FBS/1.0% agar noble (Difco). Five days after this overlay, another overlay (5 ml) was added which also contained 0.3% neutral red (Life technologies) to help visualize the plaques. Propagation and confirmation of virus mutants: As plaques appeared (10 to 20 days after transfection), they were isolated as agar plugs using a sterile Pasteur pipette. To propagate the virus present in the agar plugs, 3.5 cm plates were seeded with A549 cells in DME/10% FBS on the previous day. The day of the infection, the medium was changed to DME/2% FBS and the isolated plaques were added to the cells. The infections were checked daily for CPE (cytopathic effect, where the cells become rounded up and detach from the plate as a result of the virus infection), which usually occurred 3 to 5 days after infection. The entire medium and cells were collected and frozen at −20 degrees. To check for a virus mutation, 200 microliters of the cell and medium mix was used to isolate the viral DNA (along with cellular DNA) using the Qiagen Blood kit. This purified DNA was checked by PCR using primers which corresponded to the CD gene itself or the flanking E3 region. Once the PCR of the recombinant virus DNA was shown to produce a correct size fragment, further characterization included cutting the PCR fragments with restriction enzymes for patterns unique to CD or mTNF and also by sequencing the PCR product. Hirt analysis was also performed to confirm that the correct virus was obtained.

The correct viruses were expanded by infecting a T150 of A549 cells with 500 ul of the viral suspension obtained from the 3.5 cm dish. This was allowed to proceed to full CPE (when over 75% of the cells are no longer attached to the flask surface), which occurred in approximately 3 days. Then 7.5 ml of this cell and medium mixture was used to infect a 3-liter spinner of KB cells, and the virus produced was purified by CsCl-banding. Plaque assays were performed to determine the infectious particles per unit volume.

The viruses were named at this point in such a way to make it obvious to tell which insert had been added and where the insert was placed. Numbers for ease of reference were also assigned to each virus, and these appear in parenthesis. Their names are E3-CD-PacPme (Onyx 301), E3-CD-NhePme (Onyx 302), E3-CD-SunMun (Onyx 303), E3-CD-NheMun (Onyx 304), E3-CD-BstStu (Onyx 305), E3-mTNF-BstStu (Onyx 320), and E3-mTNF-ClaSwa (Onyx 321).

CD assay: To assay for cytosine deaminase (CD) activity, the reaction was performed similar to that as described in Roguiski et al 1997. Briefly, A549 cells were seeded into 10 cm plates so that they were about 70 to 80% confluent on the day of infection (about 2 to 4 million cells per plate). The cells were infected at an MOI (multiplicity of infection) of 10 pfu (plaque forming units) per cell for each of the E3-CD viruses. Ad5 and mock infected cells were included as controls. For the infection, the proper volume of virus was suspended in 2 ml of DME per 10 cm plate and then added to the cell monolayer. After one hour, 8 ml of DME/2% FBS medium was added to each plate. At various times post-infection (4, 8, 12, 24, 36, 48, 60, 72, 84, 96, 120 hours), the cells were rinsed, 1 ml of cold PBS was added, cells were scraped (using disposable cell scrapers) and pelleted into 1.5 ml eppendorf tubes. All PBS was removed and the cell pellets were flash-frozen in dry ice/ethanol and stored at −80° C. degrees. 200 ul of assay buffer (100 mM Tris/HCI (pH 8.0) 1 mM EDTA, 1 mM B-mercaptoethanol) was added to each pellet and the cells were lysed by 4 freeze/thaw cycles. The lysates were cleared by centrifugation at full speed for 5 minutes at 4° C. The quantity of protein was determined by a Bradford assay using Bio-rad reagents. For the enzyme assay, either 5 micrograms or 0.6 micrograms of protein from each sample were used, along with 2.5 mM [2-14C]-cytosine (1 uCurie; 5 ul; Moravek Biochemicals, #MC131) and assay buffer to bring the reaction volume to 10 ul. The reaction was allowed to proceed for one hour at 37° C. To quench the reaction, 10 ul of cold cytosine/uracil (0.4 mg/ml each) was added. Ten ul from each sample was spotted onto a thin layer chromatagraphy plate (Baker #7009-04) and then placed in an equilibrated tank with 1-butanol-water (86%/14%). After allowing the solvent front to approach the top of the plate (about 2 hours), the plate was allowed to dry and exposed to film. This autoradiogram was then scanned for the figures.

Murine TNF alpha assay: The A549 cells were plated onto 6 cm plates so that they would be approximately 80% confluent for the infection. The infection was performed as described above at an M.O.I. of 10. At various time points, the medium was removed and replaced with 3 ml of fresh DME/2% FBS. This was incubated at 37° C. for one hour. After that interval, a one ml aliquot of the medium was removed and stored frozen at −80° C. until all samples were collected. The medium was replaced on each plate so the final volume was 4 ml until the next time point. The mTNF that was secreted into the medium was assayed using a commercial ELISA assay kit obtained from Biosource, #KMC3012. The assay was conducted according to the manufacturer's instructions. Each sample was determined in duplicate and each time point was collected from 4 different plates of infected cells.

Western Blot analysis: For western blot analysis, A549 cells on a 6 cm plate were infected at an M.O.I. of 10. At various times post-infection, the cells were scraped and collected as described above. The cells pellet was stored at −80° C. Three hundred ul of lysis buffer was added to each sample, freeze/thawed 3 times, and passed through a 22-gauge needle. A Bradford assay was performed to determine the quantity of protein. Ten micrograms of total protein was loaded onto a 4-20% SDS/PAGE gel and electrophoresed. The proteins were transferred onto a PVDF membrane, blocked with 3% dry milk in PBS, and blotted with the appropriate antibody. The antibodies for the E3 proteins and for pVIII (a protein made during the late times of infection) were polyclonal rabbit antibodies. These were used at 1:400. The antibody for murine TNF was obtained from "R and D Systems" and was used at 0.1 ug/ml. The appropriate secondary antibodies were used and then visualized using the ECL system (Amersham).

In addition to Western analysis of cell lysates, the medium that was collected at hourly intervals was analyzed by western blots using the same anti-mTNF antibody and 25 ul of medium loaded per lane.

TABLE 4

| Oligonucleotides used to amplify the CD and mTNE genes (sequences are 5' to 3'). | |
|---|---|
| CD2-NdeC | GCTGCAAGTGCTGCACATGGGGCTGCATG |
| PacCD | GTGAGCTTAATTAAGGCTAGCAATGTCGAATAA-CGC |
| PmeCD | GTGAGCGTTTAAACAGTCGTTCAACGTTTGTAATCG |
| NheCD | GGCCGCTAGCGGCTAACAATGTCGAATAACGC |
| SunCD | GTGAGCCGTACGAGGCTAGCAATGTCGAATAACGC |
| MunCD | GTGAGCCAATTGCAGTCGTTCAACGTTTGTAATCG |
| BstBICD | GCGCTTCGAAGTGGAGGCTAACAATGTCGAATA |
| StuICD | GGCCAGGCCTCTAAGCTCGCTGTAACCCAGTCG |
| 5BamTNF | GGCCATCGATGACACCATGAGCACAGAAAGCATG |
| 5ClaTNF | GGCCATCGATGACACCATGAGCACAGAAAGCAT-G |
| 3SwspTNF | CGCGAATATTTAAATCCATTCCCTTCACAGAGCA-ATGAC |
| 5NheMIP3 | GCGCGCTAGCCCACCATGTGCTGTACCAAGAGTT-TGCT |
| 3MunMIP3 | GGCCCAATTGTTTACATGTTCTTGACTTTTTACT-GAG |
| 5NheMCP3 | GCGCGCTAGCCCACCATGTGGAAGCCCATGCCCT-CACC |
| 3MunMCP3 | GGCCCAATTGTCAAAGCTTTGGAGTTTGGGTTTT-CTTG |

Example 7

Viral Expression of CD or mTNF

CD-containing viruses: E3-CD-PacPme (Onyx 301), E3-CD-NbePme (Onyx 302), E3-CD-SunMun (Onyx 303), E3-CD-NheMun (Onyx 304). The cell line A549 was infected with each of the viruses Onyx 301, Onyx 302, Onyx 303, and Onyx 304 at a M.O.I. (multiplicity of infection) of ten. At the designated hours post infection (p.i.), samples were harvested as described in methods section for assay of CD activity. Also at each time point, a picture was taken of the cells to show phenotypic differences.

Figure 8:
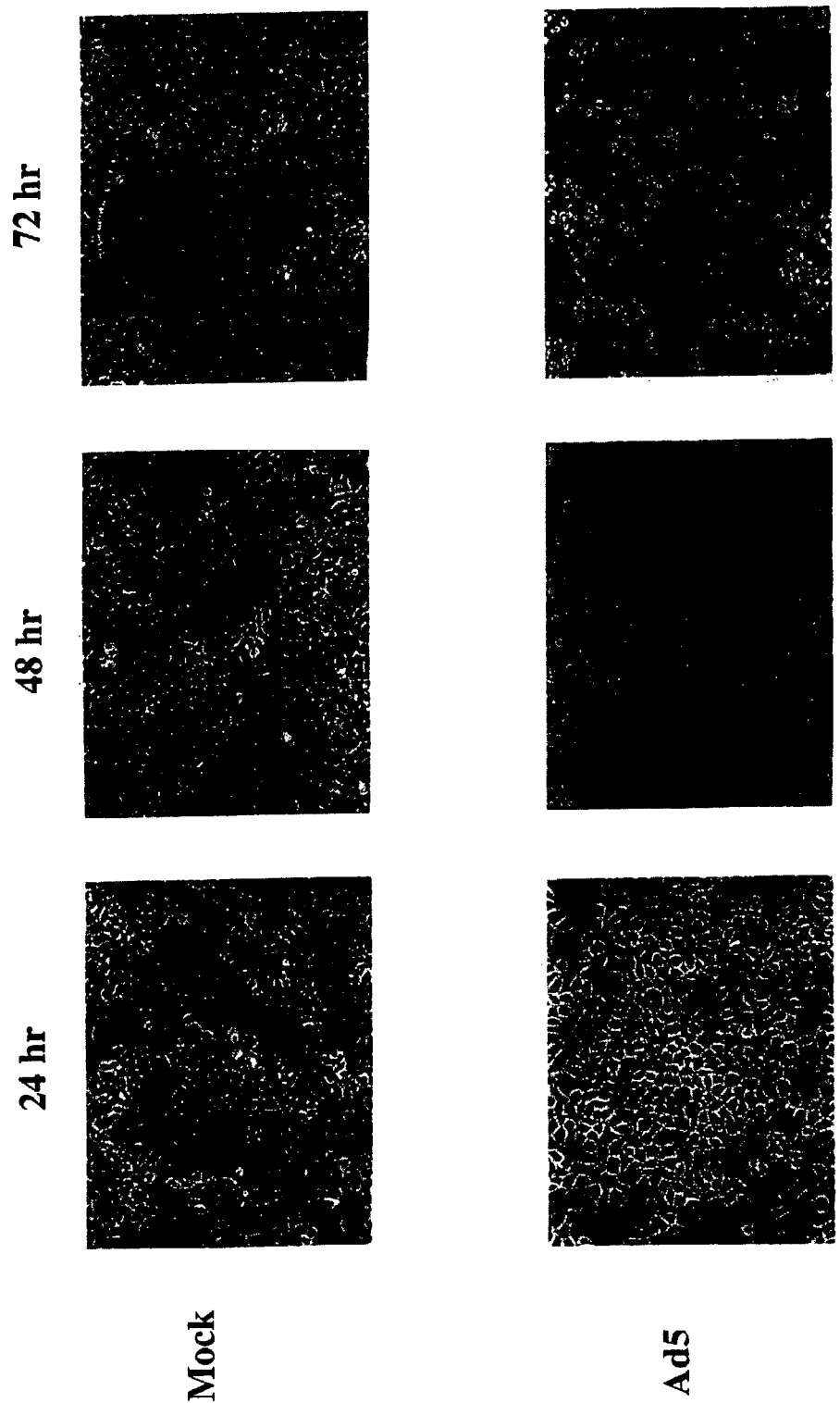
FIG. 8 shows A549 cells mock infected or infected with Ad5.
Figure 9:
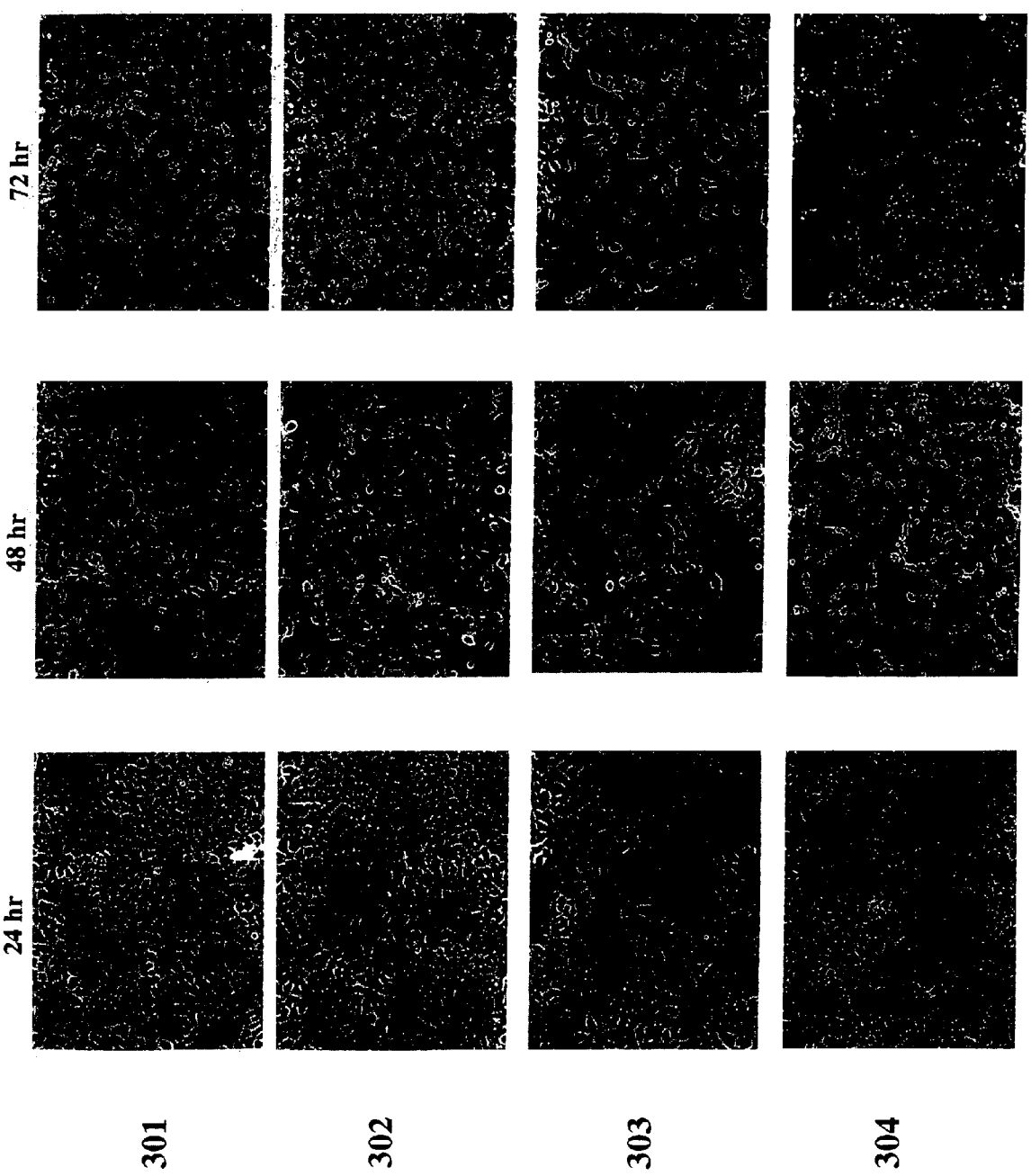
FIG. 9 shows A549 cells infected with viruses Onyx 301, Onyx 302, Onyx 303, and Onyx 304.

FIG. 8 shows control mock infected and Ad5-infected cells, and FIG. 9 shows cells infected with viruses with CD inserted into the gp19K region, that is, viruses, Onyx 301, Onyx 302, Onyx 303, and Onyx 304. The wild type infection proceeds normally and shows almost total CPE by 48 hr p.i. The Onyx 304 virus shows near wild type levels of CPE at 48 hr p.i., while Onyx 303 shows a slightly attenuated infection. The other two viruses, Onyx 301 and Onyx 302, show an intermediate phenotype. Interestingly, Onyx 303 is the CD substitution using the SunI site and the infection is slower than wild type likely due to the deletion of part of the y-leader, abrogating its addition to late messages and probably lowering their efficiency of translation. The viruses Onyx 301 and Onyx 302 lag behind Ad5 only slightly. It is noteworthy that 22 base pairs of the y-leader is deleted in the case of Onyx 301, whereas Onyx 302 contains the entire y-leader.

Figure 10:
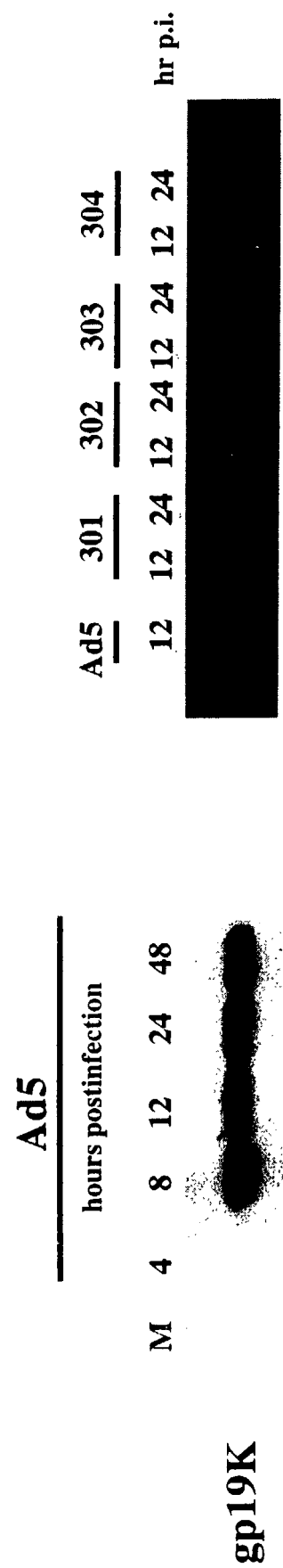
FIG. 10 shows western blot analysis of gp19k from cell lysates prepared from cells infected with viruses Onyx 301, Onyx 302, Onyx 303, and Onyx 304 at different times post infection.

Experiments show that the time of expression of heterologous genes inserted in the E3 viral constructs of the instant invention is similar to the endogenous viral genes that they replace. The viruses 301, 302, 303, and 304 are substitutions of gp19K. As shown in FIG. 10, gp19K synthesis begins between 4 and 8 hours post-infection, as detected by Western blot analysis. This is similar to published values. FIG. 10 also shows that the CD viruses do not make gp19K, as predicted, since the gene has been deleted.

Figure 11:
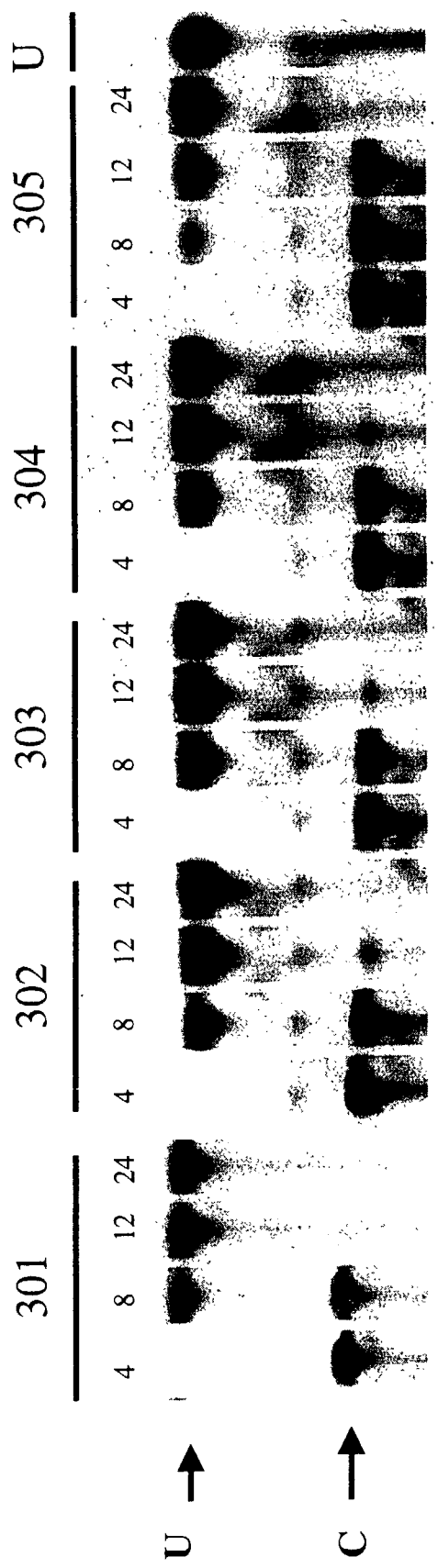
FIG. 11 shows a CD assay on cell lysates (0.5 ug of protein) prepared from cells infected with viruses Onyx 301, Onyx 302, Onyx 303, Onyx 304, and Onyx 305 at different times post infection.

To check when CD was first expressed, 5 ug of total protein were used per reaction. The results are shown in FIG. 11. As with gp19K, the CD activity is seen as early as 8 hr p.i. in viruses 301 through 304. This validates that endogenous expression time is similar to the inserted CD gene.

To get an idea of the amount of CD protein being synthesized from each position, 0.6 ug were used for each reaction and the results are shown in FIG. 12. In order to be able to compare between the different viruses, a smaller amount of protein was used in to ensure that substrate conversion was incomplete. FIG. 12 shows that Onyx 301, Onyx 302, and Onyx 304 synthesize similar amounts of CD. On the other hand, Onyx 303 shows total conversion of substrate at about 36 hours, indicating that there is proportionally more CD synthesized by Onyx 303 infected cells compared to the others.

Figure 16:
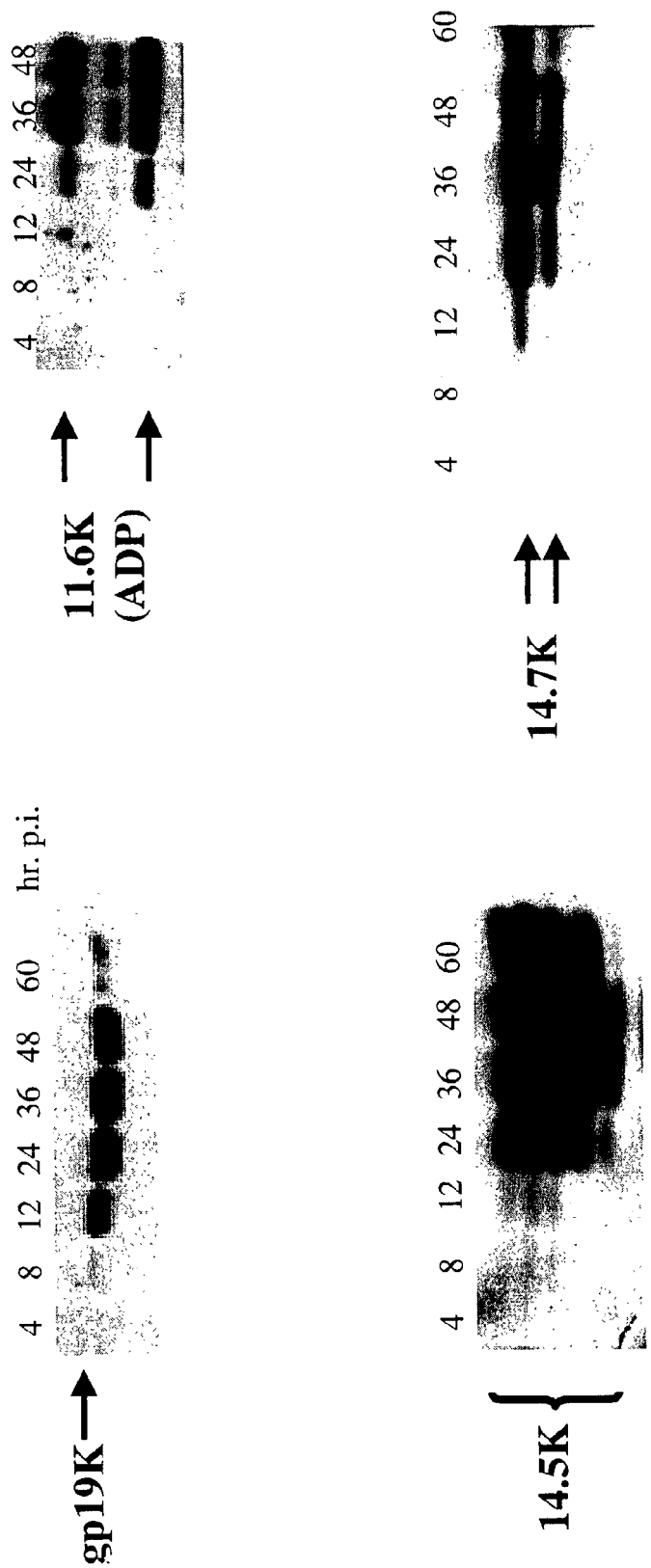
FIG. 16 shows Western blots of the E3 proteins from A549 cells infected with Ad5. The numbers above each lane refer to times post-infection, p. i.
Figure 19:
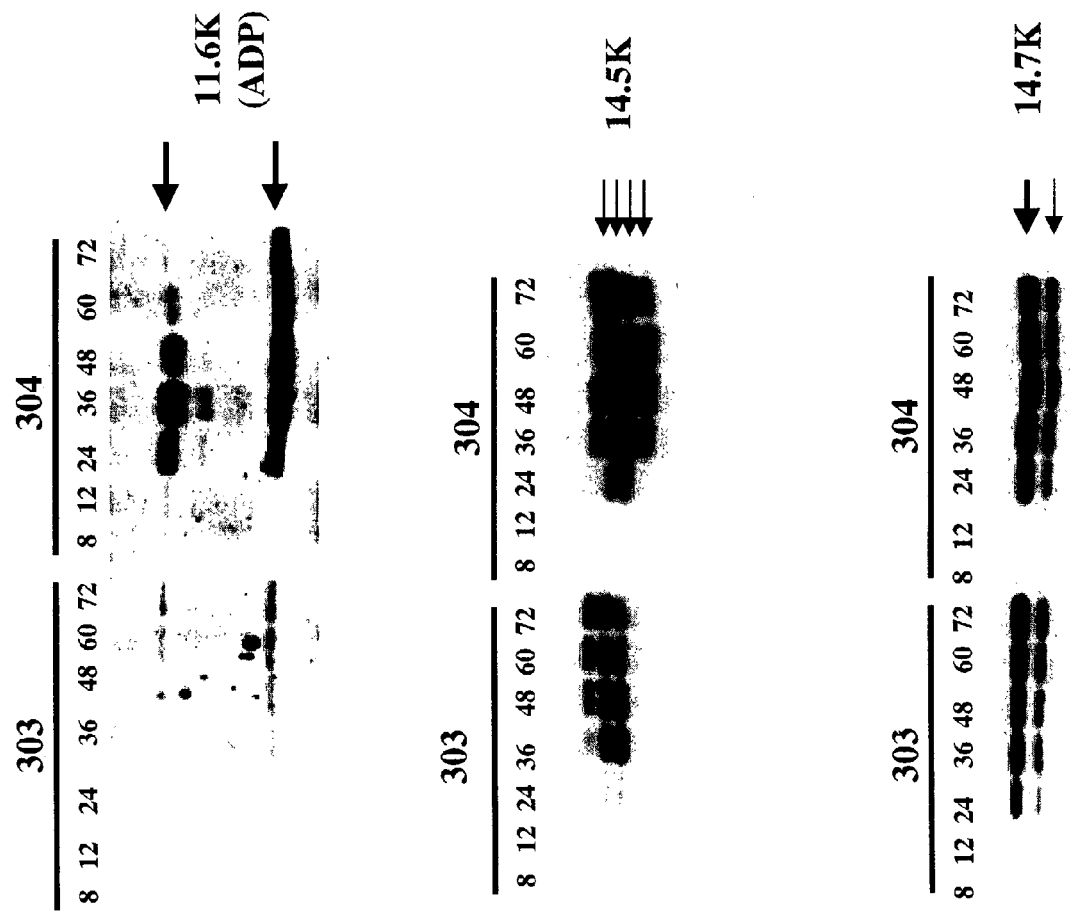
FIG. 19 shows Western blots of the E3 proteins 11.6K, 14.5K. and 14.7K from cells infected with 2 CD containing viruses, Onyx 303 and Onyx 304. These levels can be compared to the levels of E3 proteins produced by Ad5 virus shown in FIG. 16.

To ensure that the remaining E3 genes still express their corresponding proteins, A549 cells were infected at an MOI of 10 with Ad5, Onyx 303 or Onyx 304, and the cells were harvested at various times post-infection. The proteins were extracted from the cell pellets, run on a gel, transferred, and analyzed by Western blot using the appropriate antibody. The results are shown in FIG. 16 and FIG. 19, for Ad5, and Onyx 303 and Onyx 304, respectively. Onyx 304 produces wild type levels of the E3 proteins, namely 11.6K, 14.5K, and 14.7K. Interestingly, Onyx 303 produces almost no 11.6K, which could account for its attenuated phenotype. Without wishing to be held to any particular theory, we speculate that because the y-leader is almost completely missing as a result of the insertion of CD, that the message for 11.6K is not translated efficiently. Although Onyx 303 appears to synthesize Ad5 wild type levels of 14.7K, both the level and processing of the 14.5K protein are altered.

Figure 13:
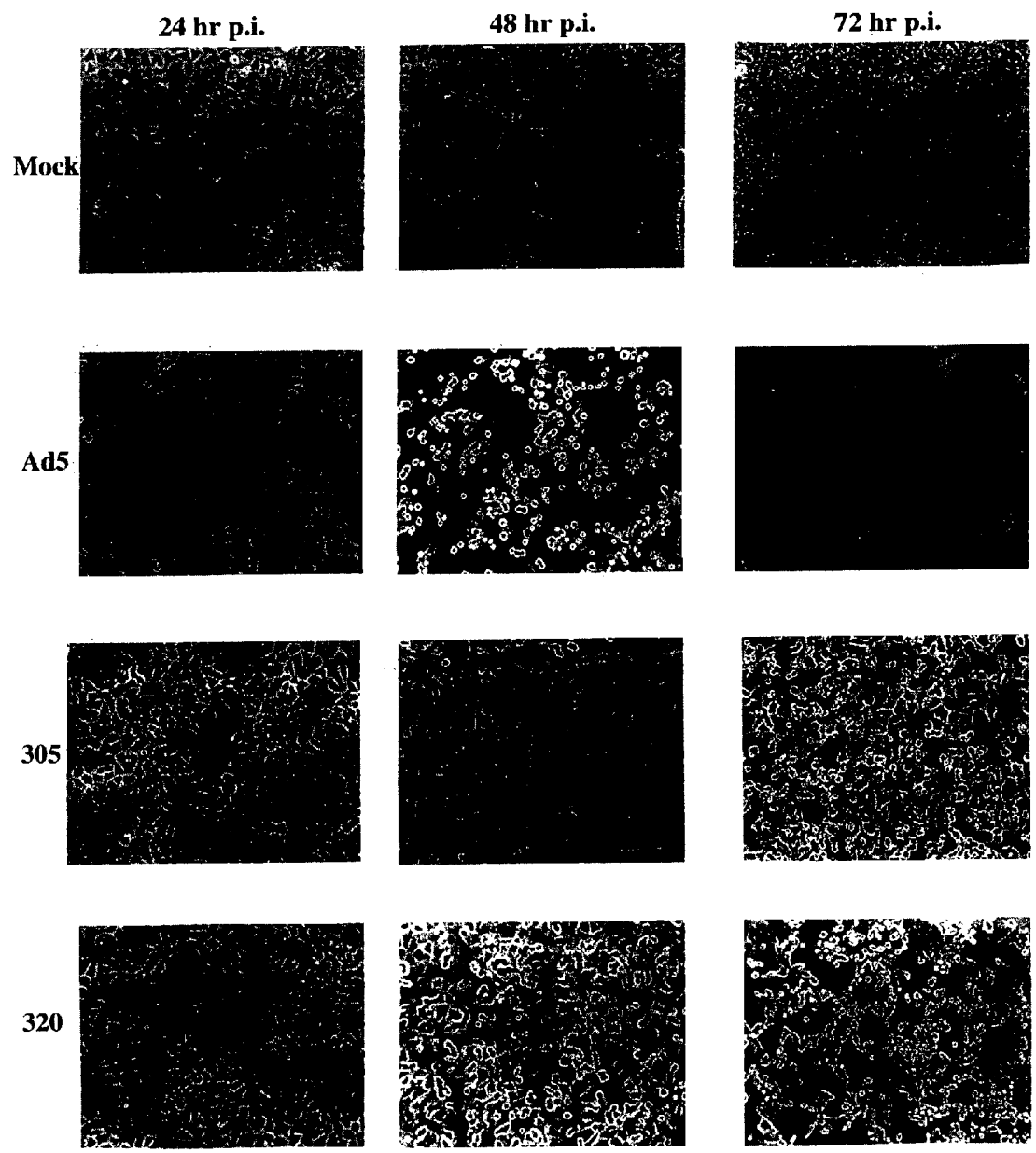
FIG. 13 shows the cytopathic effect of viruses Onyx 305 and Onyx 320 at different times post infection.
Figure 14:
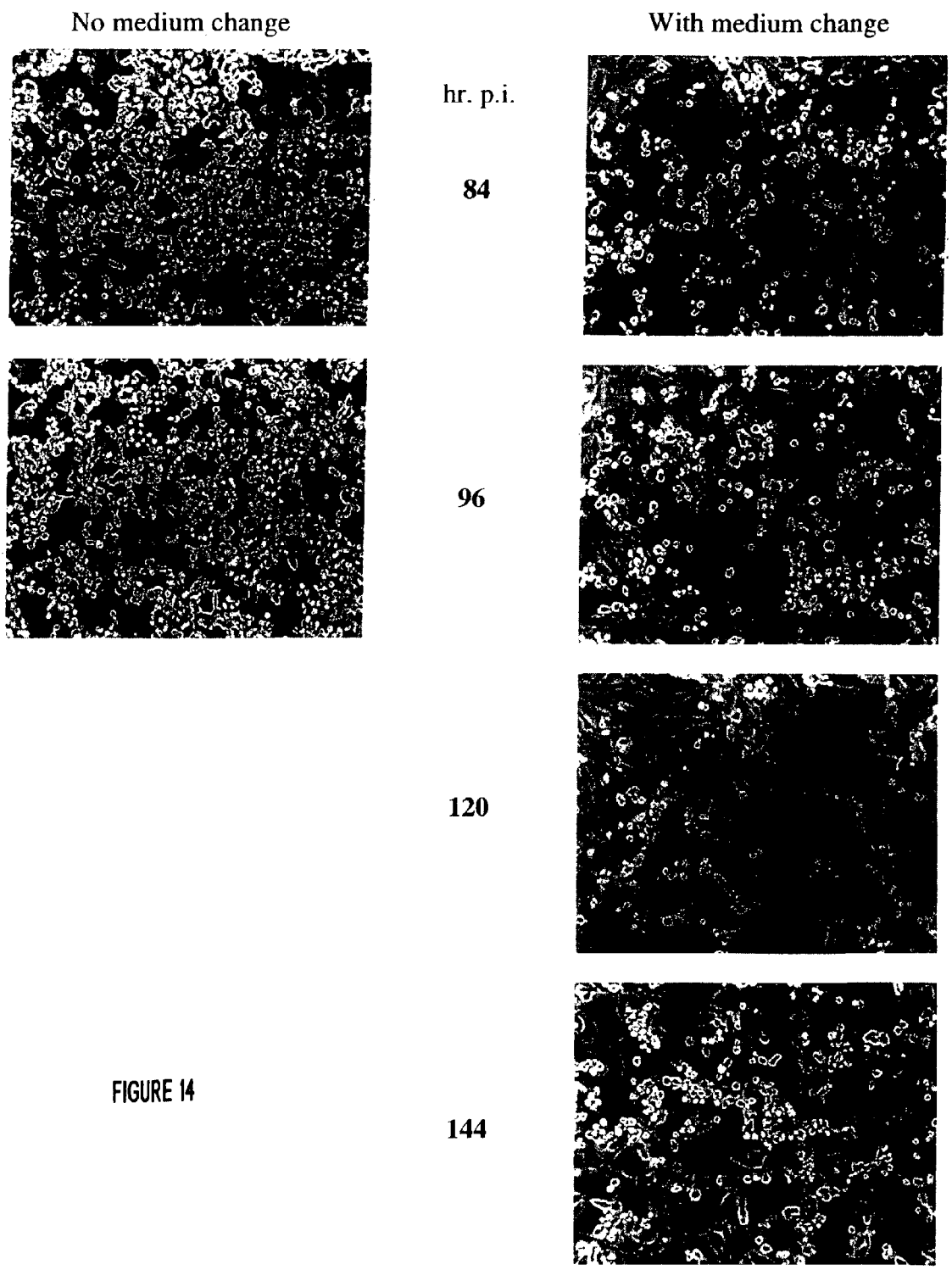
FIG. 14 shows the cytopathic effect of virus Onyx 320 on cells that have, or have not had medium changes at certain times post infection.

ADP substitutions: CD and mTNF: The E3-Adenovirus Death Protein (ADP) gene was replaced with either CD or mTNF, as described above. It is known that ADP deleted viruses do not lyse infected cells at the expected time compared to wild type. Thus, the gene is thought to be important in virus release. As with the ADP deletion viruses, the invention viruses which replace other genes in this region show a similar phenotype. This is shown in FIG. 13 and FIG. 14. At 72 hr p.i. when the wild type infection shows total CPE, virus Onyx 305 (CD insertion) and virus Onyx 320 (mTNF insertion) exhibit significant but reduced CPE compared to Ad5. The infection doesn't reach total CPE until 96 hr p.i. (FIG. 14). If the medium is changed every 24 hrs, the cells remain attached and exhibit an almost normal phenotype even at 120 hr p.i. It is not until after 164 hr p.i. (7 days) that the cells appear to show classic CPE and come off the dish. This is a key observation and will be useful in a therapeutic sense since even if infected cells do not lyse immediately, they will nevertheless continue to express the heterologous gene of interest.

ADP is predominately a late protein whose expression is thought to be driven by the major late promoter and expressed at high levels during the late phase, that is, after DNA replication. To determine if inserted foreign genes show similar kinetics, a CD assay was performed on Onyx 305, and analysis for mTNF was performed on Onyx 320. As shown in FIG. 11, Onyx 305 does not show substantial CD activity until 12 hr p.i., a time when the virus has entered into the late phase. Also contrasted in FIG. 11 is the comparison with CD in the gp19K region, an early region. Clearly, there is a difference in the timing that the protein is synthesized.

Figure 15:
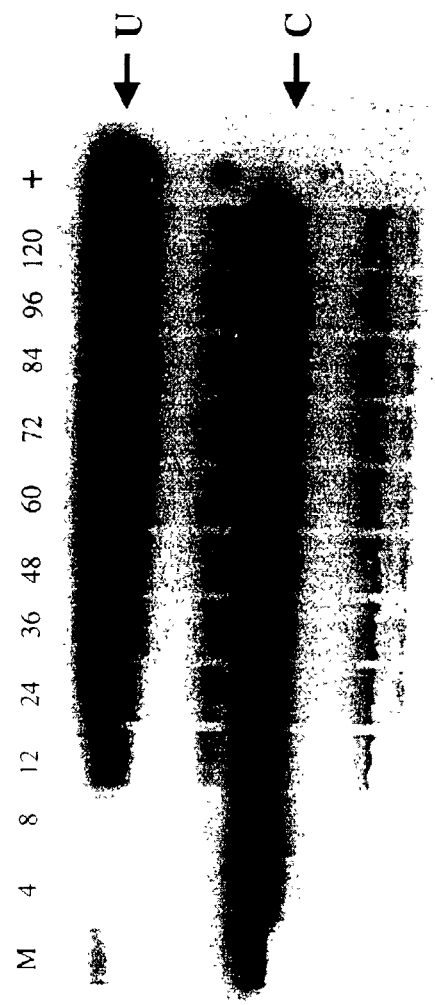
FIG. 15 shows the expression of CD at different times by cells infected with virus Onyx 305.

To compare the amount of CD activity, a CD assay was performed using 0.6 ug of total protein in each reaction (FIG. 15). Upon visual inspection and comparison to FIG. 12 (experiments were done at the same time), it appears that Onyx 305 does not synthesize quite as much as Onyx 301-304. But it should be noted that the Onyx 305-infected cells have an attenuated course of infection, and therefore, importantly, will synthesize CD for a considerably longer period of time.

Figure 18:
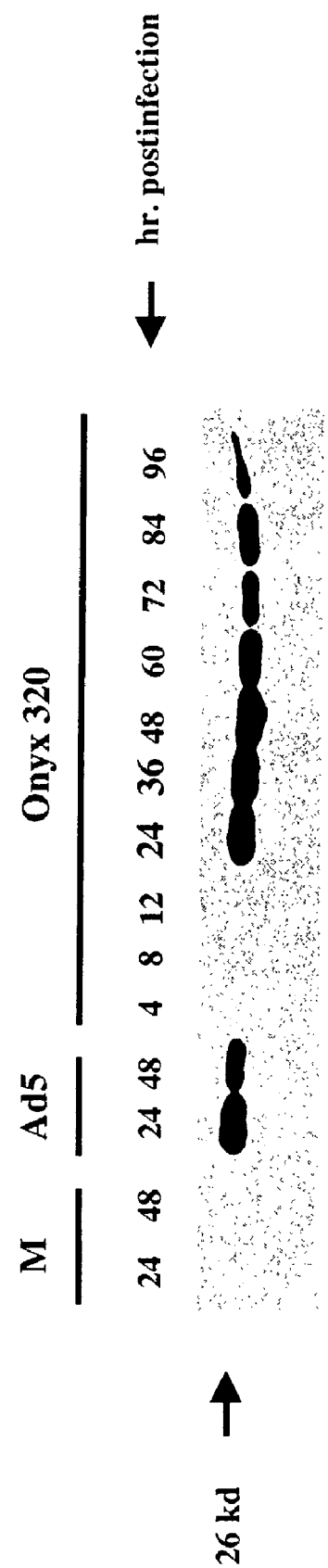
FIG. 18 shows a Western blot of the pVIII protein from the L4 region from cells infected with either Ad5 or Onyx 320, or mock-infected cells (M). The numbers above each lane refer to times post-infection, or p. i.

As a check for late stage of infection, Western blot analysis was performed on cell lysates and blotted with an antibody to ADP (11.6K), as well as to a late structural protein, pVIII. Both 11.6K (FIG. 16) and pVIII (FIG. 18) expression was seen in Ad5 infected cells. pVIII expression was also observed in Onyx 320 infections occurring at 24 hr p.i. (See, FIG. 18), indicating that the virus had entered into the late phase between 12 and 24 hr p.i. Also note that Onyx 305 fails to produce ADP, as expected, since it does not contain the gene (See, FIG. 20).

CD inserted in place of ADP exhibits a similar time to expression as ADP. A similar observation was made with Onyx 320, which has mTNF inserted in place of ADP. Briefly, cells were infected and lysates made at different times p.i. Western blot analysis was performed on these lysates, using both mock-infected and Ad5-infected cells as controls. It was shown that intracellular mTNF expression was not seen until after 24 hr p.i. See, FIG. 21). This is consistent with our previous findings that generally foreign genes mirror the expression profiles of the endogenous adenoviral gene that they replace.

Example 8

Expression of mTNF in Onyx 320 Mirrors Endogenous Late Gene Expression

Figure 20:
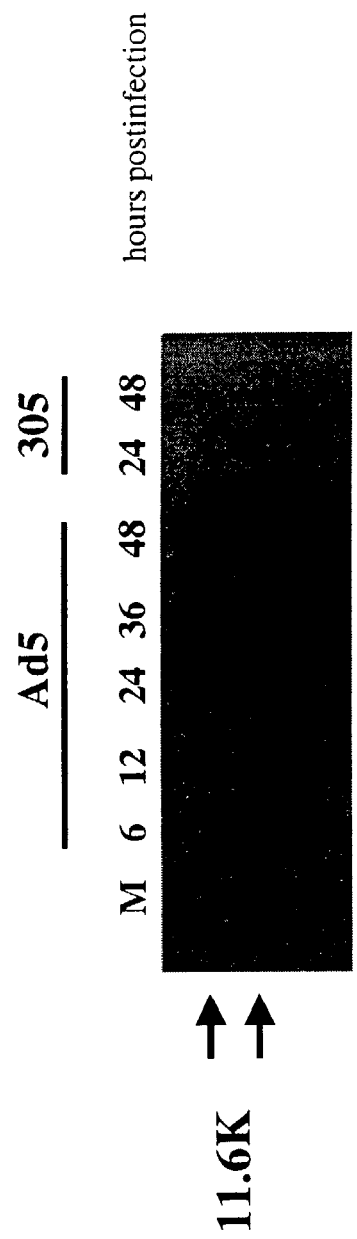
FIG. 20 shows a Western blot of 11.6K protein from cells infected with Ad5 or Onyx 305.
Figure 21:
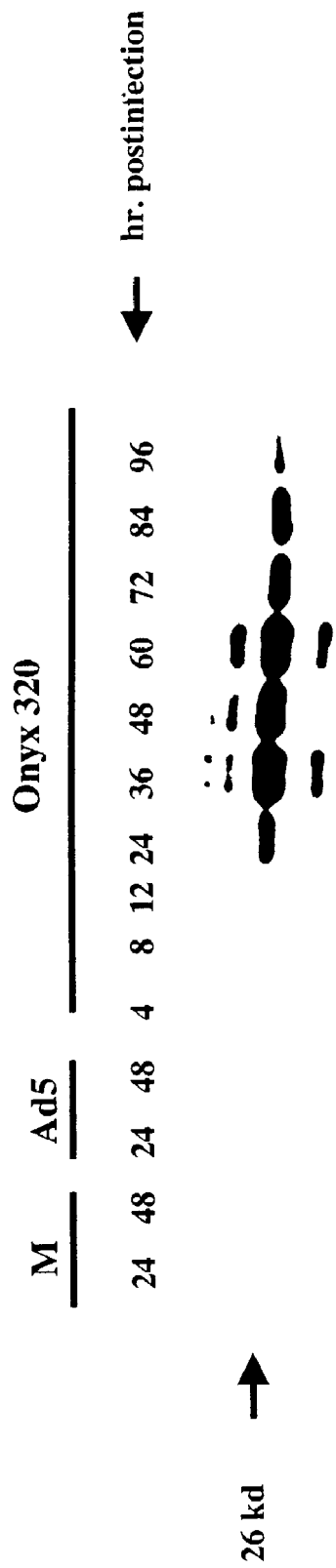
FIG. 21 shows a Western blot of the 26 kD intracellular form of murine TNF (mTNF) synthesized by Onyx 320 infected cells. As controls, mock infected and Ad5 infected cells were also analyzed for the presence of mTNF.

Additional experiments were conducted to quantify the expression of mTNF from Onyx 320, and to confirm that mTNF exhibits a late expression pattern similar to 11.6K.

mTNF Quantification: A549 cells were infected with Onyx 320 at an m.o.i. of 10 and the cells were harvested at the indicated times post-infection. To measure secretion of mTNF, the medium was removed one hour prior to the indicated time point and replaced with 5 ml of fresh medium. Aliquots of the newly added medium were then removed at the end of that hour to obtain data indicating the amount of mTNF produced per hour. As a control, Ad5 and mock infections were also conducted. FIG. 20 shows Western blot analysis of the timing and relative levels of expression of the endogenous E3 gene, 11.6K. Based on the detection limits of this assay, and previous published data, 11.6K is predominately synthesized after the start of the late phase of infection. FIG. 21 shows Western blot analysis of intracellular mTNF. This is the 27 kD uncleaved form of the molecule. See, Kriegler et al., Cell, 1988 Apr. 8; 53(1): 45-53. As is true of the 11.6K protein, mTNF expressed from this region is predominately synthesized and detected during the late phase of infection.

Figure 22:
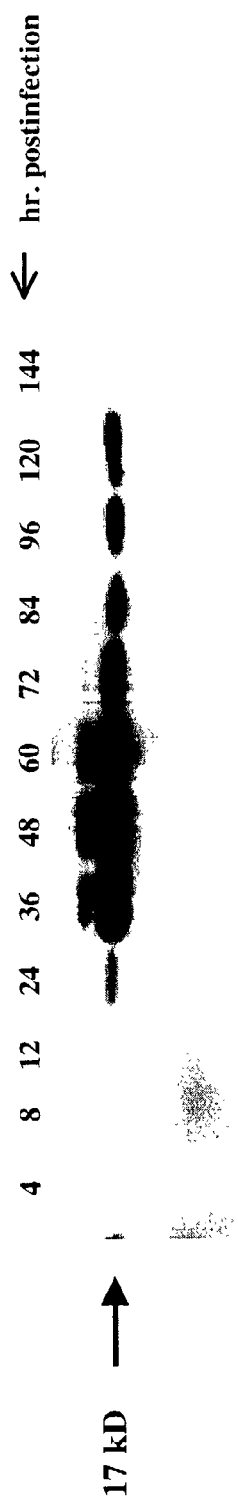
FIG. 22 shows a Western blot of 17 kD mTNF secreted into the culture medium from Onyx 320 infected cells. The medium was changed one hour before each indicated time point and then aliquots were taken at the indicated times post infection. 25 µl of culture medium was run on a gel and blotted.

FIG. 22 shows Western blot analysis of mTNF secreted into the medium during the one hour preceding the indicated time points. Twenty-five ul of culture medium was run on the gel to obtain this result. This shows that again detectable levels of the mTNF are produced at late times post-infection. Further, the mTNF produced is properly cleaved as it runs at the predicted molecular weight of 17 kD. This blot also shows that de novo synthesis was still occurring up to 144 hr p. i.

Figure 23:
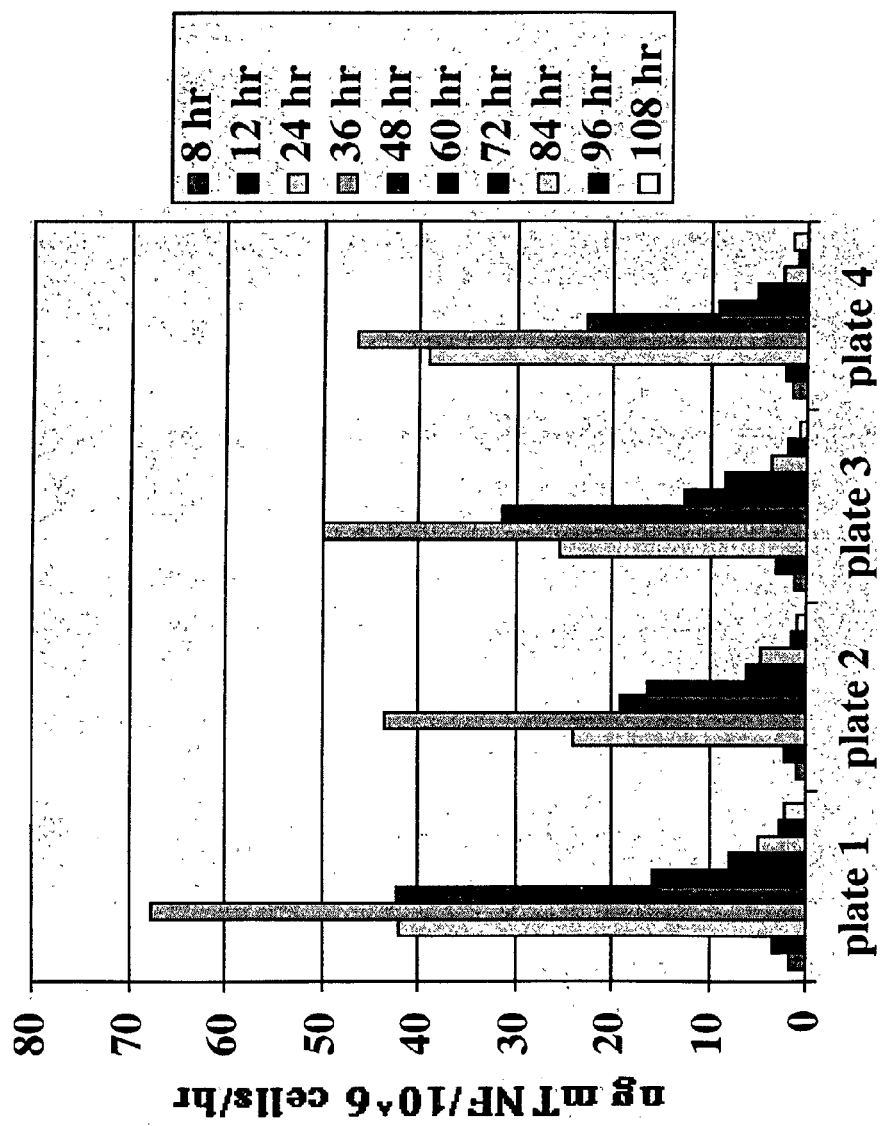
FIG. 23 shows the results of an ELISA assay which measured the amounts of secreted MTNF present in the culture supernatant as described in FIG. 22. The results of 4 individual experiments are shown.

To quantitate the amount of mTNF secreted, aliquots were collected during the one hour time points and the mTNF present was quantitated using a commercially available ELISA kit. FIG. 23 shows the results of 4 different experiments, and the results are expressed as the amount of mTNF produced per hour per one million cells. As shown in the figure the infected cells express high levels of mTNF: indeed, about 43 to 68 nanograms were measured during the highest production period.

Figure 17:
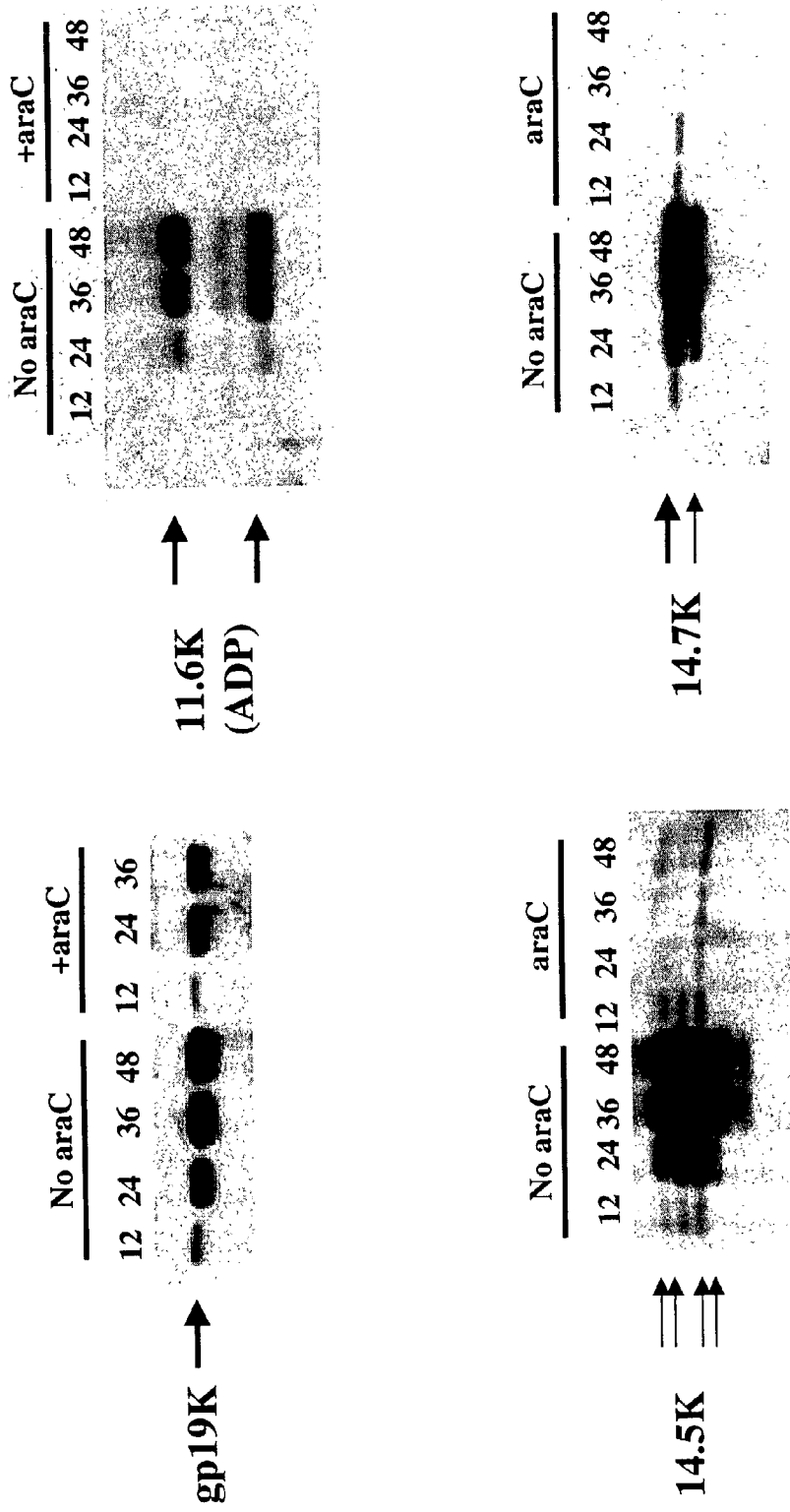
FIG. 17 shows Western blots of E3 proteins from cells infected with Ad5 both in the absence and presence of araC, an inhibitor of DNA replication. The numbers above each lane refer to times post-infection, p. i.
Figure 24:
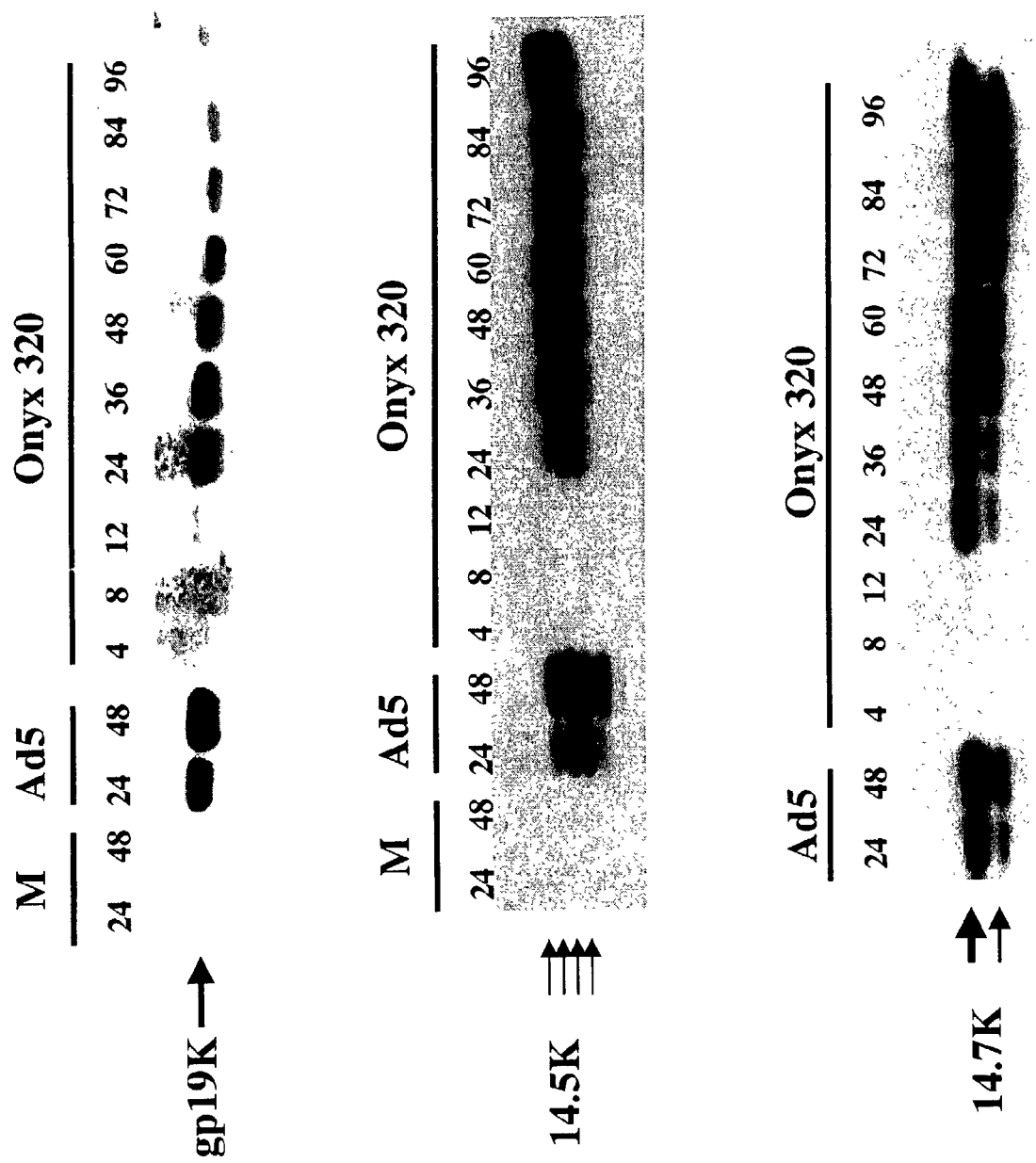
FIG. 24 shows Western blots of the E3 proteins gp19K, 14.5K, and 14.7K from A549 cells infected with Onyx-320. As a control, two time points from an Ad5 infection are included. The numbers above each lane refer to times post-infection, p. i.
Figure 25:
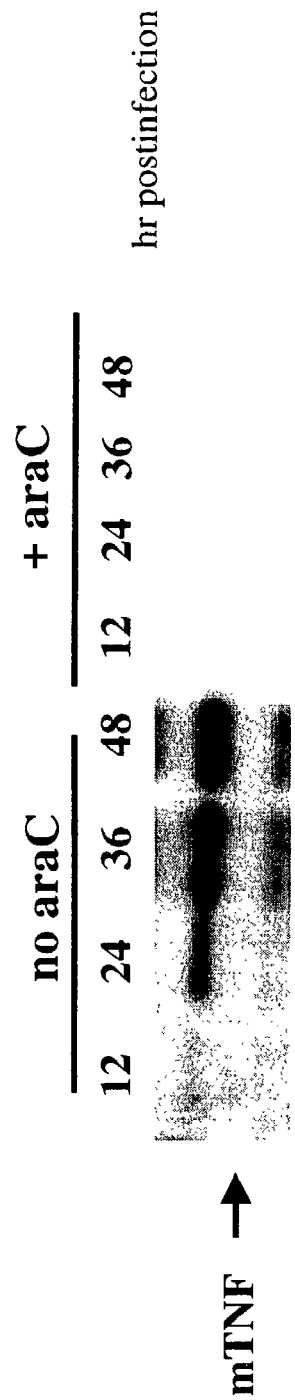
FIG. 25 shows a Western blot of intracellular mTNF from cells infected with Onyx 320, and incubated in the presence or absence of araC.
Figure 26:
FIG. 26 shows Western blots of the L4 protein, pVIII, from cells infected with Ad5 or Onyx 304, 305, and 320 and incubated in the presence or absence of araC.

To address the issue of expression of the remaining E3 proteins, Western blot analysis was performed to detect gp19K, 14.5K, and 14.7K from Onyx 320, and Ad5-infected cells. As shown in FIG. 24, Onyx 320 synthesizes similar levels to Ad5 of the E3 genes, gp 19K, 14.5K, and 14.7K; however, the processing of 14.5K is altered.

mTNF is Expressed as a Late Protein: An important characteristic of adenoviral late protein expression is that it is dependent on viral DNA synthesis. Thus, a classic experiment to show bona fide late protein expression is to determine whether or not expression occurs in the presence of araC, an inhibitor of DNA replication. FIG. 17 shows the expression of gp19K, 11.6K, 14.5K and 14.7K in the presence and absence of araC in cells infected with Ad5. Note that there is little or no detectable expression of the late protein 11.6K. Thus, to determine if mTNF when inserted in place of the 11.6K exhibited a late protein expression pattern, experiments were conducted to measure expression in the presence of araC. FIG. 25 shows that intracellular mTNF is not expressed in the presence of araC, whereas it is in its absence, indicating that mTNF is indeed displaying a late protein expression pattern. As a control, FIG. 27 shows that an early protein, gp19K, is synthesized in the presence of araC by both Ad5 (See, also FIG. 17), and Onyx-320. Lastly, another control was run to further confirm that Onyx 320 infection truly reaches late phase in the absence of araC. Western blot analysis was performed against another known late protein, pVIII. FIG. 26 shows that pVIII is not expressed in the presence of araC, but is in its absence. This further supports that mTNF is expressed as a true late protein. Note that FIG. 26 also shows the expression pattern for pVIII in Onyx 304 and Onyx 305, and the results with these viruses are similar to those observed for Onyx 320.

Example 9

Expression of mTNF from the E3B Region of Onyx 321

Figure 28:
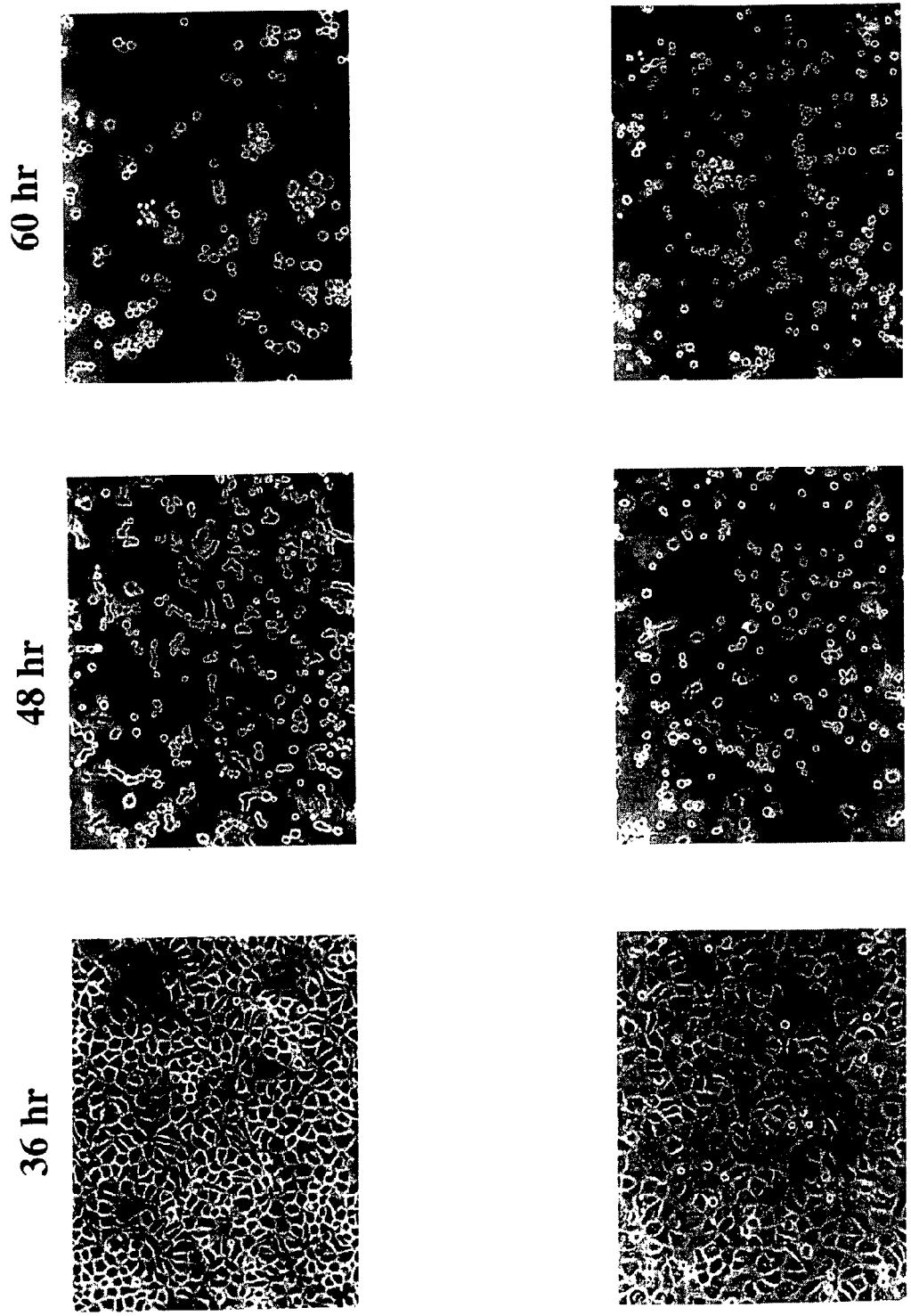
FIG. 28 shows pictures of A549 cells which have been infected with either Ad5 or Onyx 321 and photographed at the indicated times post-infection.

As described above, Onyx 321 has the entire E3B region substituted with mTNF using the engineered sites ClaI and SwaI. Experiments were conducted to determine the expression properties of mTNF from this region of the virus. A549 cells were infected at an MOI of 10 and photographed at the indicated times post-infection (FIG. 28). At the 48 hour time point, Onyx-321 showed greater CPE than wild type virus at the same time post-infection.

Figure 29:
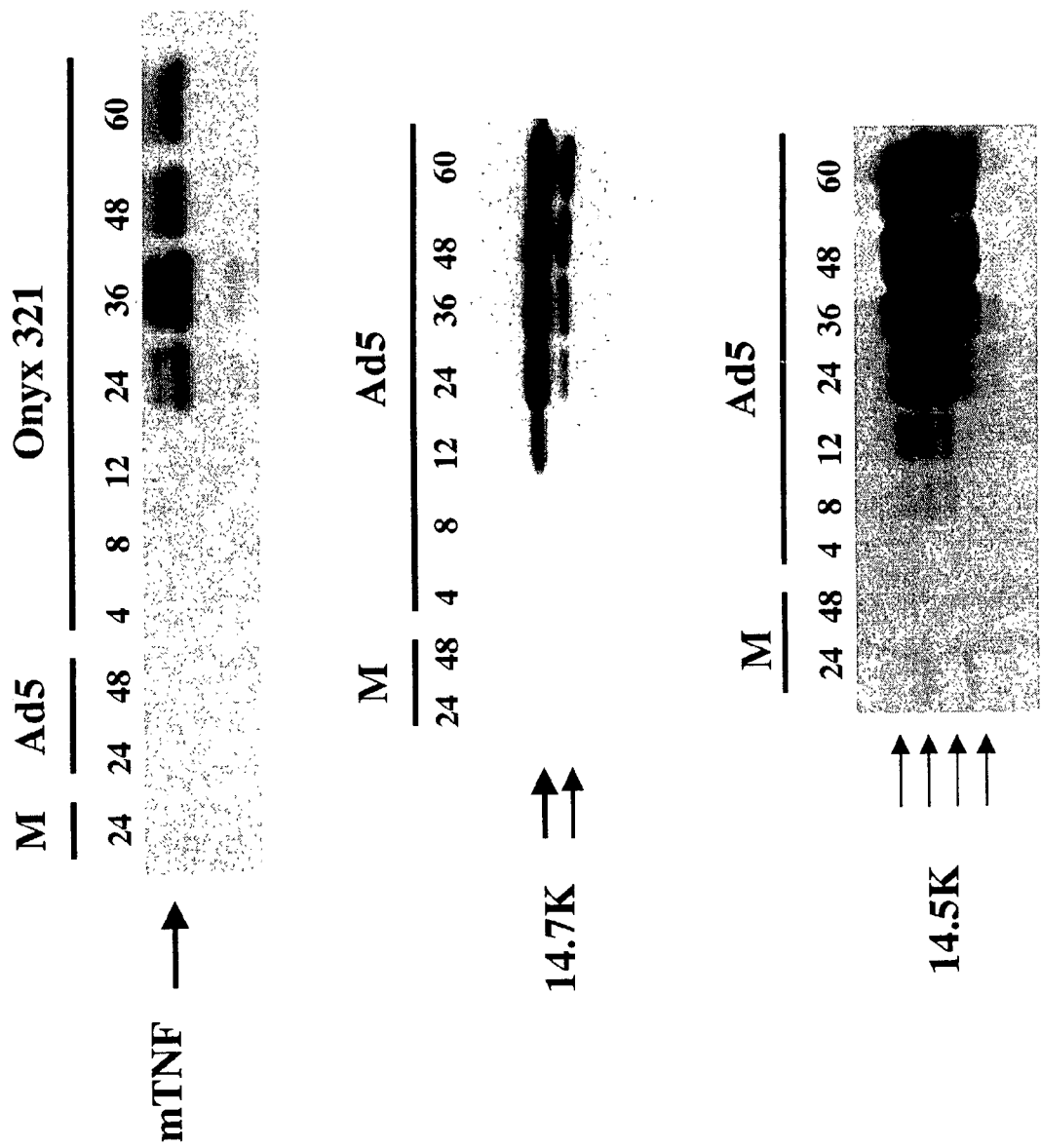
FIG. 29 shows Western blots of mTNF, and the E3 proteins 14.5K and 14.7K from A549 cells infected with either Ad5 or Onyx 321. The results of mock (M) infected cells at 24 hours are also shown. The numbers above each lane refer to times post-infection.
Figure 30:
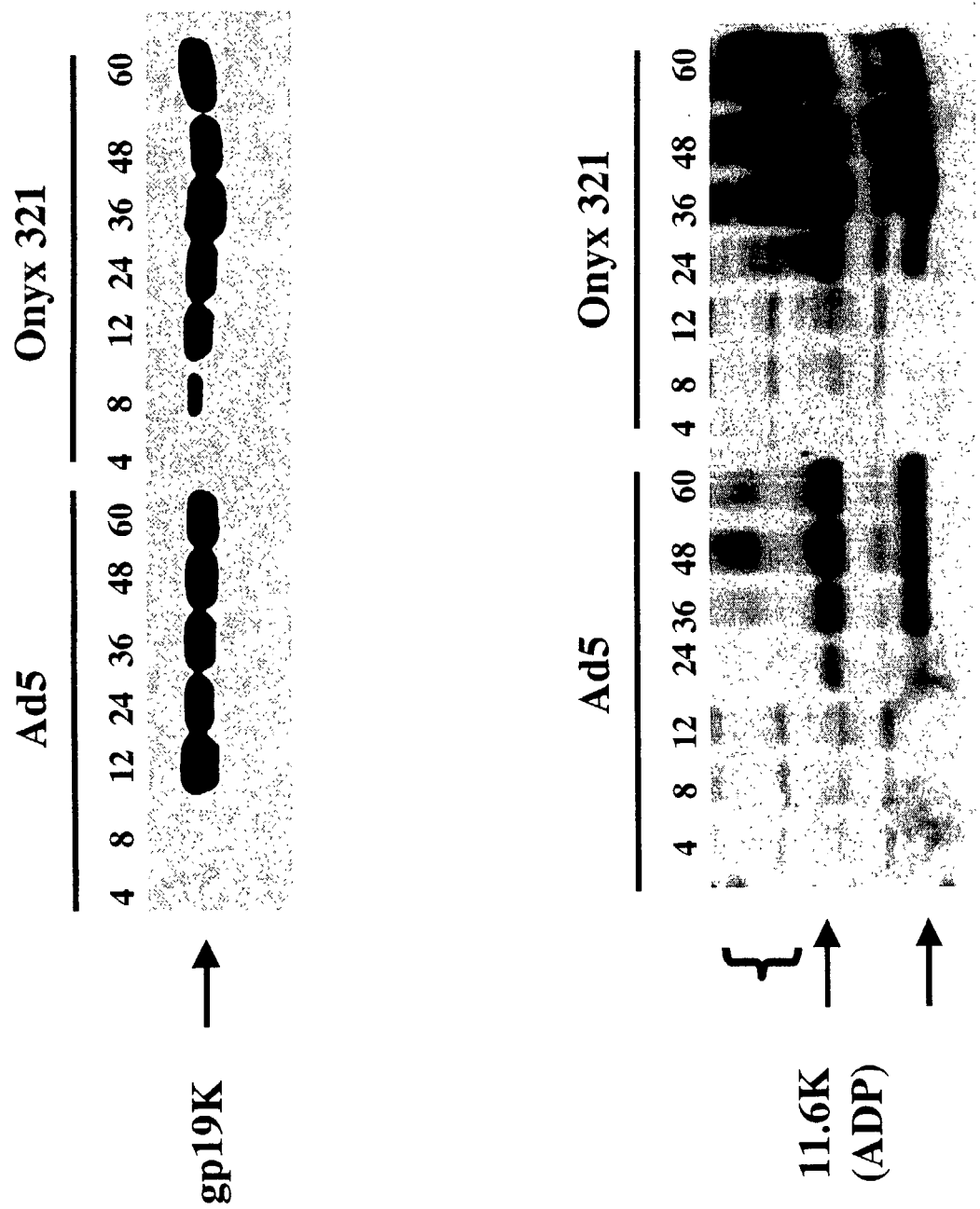
FIG. 30 shows Western blots of the E3 proteins gp19K and 11.6K from cells infected with Ad5 or Onyx 321. The numbers above each lane refer to times post-infection.

Next, mTNF expression was analyzed along with the remaining E3 proteins. These blots are shown in FIGS. 29 and 30. In FIG. 29, mTNF expression was not detected until 24 hr p. i., unlike 2 of the genes it replaced, namely 14.7K and 14.5K, which appear about 8 to 12 hr p. i. In this case, detectable mTNF expression was later than endogenous gene expression since 3 genes were removed, along with endogenous splicing signals. FIG. 30 shows that while gp19K expression remains similar to Ad5, the expression of 11.6K by Onyx 321 is greatly enhanced. Without wishing to be help to any particular theory, it can be speculated that this is the cause for the appearance of the enhanced CPE seen in FIG. 28.

Figure 31:
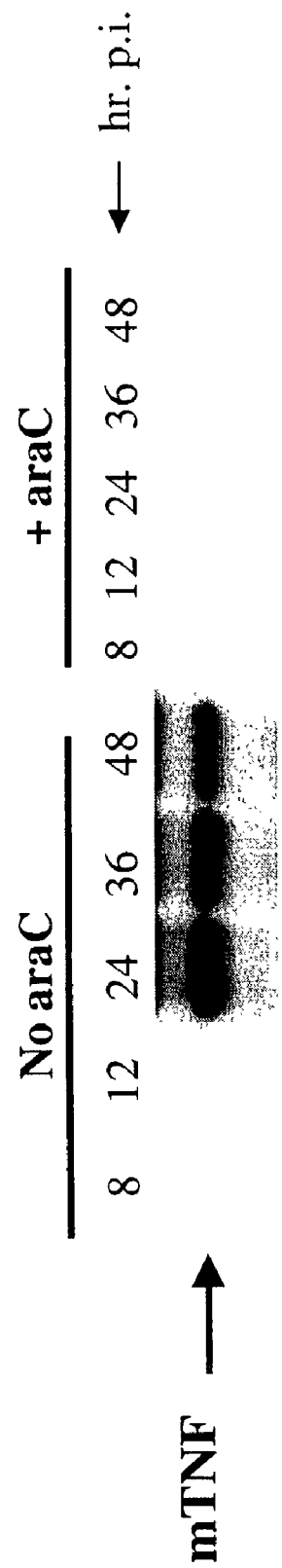
FIG. 31 shows a Western blot of mTNF from cells infected with Onyx 321 incubated in the absence or presence of araC.
Figure 32:
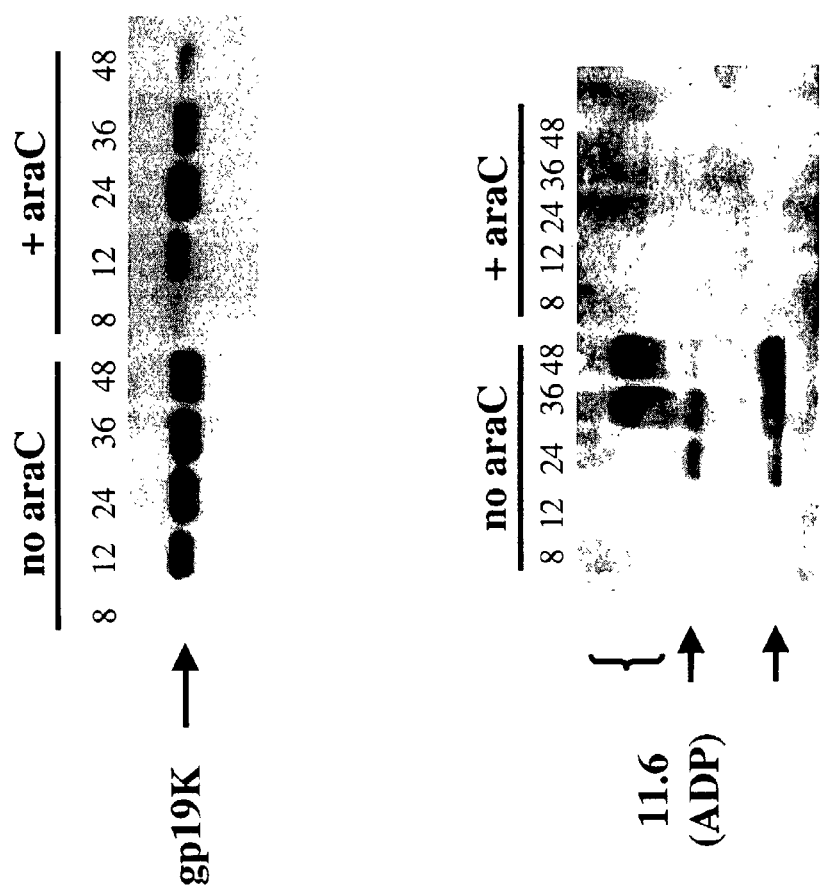
FIG. 32 shows Western blots of the E3 proteins gp19K and 11.6K from cells infected with Onyx 321 either in the absence or presence of araC. The numbers above each lane refer to times post-infection.

Since mTNF did not appear until 24 hr p.i., the question arose if it is being expressed as a late protein? To test this, araC was added to the culture medium and cell lysates were analyzed by Western blot. The results are shown in FIGS. 31 and 32. Murine TNF in the place of E3B appears to be a bona fide late protein as its expression was dependent on DNA replication. As controls, gp 19K expression continued in the presence of araC, while that of 11.6K did not. This represents another region for insertions of heterologous genes that we wish to express predominately during the late phase of infection.

Example 10

Creation of Viruses Containing Genes for Chemokines

The genes for the chemokines hMCP3-alpha and hMIP3 alpha were inserted into the 6.7K/gp19K region and viruses were made. Specifically, the oligonucleotides used to PCR amplify these genes are listed in Table 4; each of these genes were amplified with the NheI site on the 5' end and the MunI site on the 3' end. The MIP3-alpha gene was obtained in the form of an EST from ATCC (EST# 113153) and the EST for MCP3-alpha was obtained from Genome Systems (Image #485989). The plasmid for insertion was pG-E3SV; both the plasmid and the PCR products were cut with NheI and MunI. All fragments were gel purified. Then each of the chemokines was inserted into the vector individually. Viruses were created using these constructs just as described above. The viruses were plaque purified and confirmed by methods described above.

Example 11

Construction of BstLink Virus/TP-DNA

Insertion of a gene of choice into the adenovirus genome is an extensive process. It involves cloning into the smaller plasmids first and then adding this into the larger, pNB-based vectors. Ideally, the smaller plasmids could be used directly. However, their use for co-transfections for virus construction is difficult because it allows a limited amount of overlapping sequences necessary for homologous recombination. For example, there is only a 240 base pair overlap in sequence between the plasmid pSN and genome viral DNA at the 5' end when cutting TP-DNA with EcoRI, the standard method. Thus, to increase the region of overlap, a virus called BstLink was created as follows. The plasmid pG-Bst→Stu was used because it deletes the 11.6K death gene, which, if used to generate viruses, results in much smaller plaques. Thus, this plasmid was digested with MunI, filled in with T4 DNA polymerase, and a BstBI linker was added by ligation. The restriction enzyme site BstBI was chosen because it is not present anywhere else in the Ad5 genome. This was built (an E3 region with no 11.6K and containing the additional BstBI site) into Ad5 (this strategy is applicable to any adenovirus, or other virus where death protein is present). TP-DNA prepared from the virus can then be used for virus construction. This is done by cutting the TP-DNA with BstBI and cotransfecting with the E3 plasmid with the desired alterations. Therefore when selecting recombinant viral plaques that should contain the 11.6K gene (or another death gene), the phenotypic difference between wild type (small plaques) and the recombinant (larger plaques) will make selection of recombinants easier. In addition, this increases the homology at the 5'end to 2273 base pairs; thus overlap recombination can be used for creation of E3 virus mutants. Also recombinant viruses are easier to select based on phenotypic differences. The plaques still have to screened for the mutations, but the proportion of correct virus clones is predicted to be higher because of the advantage of selecting for the correct construct.

Example 12

Construction of Onyx-742

Plasmid pE3SV+V+B, described in U.S. patent application Ser. No. 09/347,604, and on deposit with the American Type Culture Collection Bethesda, Md., USA: ATCC No., was used to construct ONYX-742. This plasmid contains the E3 region of adenovirus. First, pE3SV+V+B was digested with ClaI and SwaI. Next, the cytosine deaminase gene (CD) (pCD2, ATCC No. 40999, Bethesda, Md., USA) was PCR amplified using primers CD-Cla (5'-CCCCCCAAGCT-TATCGATATGTCGAATAAC-3'), and CD-Swa (5'-TC-CCCCGGGATTTAAATTCGTTCAACGTTT-3'). The PCR product was purified and digested with ClaI and SwaI endonucleases, and ligated with pE3SV+V+B to create pE3SV+V+B+CD(C/S). Note that the bacterial start codon of CD, GTG, was replaced with the eukaryotic start codon, ATG, in the primer design.

To facilitate homologous recombination with viral DNA, additional adenovirus sequences were added at the 5' region of pE3 SV+V+B+CD(C/S). The plasmid was digested with SpeI and ligated with the 7533bp fragment isolated from pNB following digestion with NheI (19549) and SpeI (27082) endonucleases to generate pNB-CD(C/S). pNB is described in U.S. patent application Ser. No. 09/347,604. Orientation of inserted DNA was confirmed by restriction digest since NheI and SpeI are compatible cohesive ends.

Lastly, Onyx-742 was produced by homologous recombination using viral TP-DNA from ONYX-015, which was digested with EcoRI (Hermiston TW, et al. In: Wold WSM (ed.). *Adenovirus Methods and Protocols*. Humana Press: Totowa, N.J., 1999, pp 11-24). Next, pNB-CD(C/S) was digested with BamHI, and the digested plasmid and TP-DNA were co-transfected in A549 cells using Lipofectamine as described by the manufacturer (Life Technologies). Recombinant virus, ONYX-742, was triple plaque purified and confirmed by PCR-sequencing using methods described previously (Hawkins LK et al. *Gene Therapy* 2001; 8: 1123-1131). Viral DNA from CsCl purified ONYX-742 was confirmed by PCR analysis and DNA sequencing of the entire E1 and E3 region.

Example 13

Expression of Cytosine Deaminase in Onyx-742 In Vitro and In Vivo

In Vitro Expression of CD

Figure 33:
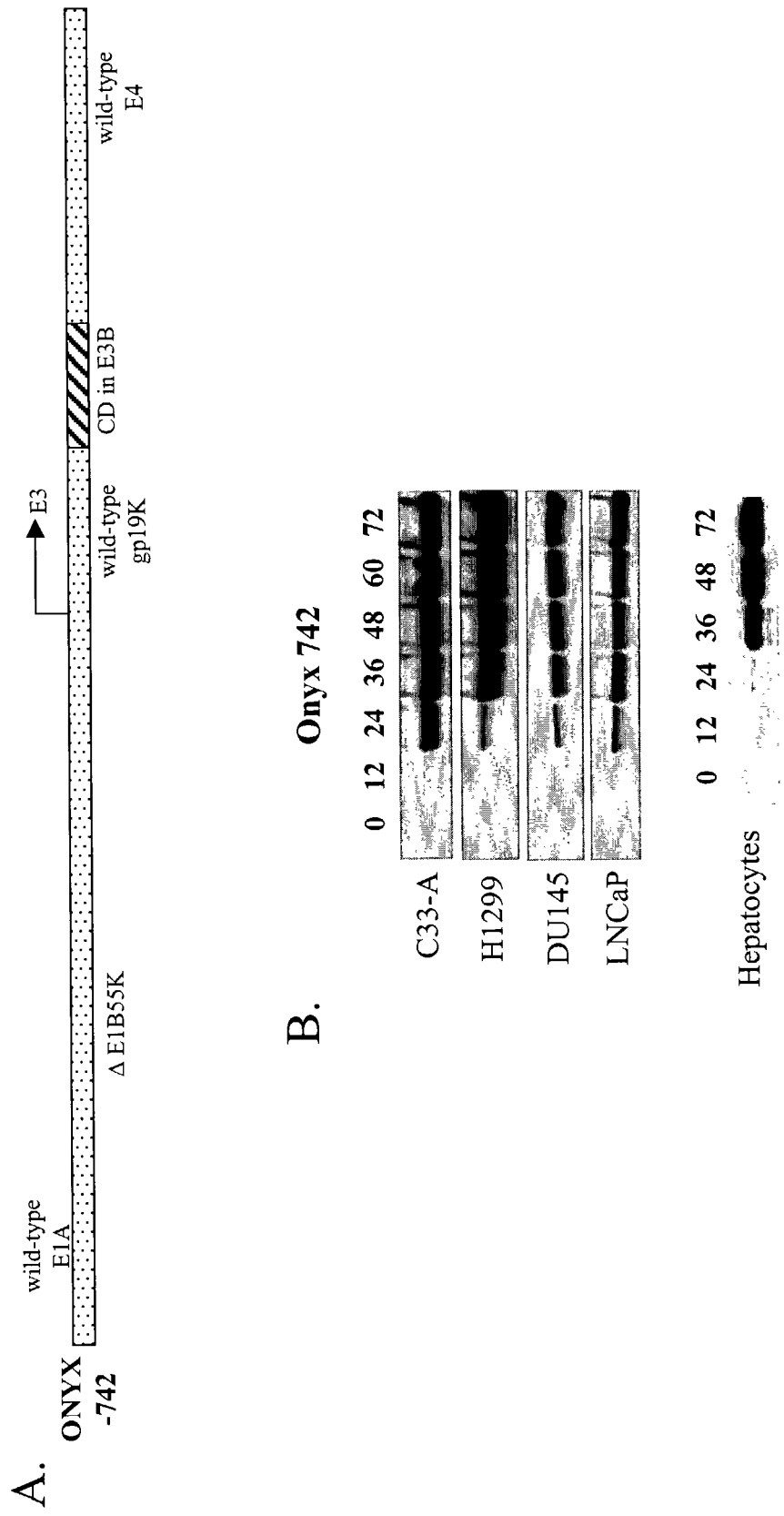
FIG. 33(A) shows the genomic structure of ONYX-742. ONYX-742 has the *E. coli* CD gene inserted in the E3B region of ONYX-015. Panel (B) shows the in vitro CD expression in cells infected with ONYX-742. Human cancer cell lines and cultured normal human hepatocytes were infected at an MOI of 1 pfu/cell. At indicated time points, cell extracts were prepared and CD protein levels were analyzed by immunoblotting analysis.

Expression of CD was measured in cultured tumor cells (C33A, H1299, DU145 and LNCaP) and primary normal human cells (human hepatocytes, quiescent small airway epithelial cells and mammary epithelial cells) following infection with ONYX-742 (FIG. 33B). At an MOI of 1, cancer cells infected with ONYX-742 expressed readily detectable levels of CD at 24 hours post infection. The amount of CD protein increased with time, reaching a maximum level at 72 hours post infection. In normal human hepatocytes infected with ONYX-742, CD expression was modestly delayed, producing detectable levels of CD at 36 hours post infection. Similar results were obtained from quiescent as well as proliferating normal human small airway epithelial cells and mammary epithelial cells. The CD expression pattern following ONYX-742 infection was consistent with the differential replication of the parental ONYX-015 and normal cells. The CD expressed in these experiments was functional, capable of converting 5-FC to 5-FU in vitro.

Briefly, immunoblotting for cultured cells or tumors was conducted as follows. Cultured cells were infected with at an MOI of 1. At indicated times post-infection, the cells were lysed in 100 mM Tris-Cl [pH 6.8], 5 mM EDTA, 1% SDS, 5% β-mercaptoethanol. For the animal studies, tumor samples were flash frozen and powderized in liquid nitrogen, and subsequently dissolved in the same lysis buffer. Cells debris was removed by centrifugation, and soluble proteins were fractionated by electrophoresis on (12%) pre-cast protein gels (BioWhitaker). After electrophoresis, the proteins were electrophoretically transferred to PVDF membranes. Blots were then incubated with antibodies diluted in PBS containing 1% dry milk and 0.1% Tween-20, and visualized by ECL (Amersham). Anti-CD antibody was diluted 1:50,000; rabbit anti-fiber antibody (American Qualex) was diluted 1:1000.

In Vivo CD Expression Following Intravenous Virus Administration

Figure 34:
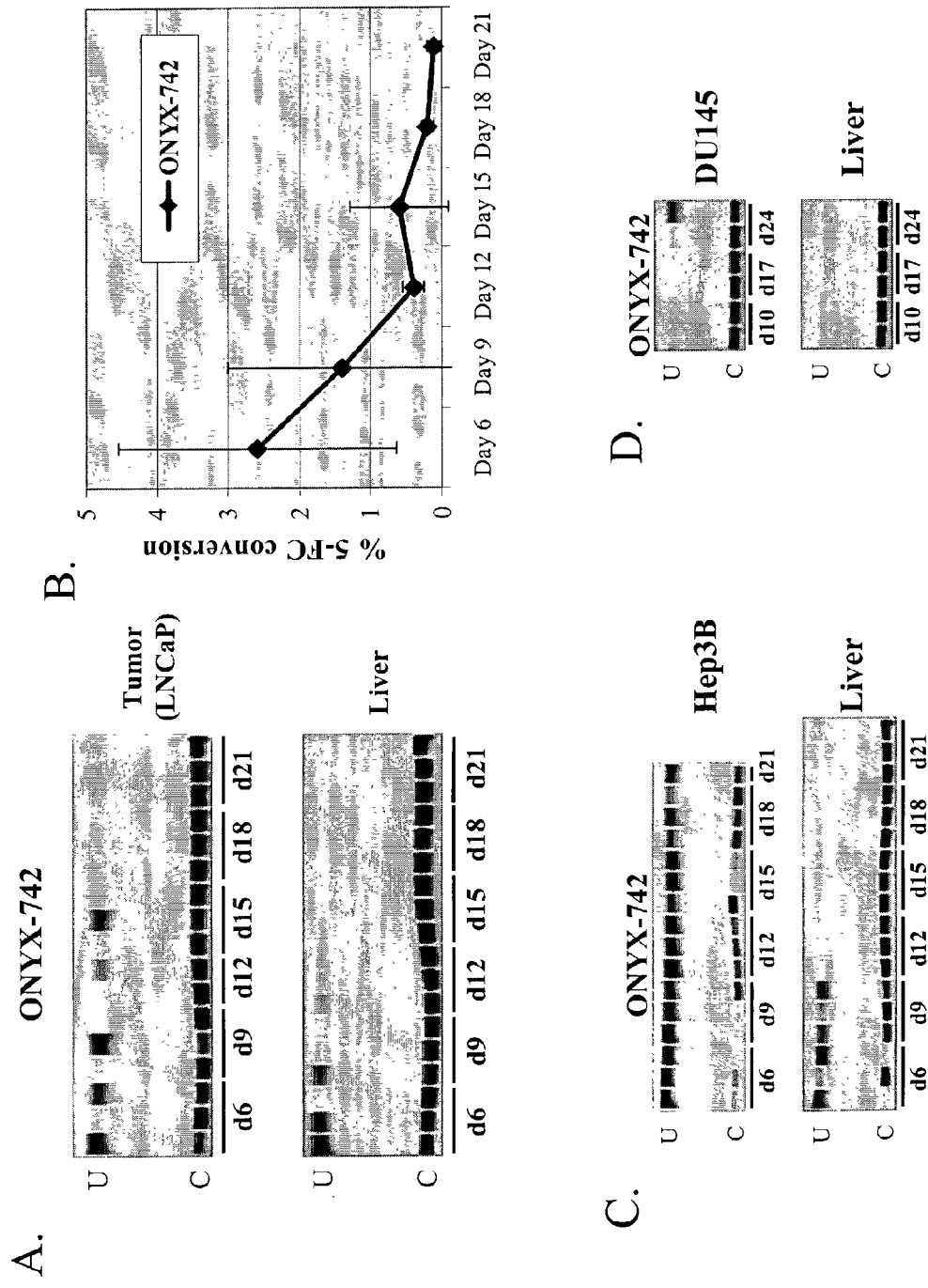
FIG. 34 shows CD expression in LNCaP xenograft tumors and liver following intravenous injection of ONYX742. Panel (A): Viruses were administrated intravenously through tail vein injection into nude mice bearing LNCaP xenograft tumors. Five consecutive daily injections were given to each animal at a dose of $2\times10^8$ pfu per day. At indicated time points (in days, d), animals were sacrificed, tumors and livers were removed and analyzed for CD enzymatic activity using a $^{14}$C-cytosine-to-uracil conversion assay. The first day of virus administration was defined as Day 1. C: $^{14}$C-cytosine, U: $^{14}$C-uracil. Each lane represents an individual animal. Top panels: CD activity in LNCaP xenograft tumors. Bottom panels: CD activity in the corresponding mouse livers. 50 µg of total protein was used in each reaction. Panel (B): CD activity was quantified using an assay that converts $^{14}$C-5-fluorocytosine (5-FC) to 5-fluorouracil (5-FU). The amount of 5-FC and 5-FU was determined using a PhosphoImager, and percentage of the input 5-FC that was converted to 5-FU was plotted. The remaining panels, C and D, show CD expression in Hep3B and DU145 tumor xenografts and the corresponding liver following intravenous injection of ONYX742. Virus injection and animal sample analysis were performed as described in FIG. 34A. In the Hep3B study, both ONYX-742 was dosed at $2\times10^8$ pfu per day for 5 consecutive days. In the DU145 study, ONYX-742 was dosed at $2\times10^8$ pfu per day for 5 consecutive days. At indicated time points (in days, d), animals were sacrificed, tumors and livers were removed and analyzed for CD enzymatic activity. Each lane represents an individual animal.

Next we injected ONYX-742 intravenously via the tail vein into nude mice carrying human tumor xenografts, and examined CD activity in xenograft tumors and in normal tissues such as liver, lung and spleen. Typically, tumors were established in nude mice through subcutaneous injection of $2\times10^6$ tumor cells. When tumors reached an average size of 100 mm$^3$, viruses were administrated intravenously through tail vein injection. For all animal models, each animal was given 5 consecutive daily injections at a dose of 2×10⁸ pfu per day. The first day of virus administration was defined as Day 1. Data from the LNCaP xenograft model are shown in FIG. 34A. Animals were sacrificed at indicated time points and their tumor and normal tissue samples were analyzed for CD activity using a cytosine to uracil conversion assay. Tumor CD activity was substantial on day 6, the first time point tested, and decreased with time. By day 18, virtually no CD activity was detected. These data were confirmed doing quantiative assays as shown in FIG. 34B.

CD expression following intravenous virus inoculation was also evaluated in other xenograft mouse models, including Hep3B, DU145 and C33A. ONYX-742 produced persistent CD activity in the Hep3B tumors (FIG. 34C), possibly due to good replication of the parental virus ONYX-015 in this tumor model. The C33A tumor expression pattern was similar to that of the Hep3B model. In DU145 tumors, ONYX-742 generated low CD expression (FIG. 34D). Animals that received ONYX-742 displayed modest but transient CD activity in the liver, which peaked between days 6 and 9 (note that the first time point in the DU145 study is day 10). Lung and spleen tissues displayed very similar CD expression profiles as the liver following intravenous injection.

Briefly, the CD assay was conducted as follows. Tumor and liver samples were flash frozen and powderized in liquid nitrogen. Twenty to forty milligrams of the tissue powder was lysed in 20 mM Tris-Cl, pH8.0, 0.15 M NaCl, and 1% Triton X-100, and subsequently frozen and thawed for three times. For cytosine and 5-FC conversion assays, 200 µg of protein extract was incubated with [2-$^{14}$C] cytosine or [2-$^{14}$C] 5-fluorocytosine (1 µCi/mmol; Moravek Biochemicals, Brea, Calif.). The reactions were typically incubated for 2 hours at 37° C. Reaction products were separated on thin layer chromatography plates (VWR) and visualized by autoradiography.

Figure 35:
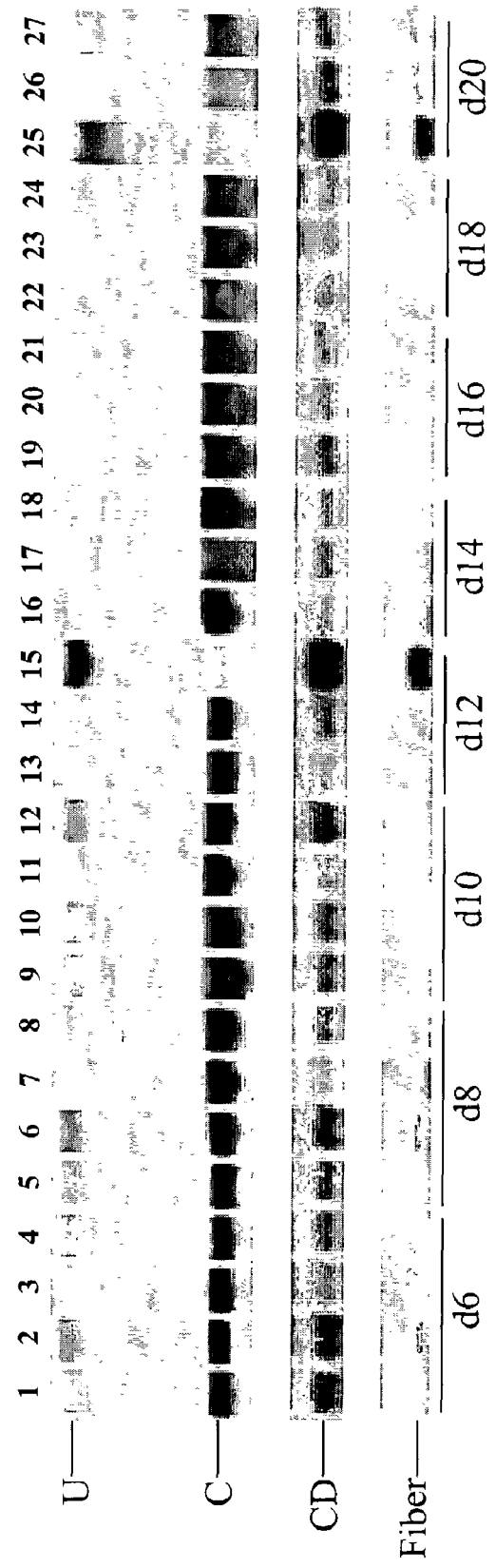
FIG. 35 show the correlation between CD enzymatic activity, CD protein level and adenovirus fiber expression. Nude mice bearing C33A tumors were injected intravenously with ONYX-742 as described in FIG. 34A. At indicated time points, tumor samples were removed and analyzed for CD enzymatic activity using the cytosine-to-uracil conversion assay, CD and adenovirus fiber protein levels by immunoblotting analysis.

Correlation between CD expression and viral replication. To determine whether Onyx-742 CD activity accurately reflected the CD protein expression level, we analyzed tumor samples from one typical experiment for both CD activity and CD protein level. As shown in FIG. 35, there was a good correlation between CD enzymatic activity and CD protein (for example, see lanes 2, 6, 12, 15 and 25), indicating the CD activity assay truly reflected the CD gene expression level. We further determined if CD gene expression correlated with the replication of the viral vectors. Fiber is a late viral protein whose expression is strictly dependent upon viral DNA replication, and is often used as a marker for adenovirus replication. Therefore we examined adenovirus fiber expression in the same tumor samples (FIG. 35). Indeed, there was a good correlation between CD activity and fiber expression. For example, lanes 15 and 25 had robust CD activity, and fiber protein was expressed at high levels; lanes 16 to 24 had little CD activity, and fiber expression was undetectable. These results indicate that CD expression was directly correlated with replication of the viral vectors. This was also confirmed by observations that CD expression also correlated well with the level of adenovirus DNA replication.

Example 14

Adenoviral Vector with Two Heterologous Genes Construction of Onyx-372

An adenoviral vector was generated, Onyx 372, that has the E3 early genes 6.7K and gp19K, and the late gene, ADP, deleted. In the place of the 6.7K and gp19K genes was substituted hMCP-3, and mTNF was substituted in the place of the ADP gene. Certain of the materials and methods used to generate this virus are described in the preceding examples, and in Hawkins, L. K., et al., Gene Ther, 2001. 8(15): p. 1123-31; Hawkins, L. K. and T. W. Hermiston, Gene Ther, 2001. 8(15): p. 1132-41; and Hawkins, L. K. and T. Hermiston, Gene Ther, 2001. 8(15): p. 1142-8. This includes the adenovirus Onyx-320, and Onyx-323, which has mTNF in place of the 6.7K/gp19K region. Onyx-371, which has hMCP, inserted in the 6.7K/gp19K region was generated in a similar fashion as Onyx-323.

The gene for human MCP-3 (hMCP-3) was inserted into the shuttle plasmid, pSN-PNPS, using the restriction sites NheI (a restriction site engineered at position 28532 in the Ad5 genome) and MunI (endogenous restriction site at position 29355). These sites encompass the Ad5 E3 genes coding for the 6.7K and gp19K proteins, and allow for their deletion and subsequent heterologous gene insertion. The MCP3 gene was amplified by PCR from the plasmid pORF-hMCP-3 (InvivoGen, San Diego, Calif.) using the primers:

MCP3  5'-GCGCGCTAGCCCACCATGTGGAAGC-CCATGCCCTCACC-3', and

MCP3  5'-GGCCCAATTGTCAAAGCTTTG-GAGTTTGGGTTTTCTTG-3'

The PCR product, and the plasmid pSN-PNPS were digested with NheI and MunI and ligated together to create the plasmid pSN-MCPNheMun. All plasmids were confirmed by sequencing and the recombinant virus was made as previously described (Hawkins, L. K., et al., Gene Ther, 2001. 8(15): p. 1123-31).

Figure 36:
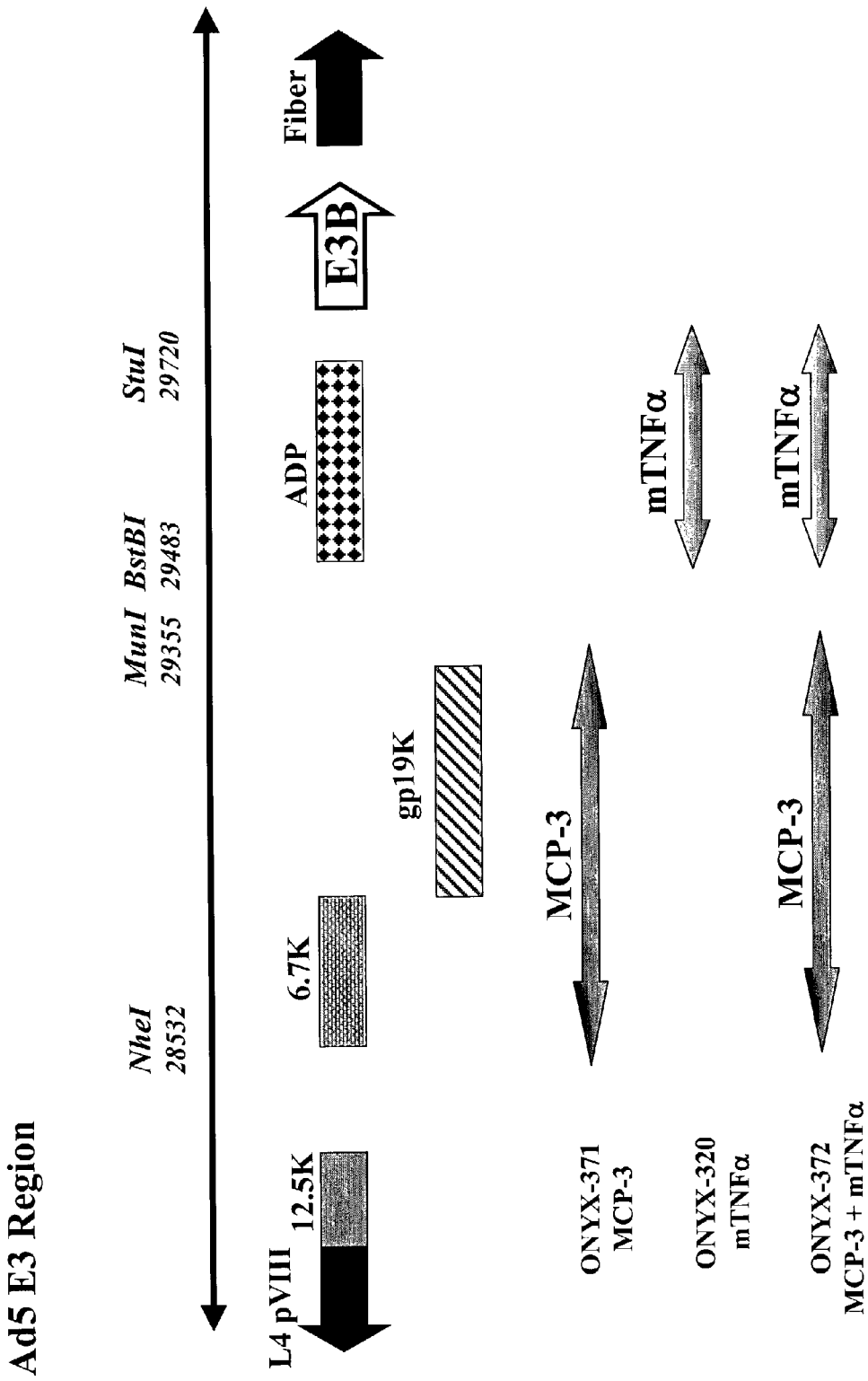
FIG. 36 shows a diagram of adenoviral vector construction of the Ad5 E3 region transcription unit, adjacent regions and viruses described herein. The restriction sites that were used for cloning hMCP-3 and/or mTNF are shown above the line and the corresponding nucleotide number relative to the Ad5 genome is indicated. The boxes listed below the line indicate the genes for identified proteins in the E3 region. They include the 3' end of the L4 message for pVIII, 12.5K, gp19K, ADP, and the remaining genes in the E3B region (RID α, RIDβ, and 14.7K) are downstream. The viruses used in this study have heterologous genes in place of some of the E3 endogenous genes. ONYX-320 carries mTNF in place of ADP. ONYX-371 carries MCP-3 instead of 6.7K and gp19K genes. And ONYX-372 carries both of these heterologous genes in the same relative positions.

To construct the double heterologous-containing shuttle plasmid for virus construction, the plasmids pSN-mTNFBst-Stu (Hawkins, L. K. and T. W. Hermiston, Gene Ther, 2001. 8(15): p. 1132-41), and pSN-MCPNheMun were cut with MunI and SunI and the fragment of the latter plasmid was ligated into the former plasmid. This shuttle plasmid, pSN-MCPNheMunTNFBstStu, was then used to make the recombinant virus ONYX-372 that contains the MCP-3 gene in place of the E3 6.7/gp19K genes and the murine TNFα gene in place of the E3 ADP gene. The various viruses and their gene insertion sites into the E3 region are represented diagrammatically in FIG. 36. All viruses were plaque-purified, screened, and propagated as previously described [Hawkins, L. K., et al., Gene Ther, 2001. 8(15)].

Example 15

Expression of hMCP-3 and mTNF from Onyx-372

The expression of heterologous genes from the newly generated viruses, ONYX-371, and more particularly, ONYX-372, was analyzed by western blot and quantitated by ELISA. The purpose of this experiment was to determine the relative timing and strength of gene expression of the newly inserted therapeutic heterologous genes.

Briefly, to measure the amount of mTNF or MCP-3 released into the culture medium, the cells were infected and incubated for the indicated amounts of time (Hawkins, L. K., et al., Gene Ther, 2001. 8(15): p. 1123-31). One hour prior to each time point, the medium was removed, the cells were washed once, and new medium was added. After one hour, aliquots of the culture medium were removed and analyzed by ELISA. Each time point was done using four replicates and the experiment was performed twice. The results of one representative experiment are shown. For quantitation of mTNF and MCP-3, the Cytoscreen mTNF or hMCP-3 ELISA kits were used as recommended by the manufacturer (BioSource International, Camarillo, Calif.).

The genes expressed from these two regions differ dramatically in their expression patterns in the viral life cycle; as mentioned above, the 6.7K/gp19K is an early gene, expressed 8-12 hr p.i. in Ad5 infected A549 cells (FIG. 37A). ADP is a late protein, expressed after the initiation of viral replication, approximately 24 hr p.i. in Ad5 infected A549 cells (FIG. 2B). In the parent viruses and in previous viruses developed using this approach, the inserted heterologous gene was expressed in a pattern that reflected the gene it replaced (Hawkins, L. K., et al., Gene Ther, 2001. 8(15): p. 1123-31; Hawkins, L. K. and T. W. Hermiston, Gene Ther, 2001. 8(15): p. 1132-41; and Hawkins, L. K. and T. Hermiston, Gene Ther, 2001. 8(15): p. 1142-8. To ensure that this is also the case here when inserting multiple genes, MCP-3 and mTNF protein expression was examined by Western blot analysis.

Briefly, Western blot analysis was performed as described previously (Hawkins, L. K., et al., Gene Ther, 2001. 8(15): p. 1123-31). The E3 protein antibodies were a kind gift from Dr. W S M Wold. The antibody for murine TNFα (mTNF) was obtained from R&D Systems (Minneapolis, Minn.) and The antibody for MCP-3 was obtained from PeproTech (Rocky Hill, N.J.). Both were used as recommended by the manufacturers. For western blot analysis of mTNF or MCP-3 secreted into the cell culture medium, a 25 µl aliquot of the conditioned medium was used at the indicated time post infection.

The expression of the MCP-3 from ONYX-371 (MCP-3 inserted into the 6.7K/gp19K region) and ONYX-372 (MCP-3 and mTNF inserted into 6.7K/gp19K region and ADP regions, respectively) was studied by Western blot analysis and compared to the timing of gp19K expression in Ad5 infected A549 cells. As seen in FIG. 37A, expression of MCP-3 in the supernatant from both the ONYX-371 and ONYX-372 infected cells paralleled the expression of gp19K seen from the Ad5 infected A549 cells. In FIG. 37B, mTNF expression timing was examined from ONYX-320 (insertion of mTNF into the ADP region) and ONYX-372 (MCP-3 insertion into the 6.7K/gp19K region and mTNF into the ADP region) and compared to the timing of ADP expression in Ad5 infected A549 cells. Consistent with expression of ADP from Ad5, mTNF was not detected in the culture supernatant until late times post-infection (24 hr p.i.) from both ONYX-320 and ONYX-372. Therefore, the expression of both the MCP-3 and mTNF heterologous genes is substantially similar to the expression timing patterns of the gp19K and ADP proteins in both the single and combination heterologous gene expressing viruses.

To ask whether the quantities of the heterologous genes in the double gene virus, ONYX-372, were similar to the levels seen with the single heterologous gene containing viruses, ONYX-320 and ONYX-371, MCP-3 and mTNF levels were quantitated by ELISA. This assay was performed in such a way as to measure de novo expression and secretion into the culture medium within a one hour time frame preceding the indicated times p.i. In FIG. 38, MCP-3 expression from the single gene insertion virus ONYX-371 was detected at 8 hours p.i., peaked at 36 hours, then declined. The expression of MCP-3 from 372-infected cells followed the same time course; however, its quantity appears to be approximately one-half the level seen with the single gene expressing virus, ONYX-371. A similar result was seen for the expression of mTNF (FIG. 39). The mTNF expression from ONYX-320-infected cells peaked at 36 hr p.i., consistent with expression in the late phase of the viral life cycle. The expression from ONYX-372 was less than the parental virus, ONYX-320. The relative attenuation of the expression of MCP3 was greater than that for mTNF.

Example 16

Expression of Ad5 E3 Genes with Heterologous Genes in Onyx-372

Experiments were conducted to determine the expression of the remaining E3 genes in the heterologous gene containing viruses ONYX-371 and ONYX-372. A549 cells were infected at an MOI of 10 pfu/cell and harvested at 8, 12, 24, 36, 48, and 60 hours post infection. Protein extracts were generated and Western blot analysis was performed. FIG. 40 shows expression of the E3 proteins gp19K, ADP, RIDβ, and 14.7K; also shown is fiber from the L5, or late 5, transcription unit. The detection of fiber was included to monitor any effects on the expression of the L5 region that lies downstream of E3 region (see FIG. 36). As previously described, the expression of gp19K is not altered in ONYX-320 infected cells (FIG. 40A, Hawkins, L. K. and T. W. Hermiston, Gene Ther, 2001. 8(15): p. 1132-41).

The insertion of MCP-3 into the 6.7K/gp19K region did not alter the timing of expression of the downstream (FIG. 36) ADP gene (FIG. 40B). Further, the expression of the E3B proteins (RIDβ, 14.7K) is maintained in all the recombinant viruses tested though the levels of the E3B proteins may be slightly reduced relative to the expression levels seen in the Ad5 infected cells (see FIGS. 40C and 40D). The expression of fiber does not appear to be altered in any of the viruses (FIG. 40E). Therefore, the expression of the remaining E3 genes is maintained in the single and multi-gene expressing viruses though the relative levels of gene expression may be slightly lower from the E3B region.

Example 17

Effect of Heterologous Genes on Onyx-372 Life Cycle

Experiments were done to determine what, if any, effect the presence of hMCP-3 and mTNF in Onyx-372 has on its life cycle relative to other adenoviruses, including wild type adenovirus. Specifically, the question asked was; what effect does the heterologous genes have on the cytopathic effect of the virus? Briefly, the appearance of cytopathic effect (CPE) caused by the virus is a measure of the progression of the viral life cycle in the infected cell. The deletion of ADP has been previously shown to delay CPE and virus release significantly with a concomitant increase in single heterologous gene expression time as the metabolic activity of the infected cell is extended Hawkins, L. K. and T. W. Hermiston, Gene Ther, 2001. 8(15): p. 1132-41; Tollefson, A. E., et al., Virology, 1996. 220(1): p. 152-62; and, Tollefson, A. E., et al., J Virol, 1996. 70(4): p. 2296-306. Consequently, ONYX-372 (6.7K/gp19K, ADP deleted) infected cells would be expected to display a delay in the appearance of CPE, similar to ONYX-320 (ADP deleted) infected cells relative to wild type Ad5. FIG. 41 shows that this is the case. Most importantly, the delay in CPE associated with ADP deleted from ONYX-372 does not compromise the ability of the virus to generate infectious progeny as shown in FIG. 42.

Burst assays were quantitated using an ELISA and performed as described previously, and the methodology associated with the CPE analysis has also been previously described in Hawkins, L. K. and T. W. Hermiston, Gene Ther, 2001. 8(15): p. 1132-41; and Hawkins, L. K. and T. Hermiston, Gene Ther, 2001. 8(15): p. 1142-8.

The invention now being fully described, it will be apparent to one of ordinary skill in the art that many changes and modifications can be made thereto without departing from the spirit or scope of the appended claims.

We claim:

1. A composition of matter comprising a replication competent recombinant adenoviral vector that has restriction sites in the E3 region that facilitate the deletion of early region genes of the E3 region, which early region genes encode proteins selected from the group consisting of 10.4K, 14.5K, 14.7K, 11.6K, 6.7K and gp19K, wherein following said deletion and substitution of said early region genes with heterologous genes, endogenous adenoviral transcription regulatory sequences are maintained and the heterologous genes exhibit an expression pattern similar to the endogenous adenoviral genes that they replace, both in terms of timing and degree of expression.

2. A composition of matter as described in claim 1 wherein said early region genes of the E3 region that encode the 6.7K and gp19K proteins are deleted together.

3. A composition of matter as described in claim 1 wherein said early region genes of the E3 region that encode the 10.4K, 14.5K, and 14.7K proteins are deleted together.

4. A composition of matter comprising a replication competent recombinant adenovirus, said adenovirus having restriction sites in the E3 region that facilitate the deletion of early region genes of the E3 region, which early region genes encode proteins selected from the group consisting of 10.4K, 14.5K, 11.6K, 6.7K, 14.7K and gp19K, and wherein following said deletion and substitution of said early region genes with heterologous genes, endogenous adenoviral transcription regulatory sequences are maintained and the heterologous genes exhibit an expression pattern similar to the endogenous adenoviral genes that they replace, both in terms of timing and degree of expression.

5. A composition of matter as described in claim 4 wherein said early region genes of the E3 region that encode the 6.7K and gp19K proteins are deleted together.

6. A composition of matter as described in claim 5 wherein said early region genes of the E3 region that encode the 10.4K, 14.5K, and 14.7K proteins are deleted together.

7. A composition of matter as described in claim 1 wherein said early region gene of the E3 region that encodes the 11.6K protein is deleted.

8. A composition of matter as described in claim 4 wherein said early region gene of the E3 region that encodes the 11.6K protein is deleted.

* * * * *

SEQUENCE LISTING

<160> NUMBER OF SEQ ID NOS: 33

<210> SEQ ID NO 1
<211> LENGTH: 27
<212> TYPE: DNA
<213> ORGANISM: Artificial Sequence
<220> FEATURE:
<223> OTHER INFORMATION: Adenovirus

<400> SEQUENCE: 1
cctctccgag ctcagctact ccatcag                                          27

<210> SEQ ID NO 2
<211> LENGTH: 27
<212> TYPE: DNA
<213> ORGANISM: Artificial Sequence
<220> FEATURE:
<223> OTHER INFORMATION: Adenovirus

<400> SEQUENCE: 2
ggaggtgagc ttaattaacc cttaggg                                          27

<210> SEQ ID NO 3
<211> LENGTH: 27
<212> TYPE: DNA
<213> ORGANISM: Artificial Sequence
<220> FEATURE:
<223> OTHER INFORMATION: Adenovirus

<400> SEQUENCE: 3
ccctaagggt taattaagct cacctcc                                          27

<210> SEQ ID NO 4
<211> LENGTH: 26
<212> TYPE: DNA
<213> ORGANISM: Artificial Sequence
<220> FEATURE:
<223> OTHER INFORMATION: Adenovirus

<400> SEQUENCE: 4
gattaaatga gatatcattc ctcgag                                           26

<210> SEQ ID NO 5
<211> LENGTH: 26
<212> TYPE: DNA
<213> ORGANISM: Artificial Sequence
<220> FEATURE:
<223> OTHER INFORMATION: Adenovirus

<400> SEQUENCE: 5
ggcggtgtcc ggtggtatta ctgtcg                                           26

<210> SEQ ID NO 6
<211> LENGTH: 33
<212> TYPE: DNA
<213> ORGANISM: Artificial Sequence
<220> FEATURE:
<223> OTHER INFORMATION: Adenovirus

<400> SEQUENCE: 6
gggtattagg ccaaaggcgc agctagcgtg ggg                                   33

<210> SEQ ID NO 7
<211> LENGTH: 29

```
<212> TYPE: DNA
<213> ORGANISM: Artificial Sequence
<220> FEATURE:
<223> OTHER INFORMATION: Adenovirus

<400> SEQUENCE: 7
cccaaacaat gaaggcctcc atagattgg                                    29

<210> SEQ ID NO 8
<211> LENGTH: 26
<212> TYPE: DNA
<213> ORGANISM: Artificial Sequence
<220> FEATURE:
<223> OTHER INFORMATION: Adenovirus

<400> SEQUENCE: 8
cagctacttt aatattacag gaggag                                       26

<210> SEQ ID NO 9
<211> LENGTH: 32
<212> TYPE: DNA
<213> ORGANISM: Artificial Sequence
<220> FEATURE:
<223> OTHER INFORMATION: Adenovirus

<400> SEQUENCE: 9
gcgacccacc ctttcgaaca gagatgacca ac                                32

<210> SEQ ID NO 10
<211> LENGTH: 32
<212> TYPE: DNA
<213> ORGANISM: Artificial Sequence
<220> FEATURE:
<223> OTHER INFORMATION: Adenovirus

<400> SEQUENCE: 10
ggagacgact gacaccctgg atccagaaat gg                                32

<210> SEQ ID NO 11
<211> LENGTH: 18
<212> TYPE: DNA
<213> ORGANISM: Artificial Sequence
<220> FEATURE:
<223> OTHER INFORMATION: Adenovirus

<400> SEQUENCE: 11
cacatcgatg tagactgc                                                18

<210> SEQ ID NO 12
<211> LENGTH: 18
<212> TYPE: DNA
<213> ORGANISM: Artificial Sequence
<220> FEATURE:
<223> OTHER INFORMATION: Adenovirus

<400> SEQUENCE: 12
gcagtctaca tcgatgtg                                                18

<210> SEQ ID NO 13
<211> LENGTH: 24
<212> TYPE: DNA
<213> ORGANISM: Artificial Sequence
<220> FEATURE:
<223> OTHER INFORMATION: Adenovirus

<400> SEQUENCE: 13
```

-continued tagaatagggtttaaaccccccgg 24

<210> SEQ ID NO 14
<211> LENGTH: 24
<212> TYPE: DNA
<213> ORGANISM: Artificial Sequence
<220> FEATURE:
<223> OTHER INFORMATION: Adenovirus

<400> SEQUENCE: 14 ccgggggggtttaaaccctattcta 24

<210> SEQ ID NO 15
<211> LENGTH: 31
<212> TYPE: DNA
<213> ORGANISM: Artificial Sequence
<220> FEATURE:
<223> OTHER INFORMATION: Adenovirus

<400> SEQUENCE: 15 ctcaaagatcttattccatttaaataataaa 31

<210> SEQ ID NO 16
<211> LENGTH: 31
<212> TYPE: DNA
<213> ORGANISM: Artificial Sequence
<220> FEATURE:
<223> OTHER INFORMATION: Adenovirus

<400> SEQUENCE: 16 tttattatttaaatggaataagatctttgag 31

<210> SEQ ID NO 17
<211> LENGTH: 36
<212> TYPE: DNA
<213> ORGANISM: Artificial Sequence
<220> FEATURE:
<223> OTHER INFORMATION: Adenovirus

<400> SEQUENCE: 17 gtgagcttaattaaggctagcaatgtcgaataacgc 36

<210> SEQ ID NO 18
<211> LENGTH: 36
<212> TYPE: DNA
<213> ORGANISM: Artificial Sequence
<220> FEATURE:
<223> OTHER INFORMATION: Adenovirus

<400> SEQUENCE: 18 gtgagcatttaaatcagtcgttcaacgtttgtaatc 36

<210> SEQ ID NO 19
<211> LENGTH: 29
<212> TYPE: DNA
<213> ORGANISM: Artificial Sequence
<220> FEATURE:
<223> OTHER INFORMATION: Adenovirus

<400> SEQUENCE: 19 gctgcaagtgctgcacatggggctgcatg 29

<210> SEQ ID NO 20
<211> LENGTH: 36
<212> TYPE: DNA
<213> ORGANISM: Artificial Sequence

```
<220> FEATURE:
<223> OTHER INFORMATION: Adenovirus

<400> SEQUENCE: 20
gtgagcttaa ttaaggctag caatgtcgaa taacgc                                36

<210> SEQ ID NO 21
<211> LENGTH: 36
<212> TYPE: DNA
<213> ORGANISM: Artificial Sequence
<220> FEATURE:
<223> OTHER INFORMATION: Adenovirus

<400> SEQUENCE: 21
gtgagcgttt aaacagtcgt tcaacgtttg taatcg                                36

<210> SEQ ID NO 22
<211> LENGTH: 32
<212> TYPE: DNA
<213> ORGANISM: Artificial Sequence
<220> FEATURE:
<223> OTHER INFORMATION: Adenovirus

<400> SEQUENCE: 22
ggccgctagc ggctaacaat gtcgaataac gc                                    32

<210> SEQ ID NO 23
<211> LENGTH: 35
<212> TYPE: DNA
<213> ORGANISM: Artificial Sequence
<220> FEATURE:
<223> OTHER INFORMATION: Adenovirus

<400> SEQUENCE: 23
gtgagccgta cgaggctagc aatgtcgaat aacgc                                 35

<210> SEQ ID NO 24
<211> LENGTH: 35
<212> TYPE: DNA
<213> ORGANISM: Artificial Sequence
<220> FEATURE:
<223> OTHER INFORMATION: Adenovirus

<400> SEQUENCE: 24
gtgagccaat tgcagtcgtt caacgtttgt aatcg                                 35

<210> SEQ ID NO 25
<211> LENGTH: 33
<212> TYPE: DNA
<213> ORGANISM: Artificial Sequence
<220> FEATURE:
<223> OTHER INFORMATION: Adenovirus

<400> SEQUENCE: 25
gcgcttcgaa gtggaggcta acaatgtcga ata                                   33

<210> SEQ ID NO 26
<211> LENGTH: 33
<212> TYPE: DNA
<213> ORGANISM: Artificial Sequence
<220> FEATURE:
<223> OTHER INFORMATION: Adenovirus

<400> SEQUENCE: 26
ggccaggcct ctaagctcgc tgtaacccag tcg                                   33
```

<210> SEQ ID NO 27
<211> LENGTH: 34
<212> TYPE: DNA
<213> ORGANISM: Artificial Sequence
<220> FEATURE:
<223> OTHER INFORMATION: Adenovirus

<400> SEQUENCE: 27
ggccggatcc gacaccatga gcacagaaag catg                                34

<210> SEQ ID NO 28
<211> LENGTH: 34
<212> TYPE: DNA
<213> ORGANISM: Artificial Sequence
<220> FEATURE:
<223> OTHER INFORMATION: Adenovirus

<400> SEQUENCE: 28
ggccatcgat gacaccatga gcacagaaag catg                                34

<210> SEQ ID NO 29
<211> LENGTH: 39
<212> TYPE: DNA
<213> ORGANISM: Artificial Sequence
<220> FEATURE:
<223> OTHER INFORMATION: Adenovirus

<400> SEQUENCE: 29
cgcgaatatt taaatccatt cccttcacag agcaatgac                           39

<210> SEQ ID NO 30
<211> LENGTH: 38
<212> TYPE: DNA
<213> ORGANISM: Artificial Sequence
<220> FEATURE:
<223> OTHER INFORMATION: Adenovirus

<400> SEQUENCE: 30
gcgcgctagc ccaccatgtg ctgtaccaag agtttgct                            38

<210> SEQ ID NO 31
<211> LENGTH: 38
<212> TYPE: DNA
<213> ORGANISM: Artificial Sequence
<220> FEATURE:
<223> OTHER INFORMATION: Adenovirus

<400> SEQUENCE: 31
ggcccaattg tttacatgtt cttgactttt ttactgag                            38

<210> SEQ ID NO 32
<211> LENGTH: 38
<212> TYPE: DNA
<213> ORGANISM: Artificial Sequence
<220> FEATURE:
<223> OTHER INFORMATION: Adenovirus

<400> SEQUENCE: 32
gcgcgctagc ccaccatgtg gaagcccatg ccctcacc                            38

<210> SEQ ID NO 33
<211> LENGTH: 38
<212> TYPE: DNA
<213> ORGANISM: Artificial Sequence
<220> FEATURE:
<223> OTHER INFORMATION: Adenovirus

```
<400> SEQUENCE: 33
ggcccaattg tcaaagcttt ggagtttggg ttttcttg                    38
```